(12) United States Patent
Verruto et al.

(10) Patent No.: US 11,124,798 B2
(45) Date of Patent: Sep. 21, 2021

(54) ALGAL LIPID PRODUCTIVITY VIA GENETIC MODIFICATION OF A TPR DOMAIN CONTAINING PROTEIN

(71) Applicant: Synthetic Genomics, Inc., La Jolla, CA (US)

(72) Inventors: John Verruto, San Diego, CA (US); Eric Moellering, San Diego, CA (US); Imad Ajjawi, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 16/213,928

(22) Filed: Dec. 7, 2018

(65) Prior Publication Data

US 2019/0177738 A1 Jun. 13, 2019

Related U.S. Application Data

(60) Provisional application No. 62/596,671, filed on Dec. 8, 2017.

(51) Int. Cl.
| | |
|---|---|
| *C12N 1/12* | (2006.01) |
| *C12P 7/64* | (2006.01) |
| *C12N 15/82* | (2006.01) |
| *C12N 15/113* | (2010.01) |
| *C12N 1/36* | (2006.01) |

(52) U.S. Cl.
CPC ........... *C12N 15/8247* (2013.01); *C12N 1/12* (2013.01); *C12N 1/36* (2013.01); *C12N 15/113* (2013.01); *C12N 15/8213* (2013.01); *C12P 7/64* (2013.01); *C12N 2310/11* (2013.01); *C12N 2310/141* (2013.01); *C12N 2310/20* (2017.05)

(58) Field of Classification Search
None
See application file for complete search history.

(56) References Cited

U.S. PATENT DOCUMENTS

| | | |
|---|---|---|
| 2003/0138848 A1 | 7/2003 | Moarefi et al. |
| 2006/0123505 A1 | 6/2006 | Kikuchi et al. |
| | (Continued) | |

FOREIGN PATENT DOCUMENTS

| | | |
|---|---|---|
| WO | WO 2008/061153 A2 | 5/2008 |
| WO | WO 2012/005898 A2 | 1/2012 |
| | (Continued) | |

OTHER PUBLICATIONS

Dewez et al., "Mechanism of REP27 protein action in the D1 protein turnover and photosystem II repair from photodamage", Plant Physiology, vol. 151, pp. 88-99, 2009 (Year: 2009).*

(Continued)

*Primary Examiner* — Richard C Ekstrom
(74) *Attorney, Agent, or Firm* — DLA Piper LLP (US)

(57) ABSTRACT

The present invention provides mutant microorganisms having attenuated expression of a gene encoding a polypeptide that includes a TPR domain, wherein the mutant microorganisms have higher lipid productivity and/or exhibit increased partitioning of carbon to lipid as compared to wild type microorganisms from which they are derived. Also provided are methods of producing lipids using the mutant microorganisms, guide RNAs, and nucleic acid constructs used for producing mutant microorganisms.

22 Claims, 4 Drawing Sheets
Specification includes a Sequence Listing.

(56) References Cited

U.S. PATENT DOCUMENTS

2017/0067069 A1    3/2017    Bauman et al.
2019/0177738 A1*   6/2019    Verruto .................... C12N 1/36

FOREIGN PATENT DOCUMENTS

WO    WO 2017/011707 A1    1/2017
WO    WO 2017/070404 A3    4/2017

OTHER PUBLICATIONS

Gurvitz et al., "The tetratricopeptide repeat domains of human, tobacco, and nematode PEX5 proteins are functionally interchangeable with the analogous native domain for peroxisomal import of PTS1-terminated proteins in yeast", Molecular Genetics and Genomics, vol. 2665, pp. 276-286, 2001 (Year: 2001).*
Carpinelli, E. C. et al.: "*Chromosome Scale Genome Assembly and Transcriptome Profiling of Nannochloropsis gaditana in Nitrogen Depletion*"; Molecular Plant., Feb. 2014, vol. 7, No. 2, pp. 323-335.
International Search Report dated Apr. 24, 2019, regarding PCT/US2018/064505.

* cited by examiner

SEQUENCE LISTING

<160> NUMBER OF SEQ ID NOS: 25

<210> SEQ ID NO 1
<211> LENGTH: 51
<212> TYPE: PRT
<213> ORGANISM: Nannochloropsis gaditana
<220> FEATURE:
<221> NAME/KEY: misc_feature
<223> OTHER INFORMATION: TPR domain of polypeptide of SEQ ID NO:3 (TRP-6029)

<400> SEQUENCE: 1

Lys Ala Glu Gly Asn Glu Arg Phe Arg Asn Gly Arg Leu Arg Ser Ala
1               5                   10                  15

Leu Glu Cys Tyr Glu Glu Ala Val Arg Met Asp Pro Ser Glu Pro Val
                20                  25                  30

Tyr Tyr Ala His Arg Ser Thr Cys Leu Phe Glu Leu Gly Lys Tyr Ala
            35                  40                  45

Ala Ser Cys
    50

<210> SEQ ID NO 2
<211> LENGTH: 91
<212> TYPE: PRT
<213> ORGANISM: Nannochloropsis gaditana
<220> FEATURE:
<221> NAME/KEY: misc_feature
<223> OTHER INFORMATION: DUF4470 of polypeptide of SEQ ID NO:3 (TRP-6029)

<400> SEQUENCE: 2

Asp Asp Gly Gly Ile Asp Leu Leu Ala Arg Pro Glu Gly Glu Arg Asp
1               5                   10                  15

Leu Ala Leu Leu Phe Gly Gly Leu Gly Asp Ala Arg Gln Pro Leu Ala
                20                  25                  30

Thr Phe Arg Asp Ile Tyr Gln Gln Val Lys Gly Ser Lys Gly Gln Leu
            35                  40                  45

Thr Tyr Lys Thr Met Ser Leu Ser Met Ile Leu Asn Asp Val Lys Ala
        50                  55                  60

Glu Cys Leu Thr Arg Ala Val Ile Met Phe Lys Ala Leu Ala Glu Leu
65                  70                  75                  80

Gly Ile Ile Leu Gln Glu Ala Ala Arg Glu Gln
                85                  90

<210> SEQ ID NO 3
<211> LENGTH: 1249
<212> TYPE: PRT
<213> ORGANISM: Nannochloropsis gaditana
<220> FEATURE:
<221> NAME/KEY: misc_feature
<223> OTHER INFORMATION: TRP-6029 protein

<400> SEQUENCE: 3

Met Glu Ala Arg Ser Arg Lys Leu Ala Arg Lys Asn Ala Ala Phe Glu
1               5                   10                  15

Val Lys Ala Glu Gly Asn Glu Arg Phe Arg Asn Gly Arg Leu Arg Ser
            20                  25                  30

Ala Leu Glu Cys Tyr Glu Glu Ala Val Arg Met Asp Pro Ser Glu Pro
        35                  40                  45

Val Tyr Tyr Ala His Arg Ser Thr Cys Leu Phe Glu Leu Gly Lys Tyr
    50                  55                  60

Ala Ala Ser Cys Glu Asp Ser Lys Gln Ala Ser Leu Leu Tyr Arg Asp
65                  70                  75                  80

Lys Gln Gln Ile Gly Met Ile Ser Arg Thr Glu Ala Asn Ala Ala Ile
                85                  90                  95

Ala Arg Leu Leu Arg Gln Ser Ala Arg Ala Phe Leu Cys Val Asn Thr
            100                 105                 110

Pro His Ser Leu Glu Ala Ala Lys Ala Leu Leu Ala Arg Thr Ile Glu
        115                 120                 125

Leu His Pro Asp Pro Asp Ala Glu Leu Leu Ser Met Gln Ala Gly Ala
    130                 135                 140

Cys Gln Ala Val Ala Glu Ala Asp Ser Ala Met Ala Gly Glu Gly Ser
145                 150                 155                 160

Gly Pro Gly Tyr Met Val Gln Ser Ser Ser Lys His Gly Arg Gly Cys
                165                 170                 175

His Met Gly Ile Gly Gly Gly Ser Cys Asp Tyr Leu Pro Arg Tyr Arg
            180                 185                 190

Ser Pro Val Val Asn Gly Pro Thr Pro Tyr Ser Cys Ile Gly Trp Glu
        195                 200                 205

Leu Gly Leu Ser Gly Leu Ala Gly Arg Val Pro Ser Pro Ala Asp Thr
    210                 215                 220

Glu Ser Pro Phe Ser Ala His Gly Gly Thr Phe Gly Glu Asp Glu Asp
225                 230                 235                 240

Asp Gly Gly Ile Asp Leu Leu Ala Arg Pro Glu Gly Glu Arg Asp Leu
                245                 250                 255

Ala Leu Leu Phe Gly Gly Leu Gly Asp Ala Arg Gln Pro Leu Ala Thr
            260                 265                 270

Phe Arg Asp Ile Tyr Gln Gln Val Lys Gly Ser Lys Gly Gln Leu Thr
        275                 280                 285

Tyr Lys Thr Met Ser Leu Ser Met Ile Leu Asn Asp Val Lys Ala Glu
    290                 295                 300

Cys Leu Thr Arg Ala Val Ile Met Phe Lys Ala Leu Ala Glu Leu Gly
305                 310                 315                 320

Ile Ile Leu Gln Glu Ala Ala Arg Glu Gln Gly Met Glu Gly Gly Met
                325                 330                 335

Glu Gly Val Asp Glu Gly Val Ala Gly Thr Gly Ser Leu Asp Pro Leu
            340                 345                 350

-continued

Ala Leu Leu Glu Ser Ser Asp Ala Val Ala Glu Ala Val Tyr Arg Cys
        355                 360                 365

Tyr His Leu Tyr Leu Gly Ala Phe Leu Met Pro Asn Glu Ala Asp Trp
    370                 375                 380

Leu Gln Arg Thr Leu Asn Asp Met Ser Lys Ser Asn Ser Leu Thr Gln
385                 390                 395                 400

Ala Ser Ser Leu Pro Gly Ser Asp His Asp Ala Arg Val Gly Ser Ser
                405                 410                 415

Pro Pro Leu Ala Ser Thr Pro Ser Ala Gly Pro Ser Leu Leu Asp Ala
            420                 425                 430

Ser Gln Ser Ser Thr Pro Phe Gln Phe Ser Ser Asn Leu Gly Phe Ser
        435                 440                 445

Trp Leu Lys Ile Lys Ala Lys Lys Asp Arg Glu Ala Val Lys Asn Val
    450                 455                 460

Val Asp His Trp Arg Val Leu Cys Lys Thr Met Gly Ala Asp Val Met
465                 470                 475                 480

Ala Arg Ile Tyr Gln Ser Ser Met Gln Arg Pro Thr Glu Glu Asp Glu
                485                 490                 495

Gly Gly Leu Gln Thr Ala Ser His Asp Arg Gly Gly Thr Gly Gly
            500                 505                 510

Gly Ala Arg Ala Asp Ala Met Glu Glu Ser Asn Leu Ser Leu Glu Gln
        515                 520                 525

Gln Trp Arg Ala Gln Val Arg Glu Ala Met Leu Glu Gln Ile Glu Ala
    530                 535                 540

Met Asp Asp Glu Glu Ile Asn Gln Met Arg Glu Ala Glu Gly Ala Thr
545                 550                 555                 560

Pro Glu Glu Lys Arg Ala Phe Leu Arg Asp His Trp Ala Glu Asp Val
                565                 570                 575

Asp Pro Arg Thr Leu Asp Leu Met Arg His Leu Pro Ala Ala His Arg
            580                 585                 590

Glu Ile Asp Phe Phe His Thr Thr Met Leu Leu Pro Val Pro Thr Pro
        595                 600                 605

Glu Ala Ala Arg Gly Met Gly Leu Met Asp Lys Ser Gln Gly Arg Asn
    610                 615                 620

Leu His Asn Ala Trp Arg Pro Asn Val Thr Leu Val Ser Ala Asp Ile
625                 630                 635                 640

Pro Met Glu Ala Met Leu Pro Gly Lys Leu Asp Lys Ala Ala Val Ala
                645                 650                 655

Ser Ser Ser Leu Thr Glu Leu His Phe Cys Pro Phe Lys Ala Leu Lys
            660                 665                 670

Leu Leu Leu Ile Gln Pro Gly Asp Glu Asn His Leu Ala Arg Gln Glu
        675                 680                 685

Ala Phe Arg Ser Ala Ala Leu Phe Phe Ser Glu Val Ala Leu Gly Leu
    690                 695                 700

Ala Gly Phe Leu Glu Ala Gly Thr Leu Lys Met Gln Met Phe Leu Gly
705                 710                 715                 720

Asp Val His Asp Leu Gly Ser Thr Arg Ala Pro Asn Ser Leu Asp Arg
                725                 730                 735

Val Leu Ile Ser Asn Val Pro Asp Tyr Thr Thr Leu Leu Pro Ser Met
            740                 745                 750

Ile Lys Leu Ile Pro Leu Leu Lys Thr Ser Pro Gly Ser Ala Leu Lys
        755                 760                 765

His Ser Val Leu Lys Phe Asn Ala Asn Phe Gln Asp Leu Pro Glu Tyr
770             775             780

Ala His Ser Met Gly Leu Tyr Val Pro Asp Met Ala Cys Leu Pro Thr
785             790             795             800

Tyr Leu Gly Val Asn His Glu Tyr Gly Gly Ile Trp Ala His Leu Ile
            805             810             815

Glu Trp Ser Arg Ala Pro Pro Leu Leu Leu Glu Gly Pro Gly Glu Glu
            820             825             830

Ser Leu His Leu Asp Met Glu Lys Asp Glu Ser Thr Pro His Arg Thr
            835             840             845

Ser Ser Pro Ala Pro Phe Thr Thr Pro Leu Pro Pro Thr Gln His Leu
850             855             860

Pro Ser Gly Arg Asp Val Gln Ala Trp Leu Ser Thr Val Phe Leu Ser
865             870             875             880

Ile Ala Met Pro Leu Cys Arg Asp Cys Val Leu Thr His Thr Glu Ile
            885             890             895

Arg Pro Leu Thr Leu Gln Ala Phe Phe Glu Leu Cys His Tyr Leu Val
            900             905             910

Ala His Met Asp Phe Pro Pro His Asn Leu Ala Trp Val Ile Glu His
915             920             925

Ala Met Ile Gly Glu Leu Thr Thr Ala Ala Val Pro Pro Asp Lys Thr
930             935             940

Pro Trp Leu Pro Gln Tyr Thr Trp Arg Gln Gln Leu Ser Arg Ala
945             950             955             960

Val Pro Thr Gly Ala Phe Ser Leu Glu Thr Arg Thr Leu Ala Gly Leu
            965             970             975

Trp Gln Pro Lys Leu Gly Phe Arg Leu Cys Ala Pro Val Gly His Arg
            980             985             990

Leu Pro Arg Pro Glu Asp Val Thr Gln Leu Arg Leu Thr Val Pro Trp
            995             1000            1005

Arg Gln Gln Leu Pro Cys Glu Gly Arg Glu Ser Ala Glu Ala Val
        1010            1015            1020

Ala Val Gln Ala Glu Ser Cys Leu Lys Ala Thr Gly Val Pro Leu
        1025            1030            1035

Ala Lys Val Val Gly Ala Val Leu Val Ser Pro Ala Phe Leu Ala
        1040            1045            1050

Thr His Ala Glu Ala Phe Asp Pro Ser Lys His Tyr Val Gln Met
        1055            1060            1065

Pro Pro His Gly Cys Ser His Thr Ala Cys Thr Phe Ser Ser Ser
        1070            1075            1080

Pro Ser Lys Thr Gly His Glu Pro His Pro Thr Pro Glu Asn Gln
        1085            1090            1095

Gly Leu Arg Pro Leu Leu Leu Ala Pro Ala Ala Gln Lys Ser Gly
        1100            1105            1110

Asp Val His Leu Phe Ser Cys Val Arg Trp Asp Ser Arg Thr Ser
        1115            1120            1125

Leu Val Thr Leu Leu Met Pro Lys Asp Asp Leu Arg Gln Leu Val
        1130            1135            1140

Ala Arg Ser Phe His Leu Cys Leu Leu Arg Thr Asp Ser Trp Gln
        1145            1150            1155

Pro Leu Thr Lys Pro Phe Pro Leu Ser Asp Asp Pro Ala Leu Leu
        1160            1165            1170

Arg Pro His Ile His Ala His Met Gln Glu Met Gln Glu Leu Arg

| | | | | | | | | | | |
|---|---|---|---|---|---|---|---|---|---|---|
| | | 1175 | | | 1180 | | | 1185 | | |
| Glu | Ser | Glu | Leu | Gly | Glu | Ala | Val | Gly | Glu | Thr | Thr | Glu | Ser | Ala |
| | 1190 | | | | 1195 | | | | 1200 | |

Glu Ser Glu Leu Gly Glu Ala Val Gly Glu Thr Thr Glu Ser Ala
     1190                 1195                 1200

Met Asp Val Glu Ile Ala Glu Gly Gly His Ile Gly Ala Tyr Gly
     1205                 1210                 1215

Asn Pro Ala Glu Thr Gly Arg Gly Met Val Ser Gly Asn Ala Ser
     1220                 1225                 1230

Leu Val Ala Thr Ala Glu Glu Arg Leu Leu His Lys Tyr Arg Thr
     1235                 1240                 1245

Tyr

```
<210> SEQ ID NO 4
<211> LENGTH: 3750
<212> TYPE: DNA
<213> ORGANISM: Nannochloropsis gaditana
<220> FEATURE:
<221> NAME/KEY: misc_feature
<223> OTHER INFORMATION: TRP-6029 open reading frame (ORF)

<400> SEQUENCE: 4
```

| | | | | | | |
|---|---|---|---|---|---|---|
| atggaagctc | gatcaagaaa | gctcgcccgc | aaaaatgcgg | cctttgaagt | caaagcggaa | 60 |
| ggaaacgaac | gctttcgtaa | tggccgcctg | cgatcagcgt | tggaatgtta | tgaagaggcc | 120 |
| gtgcgcatgg | atccttccga | gcccgtgtac | tatgcccaca | ggtccacctg | cctctttgag | 180 |
| ctggggaagt | atgcggcctc | ctgcgaagac | tccaagcaag | cctccctcct | gtaccgggac | 240 |
| aagcaacaga | tcggcatgat | atcccgcacg | gaggccaacg | ctgccatcgc | ccgcttgctt | 300 |
| cgccagtccg | cccgcgcttt | cctctgcgtc | aacaccccac | acagccttga | agctgccaag | 360 |
| gccctcttgg | cccgaaccat | cgaacttcac | cccgaccccg | acgcggagct | tctctccatg | 420 |
| caggcaggcg | cctgtcaagc | cgtggcagaa | gcggactcgg | ccatggcagg | agaaggttca | 480 |
| gggcctggat | acatggtgca | atcctcctcg | aaacacggta | gggatgtca | catggggatc | 540 |
| ggcggtggct | cctgcgatta | cttgccgcgg | taccgatctc | ccgttgtgaa | cggtcccacg | 600 |
| ccctattcct | gcattggatg | ggagttgggc | ttgtcgggat | tggccggtcg | tgtcccctcg | 660 |
| cccgcggata | cagagtcgcc | cttctcggcc | acggagggga | cgttcgggga | ggacgaggac | 720 |
| gacggaggca | tcgacttgtt | ggctcggccg | gagggtgaga | gggacctggc | gctcctcttc | 780 |
| gggggttttgg | gggacgcgcg | ccagccgctg | gcgacgtttc | gggacattta | tcagcaagtg | 840 |
| aaggggagca | agggccagtt | gacttacaaa | acgatgagtc | tgtcgatgat | cttgaacgac | 900 |
| gtgaaggcga | gtgcctgac | ccgggccgtg | ataatgttca | aggcgctggc | agagctcgga | 960 |
| atcatcctgc | aggaggcggc | tagggagcaa | gggatggagg | ggggatgga | gggagtggac | 1020 |
| gaggggtgg | cggggacggg | aagcttagat | ccactggcat | tgctcgagag | ctcgacgca | 1080 |
| gtagcagagg | ctgtgtatcg | ctgctaccac | ctctacttgg | gcgccttcct | gatgcccaac | 1140 |
| gaagccgatt | ggctgcaacg | gacactaaac | gacatgagta | agagcaactc | gctccaccag | 1200 |
| gcctccagtc | tccccggcag | cgaccacgat | gcccgcgtcg | gcagcagtcc | tcccctcgcg | 1260 |
| tccacgccgt | ccgcgggacc | gagcctcctg | gatgcatccc | aatcttccac | gcccttccaa | 1320 |
| ttctcctcca | acctcgggtt | ctcctggttg | aaaatcaagg | ccaagaaaga | tagggaggcg | 1380 |
| gtcaagaacg | tggtggacca | ttggcgcgtc | ctgtgcaaga | ccatgggagc | ggacgtgatg | 1440 |
| gcgcgcatct | accaatcctc | catgcagagg | ccgaccgagg | aggatgaggg | ggggttgcag | 1500 |
| acggcttcgc | acgaccgagg | gggagggact | ggggggggcg | ccagggcgga | tgccatggag | 1560 |

```
gagtcaaatt tgagtttgga gcaacagtgg agggcacagg tgagggaggc gatgttggaa    1620
caaatcgagg cgatggacga cgaggagatc aatcagatgc gggaagcgga aggggcgacg    1680
ccggaagaga agcgggcctt tttgcgcgac cactgggcgg aagacgtgga tccccgcacc    1740
ttggacctca tgcggcacct gcccgcggcg caccgtgaaa tcgactttt  ccacaccacc    1800 atgctcttac cggtacccac cccggaggcc gcacgggcac tgggcttgat ggacaagagc    1860
caaggccgta atttgcacaa cgcctggcgg cccaatgtga ccttggtctc ggcagacatt    1920
cccatggagg ccatgttgcc gggcaagctg acaaagcgg  ccgttgcctc ctcctccttg    1980
acagagctcc atttctgccc attcaaagcc ttgaaattgt tgttgattca gcccggggac    2040
gagaaccact tggcccgtca agaagcctcc gatcagccg  cgctgttctt ctcagaagta    2100
gcactgggac tggccgggtt cttggaagca gggaccctga aaatgcaaat gttccttggc    2160
gacgtgcacg atctgggcag cacgcgcgcc cccaatagct tggaccgtgt tctcatcagc    2220
aacgtccccg actacaccac gcttcttccc tccatgatca aactcatccc cctcctcaaa    2280
acgagtcctg gatccgcctt gaagcacagt gtgctgaaat ttaatgccaa ttttcaagac    2340
ttgcccgaat acgcacactc catggggttg tatgtgcccg acatggcctg cctcccgacc    2400
tatctgggtg tgaaccacga atacggaggc atatgggccc acttgatcga gtggagtcgc    2460
gcgccgccct tgctcctgga aggccccgga gaggagagtc ttcacctcga catggagaag    2520
gacgagagca cgccccaccg gacatcctcc ccagcccctt ttaccacccc gctcccgccc    2580
acacagcacc tcccctccgg gcgcgatgtg caagcctggc tctccacggt gtttctcagt    2640
atcgccatgc ccttgtgtcg ggattgcgtg ctcacacaca ccgagatccg cccgctcacc    2700
cttcaggcct ttttcgagct ctgtcattac ctggtcgcac acatggactt cccacccac     2760 aatttggctt gggtcatcga gcacgccatg atcggagagc ttaccactgc tgcggtaccc    2820
cctgacaaga caccctggct gccccagtac acatggcgcc agcagcagct ttcgcgcgca    2880
gtgcccacgg gggctttctc cctggaaacg cgaacgctcg ccgggctatg gcagccgaaa    2940 cttggttttcc gcctgtgtgc gccagtcgga catcgcttgc cacggccaga ggacgtcacg    3000
cagctgcgct tgacggtacc gtggcgccag cagcttccct gtgaagggag agaaagtgcg    3060
gaagcggtgg ctgttcaagc cgaatcctgt ctgaaagcga cgggcgtacc gctggcaaag    3120
gtcgtgggcg ccgtcttagt ctcccctgct tttctagcga cgcatgccga agccttcgat    3180
ccctccaaac attacgtgca aatgcctcct cacggttgct ctcacaccgc ctgcactttc    3240
tcttcctcgc ccagcaagac tggccacgaa ccccatccaa ctcccgaaaa ccaagggctg    3300 cggccccctcc tcctggctcc tgcagcgcaa aaaagtggtg acgtacacct cttctcttgt    3360
gtccgttggg actcacggac ctcgctggtc acccttctca tgcccaagga cgacttgcgg    3420
cagctcgttg ccaggagttt ccatctctgt ttactgcgaa cggacagttg caacccctc     3480 accaagcctt tccccctctc ggacgacccg gccttgctcc ggccgcacat ccatgcgcac    3540
atgcaggaga tgcaggaatt gcgggaaagt gaactcgggg aggccgtggg agagacgact    3600
gaatccgcca tggacgtgga gatcgcggaa gggggccaca tagggggccta cgggaatcca    3660 gcagagaccg gcagagggat ggtatcgggg aatgcctcgc ttgtggcaac tgctgaggag    3720
cgtttactgc acaaataccg cacatattga                                    3750

<210> SEQ ID NO 5
<211> LENGTH: 23
<212> TYPE: DNA
<213> ORGANISM: Nannochloropsis gaditana
```

```
<220> FEATURE:
<221> NAME/KEY: misc_feature
<223> OTHER INFORMATION: Target sequence in TPR-6029 gene (PAM
      underlined)

<400> SEQUENCE: 5
ggatgtcaca tggggatcgg cgg                                               23

<210> SEQ ID NO 6
<211> LENGTH: 11263
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Vector pSGE-6206

<400> SEQUENCE: 6
gcggccgccg tatggtcgac ggttgctcgg atgggggggg cggggagcga tggagggagg        60
aagatcaggt aaggtctcga cagactagag aagcacgagt gcaggtataa gaaacagcaa       120
aaaaaagtaa tgggcccagg cctggagagg gtatttgtct tgttttctt tggccaggaa        180 cttgttctcc tttcttcgtt tctaggaccc cgatccccgc tcgcatttct ctcttcctca       240
gccgaagcgc agcggtaaag catccatttt atcccaccga aagggcgctc ccagccttcg      300
tcgagcggaa ccggggttac agtgcctcaa ccctcccaga cgtagccaga gggaagcaac       360
tccctgatgc caaccgctgt gggctgccca tcggaatctt tgacaattgc cttgatcccc      420
gggtgcaagt caagcagcac ctgccgacat cgcccgcacg gagacagaat gccgcggttt       480
tcgttcccga tggccactat gcacgtcaga tttccggcag cagccgcagc ggccgttccg       540
aggaccacga gctccgcgca tggccctccg gtgaaatgat atacattcac gccggtaaag       600
atccgaccgt cggacgagag ggctgcactg gccaccgagt agtcctcgct aataggtatg       660
ctgttgatgg tcgcagttgc acgttcgatc agcgtggatt cctcttggga taaaggcttg       720
gccatcgagc tcggtacccg gggatccatg attgttgtat tatgtaccta tgtttgtgat       780
gagacaataa atatgagaag agaacgttgc ggccactttt ttctccttcc ttcgcgtgct       840
catgttggtg gtttgggagg cagaagatgc atggagcgcc acacattcgg taggacgaaa       900
cagcctcccc cacaaaggga ccatgggtag ctaggatgac gcacaagcga gttcccgctc       960
tcgaagggaa acccaggcat ttccttcctc ttttcaagcc acttgttcac gtgtcaacac      1020
aattttggac taaatgccc tcggaactc ggcaggcctc cctctgctcc gttgtcctgg       1080
tcgccgagaa cgcgagaccg tgccgcatgc catcgatctg ctcgtctgta ctactaatcg      1140
tgtgcgtgtt cgtgcttgtt tcgcacgaaa ttgtcctcgt tcggccctca caacggtgga      1200
aatcggtgct agaataaagt gaggtggctt atttcaatgg cggccgtcat catgcgggat      1260
caactgaagt acggcgggtt ctcgagattt catcgtgctc gtccagagca ggtgttttgc      1320
ctgcagctct tcatgtttag gggtcatgat ttcatctgat atgccgtaag aaaaccaata      1380
ttcacttctc aattttccat ggaaaggtga aggcctaggt tgtgtgcgag gcaacgactg      1440
gggagggatc gcaacattct tgctaacctc ccctctatct tggccgctgt gaatcggcat      1500
atttaccggg ctgaattgag aaagtgtttt gagggaatta aaaggtggct gtcttgcaag      1560
cttggcttca gtgcctgctt aattcgaacc gatccagctt gtgatgaggc cttcctaagc      1620
ctggtagtca gaagcgacat ggcgctataa atttcgtctc agttggagag tagaaaagca      1680
tgattcgaac acggttttca actgccaaag atatctccat tgtttccttc aatctgtaca      1740
```

```
cctgcacggt gcaccagttg gtacggcata ttatggttta ataagcatac atcatatgaa    1800
tacaattcag cttaaattta tcatacaaag atgtaagtgc agcgtgggtc tgtaacgatc    1860
gggcgtaatt taagataatg cgagggaccg ggggaggttt tggaacggaa tgaggaatgg    1920
gtcatggccc ataataataa tatgggtttg gtcgcctcgc acagcaaccg tacgtgcgaa    1980
aaaggaacag atccatttaa taagttgaac gttattcttt cctatgcaat gcgtgtatcg    2040
gaggcgagag caagtcatag gtggctgcgc acaataattg agtctcagct gagcgccgtc    2100
cgcgggtggt gtgagtggtc atcctcctcc cggcctatcg ctcacatcgc ctctcaatgg    2160
tggtggtggg gcctgatatg acctcaatgc cgacccatat taaaacccag taaagcattc    2220
accaacgaac gaggggctct tttgtgtgtg ttttgagtat gattttacac ctctttgtgc    2280
atctctctgg tcttccttgg ttcccgtagt ttgggcatca tcactcacgc ttccctcgac    2340
cttcgttctt cctttacaac cccgacacag gtcagagttg gagtaatcaa aaaggggtg    2400 cacgaatgag atacattaga ttttgacaga tatcctttta ctggagaggg ttcaagggat    2460
caaatgaaca gcgggcgttg gcaatctagg gagggatcgg aggttggcag cgagcgaaag    2520
cgtgtccatc cttttggctg tcacacctca cgaaccaact gttagcaggc cagcacagat    2580
gacatacgag aatctttatt atatcgtaga ccttatgtgg atgacctttg gtgctgtgtg    2640
tctggcaatg aacctgaagg cttgataggg aggtggctcc cgtaaaccct ttgtcctttc    2700
cacgctgagt ctcccccgca ctgtccttta tacaaattgt tacagtcatc tgcaggcggt    2760
ttttctttgg caggcaaaga tgcccaagaa aaagcggaag gtcggcgact acaaggatga    2820
cgatgacaag ttggagcctg agagaagcc ctacaaatgc cctgagtgcg aaagagctt    2880 cagccaatct ggagccttga cccggcatca acgaacgcat acacgagaca agaagtactc    2940
catcgggctg gacatcggga cgaactccgt gggatgggcc gtgatcacag acgaatacaa    3000
ggtgccttcc aagaagttca aggtgctggg gaacacggac agacactcca tcaagaagaa    3060
cctcatcggg gccttgctct tcgactccgg agaaaccgcc gaagcaacgc gattgaaaag    3120
aaccgccaga agacgataca cacgacggaa gaaccgcatc tgctacctcc aggagatctt    3180
cagcaacgag atggccaagg tggacgactc gttctttcat cgcctggagg agagcttcct    3240
ggtggaggaa gacaagaaac atgagcgcca cccgatcttc gggaacatcg tggacgaagt    3300
ggcctaccac gagaaatacc ccacgatcta ccacttgcgc aagaaactcg tggactccac    3360
ggacaaagcg gacttgcggt tgatctactt ggccttggcc cacatgatca aatttcgggg    3420
ccacttcctg atcgagggcg acttgaatcc cgacaattcc gacgtggaca gctcttcat    3480 ccagctggtg cagacctaca accagctctt cgaggagaac cccatcaatg cctccggagt    3540
ggacgccaaa gccatcttgt ccgcccgatt gtccaaatcc agacgcttgg agaacttgat    3600
cgcacaactt cctggcgaga agaagaacgg cctcttcggc aacttgatcg cgctgtcgct    3660
gggattgacg cctaacttca gtccaacttc gacttggcc gaggacgcca agttgcaact    3720
gtccaaggac acctacgacg acgacctcga caacctgctg gcccaaattg gcgaccaata    3780
cgcggacttg tttttggcgg ccaagaactt gagcgacgcc atcttgttga gcgacatctt    3840
gcgcgtgaat acgagatca ccaaagcccc tttgtccgcc tctatgatca gcggtacga    3900 cgagcaccac caagacttga ccctgttgaa agccctcgtg cggcaacaat gcccgagaa    3960 gtacaaggag atcttcttcg accagtccaa gaacgggtac gccggctaca tcgacggagg    4020
agcctcccaa gaagagttct acaagttcat caagcccatc ctggagaaga tggacggcac    4080
```

```
cgaggagttg ctcgtgaagc tgaaccgcga agacttgttg cgaaaacagc ggacgttcga    4140
caatggcagc atccccacc aaatccattt gggagagttg cacgccatct tgcgacggca     4200
agaggacttc tacccgttcc tgaaggacaa ccgcgagaaa atcgagaaga tcctgacgtt    4260
cagaatcccc tactacgtgg gacccttggc ccgaggcaat tcccggtttg catggatgac    4320
gcgcaaaagc gaagagacga tcacccctg gaacttcgaa gaagtggtcg acaaaggagc    4380
atccgcacag agcttcatcg agcgaatgac gaacttcgac aagaacctgc ccaacgagaa    4440
ggtgttgccc aagcattcgc tgctgtacga gtacttcacg gtgtacaacg agctgaccaa    4500
ggtgaagtac gtgaccgagg gcatgcgcaa acccgcgttc ctgtcgggag agcaaaagaa    4560
ggccattgtg gacctgctgt tcaagaccaa ccggaaggtg accgtgaaac agctgaaaga    4620
ggactacttc aagaagatcg agtgcttcga ctccgtggag atctccggcg tggaggaccg    4680
attcaatgcc tccttgggaa cctaccatga cctcctgaag atcatcaagg acaaggactt    4740
cctggacaac gaggagaacg aggacatcct ggaggacatc gtgctgaccc tgaccctgtt    4800
cgaggaccga gagatgatcg aggaacggtt gaaaacgtac gcccacttgt tcgacgacaa    4860
ggtgatgaag cagctgaaac gccgccgcta caccggatgg ggacgattga gccgcaaact    4920
gattaatgga attcgcgaca gcaatccgg aaagaccatc ctggacttcc tgaagtccga    4980
cgggttcgcc aaccgcaact tcatgcagct catccacgac gactccttga ccttcaagga    5040
ggacatccag aaggcccaag tgtccggaca aggagactcc ttgcacgagc acatcgccaa    5100
tttggccgga tcccccgcaa tcaaaaaagg catcttgcaa accgtgaaag tggtcgacga    5160
actggtgaag gtgatgggac ggcacaagcc cgagaacatc gtgatcgaaa tggcccgcga    5220
gaaccaaacc acccaaaaag gacagaagaa ctcccgagag cgcatgaagc ggatcgaaga    5280
gggcatcaag gagttgggct cccagatcct gaaggagcat cccgtggaga atacccaatt    5340
gcaaaacgag aagctctacc tctactacct ccagaacggg cgggacatgt acgtcgacca    5400
agagctggac atcaaccgcc tctccgacta cgatgtggat catattgtgc cccagagctt    5460
cctcaaggac gacagcatcg acaacaaggt cctgacgcgc agcgacaaga accggggcaa    5520
gtctgacaat gtgccttccg aagaagtcgt gaagaagatg aagaactact ggcggcagct    5580
gctcaacgcc aagctcatca cccaacggaa gttcgacaac ctgaccaagg ccgagagagg    5640
aggattgtcc gagttggaca aagccggctt cattaaacgc caactcgtgg agacccgcca    5700
gatcacgaag cacgtggccc aaatcttgga ctcccggatg aacacgaaat acgacgagaa    5760
tgacaagctg atccgcgagg tgaaggtgat cacgctgaag tccaagctgg tgagcgactt    5820
ccggaaggac ttccagttct acaaggtgcg ggagatcaac aactaccatc acgcccatga    5880
cgcctacctg aacgccgtgg tcggaaccgc cctgatcaag aaatacccca agctggagtc    5940
cgaattcgtg tacggagatt acaaggtcta cgacgtgcgg aagatgatcg cgaagtccga    6000
gcaggagatc ggcaaagcca ccgccaagta cttcttttac tccaacatca tgaacttctt    6060
caagaccgag atcacgctcg ccaacggcga gatccgcaag cgcccctga tcgagaccaa    6120 cggcgagacg ggagagattg tgtgggacaa aggaagagat tttgccacag tgcgcaaggt    6180
gctgtccatg cctcaggtga acatcgtgaa gaagaccgag gtgcaaacag agggttttc    6240 caaagagtcc attttgccta agaggaattc cgacaagctc atcgcccgca agaaggactg    6300 ggacccaag aagtacgggg gcttcgactc ccccacggtg gcctactccg tgttggtggt    6360
ggccaaagtg gagaaaggga agagcaagaa gctgaaatcc gtgaaggagt tgctcggaat    6420
cacgatcatg gaacgatcgt cgttcgagaa aaaccccatc gacttcctcg aagccaaagg    6480
```

```
gtacaaagag gtgaagaagg acctgatcat caagctgccc aagtactccc tgttcgagct    6540
ggagaacggc cgcaagcgga tgctggcctc cgccggggaa ctgcagaaag gaacgaatt     6600 ggccttgccc tccaaatacg tgaacttcct ctacttggcc tcccattacg aaaagctcaa    6660
aggatcccct gaggacaatg agcagaagca actcttcgtg gaacaacaca agcactacct    6720
ggacgagatc atcgagcaga tcagcgagtt ctccaagcgc gtgatcctcg ccgacgccaa    6780
cctggacaag gtgctctccg cctacaacaa gcaccgcgac aagcctatcc gcgagcaagc    6840
cgagaatatc attcacctgt ttaccctgac gaatttggga gcccctgccg cctttaaata    6900
ctttgacacc accatcgacc gcaaaagata cacctccacc aaggaagtct ggacgccac     6960 cctcatccac cagtccatca cgggcctcta cgagacgcgc atcgacctct cccaattggg    7020
cggcgactaa agtgatgcgg cctttaggaa acaccacaaa agtaattgac aatctcagga    7080
acgatctgcg tgtttacagc ttcccaaata acaattatac cacgtaccaa aaggggttta    7140
atgtatctca caaattcttc taataggtac agcttctcaa attgggtgta tgatgtgaca    7200
cttcgtctca cacacgtcac gataattcag cgtatggctt cccttcatca cattcacgca    7260
aacttctaca caaccctggg catatttctt gtgttggcaa cactcccgaa atcgattctg    7320
cacacaatgg ttcattcaat gattcaagta cgttttagac ggactaggca gtttaattaa    7380
aaacatctat cctccagatc accagggcca gtgaggccgg cataaaggac ggcaaggaaa    7440
gaaaagaaag aaagaaaagg acacttatag catagtttga agttataagt agtcgcaatc    7500
tgtgtgcagc cgacagatgc tttttttttc cgtttggcag gaggtgtagg gatgtcgaag    7560
accagtccag ctagtatcta tcctacaagt caatcatgct gcgacaaaaa tttctcgcac    7620
gaggcctctc gataaacaaa actttaaaag cacacttcat tgtcatgcag agtaataact    7680
cttccgcgtc gatcaattta tcaatctcta tcatttccgc cccttccctt gcatagagca    7740
agaaaagcga cccggatgag gataacatgt cctgcgccag tagtgtggca ttgcctgtct    7800
ctcatttaca cgtactgaaa gcataatgca cgcgcatacc aatattttc gtgtacggag     7860 atgaagagac gcgacacgta agatcacgag aaggcgagca cggttgccaa tggcagacgc    7920
gctagtctcc attatcgcgt tgttcggtag cttgctgcat gtcttcagtg gcactatatc    7980
cactctgcct cgtcttctac acgagggcca catcggtgca agttcgaaaa atcatatctc    8040
aatcttcaga tcctttccag aaacggtgct caggcgggaa agtgaaggtt ttctactcta    8100
gtggctaccc caattctctc cgactgtcgc agacggtcct tcgttgcgca cgcaccgcgc    8160
actacctctg aaaattcgaca accgaagttc aattttacat ctaacttctt tcccattctc   8220
tcaccaaaag cctagcttac atgttggaga gcgacgagag cggcctgccc gccatggaga    8280
tcgagtgccg catcaccggc accctgaacg gcgtggagtt cgagctggtg ggcggcgag     8340 agggcacccc cgagcagggc cgcatgacca acaagatgaa gagcaccaaa ggcgccctga    8400
ccttcagccc ctacctgctg agccacgtga tgggctacgg cttctaccac ttcggcacct    8460
accccagcgg ctacgagaac cccttcctgc acgccatcaa caacggcggc tacaccaaca    8520
cccgcatcga gaagtacgag gacggcggcg tgctgcacgt gagcttcagc taccgctacg    8580
aggccggccg cgtgatcggc gacttcaagg tgatgggcac cggcttcccc gaggacagcg    8640
tgatcttcac cgacaagatc atccgcagca acgccaccgt ggagcacctg caccccatgg    8700
gcgataacga tctggatggc agcttcaccc gcaccttcag cctgcgcgac ggcggctact    8760
acagctccgt ggtggacagc cacatgcact tcaagagcgc catccacccc agcatcctgc    8820
```

```
agaacggggg cccccatgttc gccttccgcc gcgtggagga ggatcacagc aacaccgagc    8880
tgggcatcgt ggagtaccag cacgccttca gacccccgga tgcagatgcc ggtgaagaat    8940
aagggtggga aggagtcggg gagggtcctg gcagagcggc gtcctcatga tgtgttggag    9000
acctggagag tcgagagctt cctcgtcacc tgattgtcat gtgtgtatag gttaaggggg    9060
cccactcaaa gccataaaga cgaacacaaa cactaatctc aacaaagtct actagcatgc    9120
cgtctgtcca tctttatttc ctggcgcgcc tatgcttgta aaccgttttg tgaaaaaatt    9180
tttaaaataa aaaggggac ctctagggtc cccaattaat tagtaatata atctattaaa    9240
ggtcattcaa aaggtcatcc agacgaaagg gcctcgtgat acgcctattt ttataggtta    9300
atgtcatgat aataatggtt tcttagacgt caggtggcac ttttcgggga aatgtgcgcg    9360
gaaccccctat ttgttttattt ttctaaatac attcaaatat gtatccgctc atgagacaat    9420
aaccctgata aatgcttcaa taatattgaa aaggaagag tatgagtatt caacatttcc    9480
gtgtcgccct tattcccttt tttgcggcat tttgccttcc tgtttttgct cacccagaaa    9540
cgctggtgaa agtaaaagat gctgaagatc agttgggtgc acgagtgggt tacatcgaac    9600
tggatctcaa cagcggtaag atccttgaga gttttcgccc cgaagaacgt tttccaatga    9660
tgagcacttt taaagttctg ctatgtggcg cggtattatc ccgtattgac gccgggcaag    9720
agcaactcgg tcgccgcata cactattctc agaatgactt ggttgagtac tcaccagtca    9780
cagaaaagca tcttacggat ggcatgacag taagagaatt atgcagtgct gccataacca    9840
tgagtgataa cactgcggcc aacttacttc tgacaacgat cggaggaccg aaggagctaa    9900
ccgcttttttt gcacaacatg ggggatcatg taactcgcct tgatcgttgg gaaccggagc    9960
tgaatgaagc cataccaaac gacgagcgtg acaccacgat gcctgtagca atggcaacaa   10020
cgttgcgcaa actattaact ggcgaactac ttactctagc ttcccggcaa caattaatag   10080
actggatgga ggcggataaa gttgcaggac cacttctgcg ctcggccctt ccggctggct   10140
ggtttattgc tgataaatct ggagccggtg agcgtgggtc tcgcggtatc attgcagcac   10200
tggggccaga tggtaagccc tcccgtatcg tagttatcta cacgacgggg agtcaggcaa   10260
ctatggatga acgaaataga cagatcgctg agataggtgc ctcactgatt aagcattggt   10320
aactgtcaga ccaagtttac tcatatatac tttagattga tttaaaactt catttttaat   10380
ttaaaaggat ctaggtgaag atcctttttg ataatctcat gaccaaaatc ccttaacgtg   10440
agttttcgtt ccactgagcg tcagaccccg tagaaaagat caaaggatct tcttgagatc   10500
cttttttttct gcgcgtaatc tgctgcttgc aaacaaaaaa accaccgcta ccagcggtgg   10560
tttgtttgcc ggatcaagag ctaccaactc tttttccgaa ggtaactggc ttcagcagag   10620
cgcagatacc aaatactgtc cttctagtgt agccgtagtt aggccaccac ttcaagaact   10680
ctgtagcacc gcctacatac ctcgctctgc taatcctgtt accagtggct gctgccagtg   10740
gcgataagtc gtgtcttacc gggttggact caagacgata gttaccggat aaggcgcagc   10800
ggtcgggctg aacggggggt tcgtgcacac agcccagctt ggagcgaacg acctacaccg   10860
aactgagata cctacagcgt gagctatgag aaagcgccac gcttcccgaa gggagaaagg   10920
cggacaggta tccggtaagc ggcagggtcg gaacaggaga gcgcacgagg gagcttccag   10980
ggggaaacgc ctggtatctt tatagtcctg tcgggtttcg ccacctctga cttgagcgtc   11040
gatttttgtg atgctcgtca gggggcgga gcctatggaa aaacgccagc aacgcggcct   11100
ttttacggtt cctggccttt tgctggcctt ttgctcacat gttctttcct gcgttatccc   11160
ctgattctgt ggataaccgt attaccgcct ttgagtgagc tgataccgct cgccgcagcc   11220
```
gaacgaccga gcgcagcgag tcagtgagcg aggaagcgga aga          11263

<210> SEQ ID NO 7
<211> LENGTH: 4101
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Cas9 gene codon optimized for Nannochloropsis

<400> SEQUENCE: 7

```
gacaagaagt actccatcgg gctggacatc gggacgaact ccgtgggatg ggccgtgatc      60
acagacgaat acaaggtgcc ttccaagaag ttcaaggtgc tggggaacac ggacagacac     120
tccatcaaga agaacctcat cggggccttg ctcttcgact ccggagaaac cgccgaagca     180
acgcgattga aagaaccgc cagaagacga tacacgac ggaagaaccg catctgctac        240
ctccaggaga tcttcagcaa cgagatggcc aaggtggacg actcgttctt tcatcgcctg     300
gaggagagct tcctggtgga ggaagacaag aaacatgagc gccacccgat cttcgggaac     360
atcgtggacg aagtggccta ccacgagaaa taccccacga tctaccactt gcgcaagaaa     420
ctcgtggact ccacggacaa agcggacttg cggttgatct acttggcctt ggcccacatg     480
atcaaatttc ggggccactt cctgatcgag ggcgacttga atcccgacaa ttccgacgtg     540
gacaagctct tcatccagct ggtgcagacc tacaaccagc tcttcgagga accccatc      600
aatgcctccg gagtggacgc caaagccatc ttgtccgccc gattgtccaa atccagacgc     660
ttggagaact tgatcgcaca acttcctggc gagaagaaga cggcctctct cggcaacttg     720
atcgcgctgt cgctgggatt gacgcctaac ttcaagtcca acttcgactt ggccgaggac     780
gccaagttgc aactgtccaa ggacacctac gacgacgacc tcgacaacct gctggcccaa     840
attggcgacc aatacgcgga cttgtttttg gcggccaaga acttgagcga cgccatcttg     900
ttgagcgaca tcttgcgcgt gaatacggag atcaccaaag ccctttgtc cgcctctatg      960
atcaagcggt acgacgagca ccaccaagac ttgaccctgt tgaaagccct cgtgcggcaa    1020
caattgcccg agaagtacaa ggagatcttc ttcgaccagt ccaagaacgg gtacgccggc    1080
tacatcgacg gaggagcctc ccaagaagag ttctacaagt tcatcaagcc catcctggag    1140
aagatggacg gcaccgagga gttgctcgtg aagctgaacc gcgaagactt gttgcgaaaa    1200
cagcggacgt tcgacaatgg cagcatcccc caccaaatcc atttgggaga gttgcacgcc    1260
atcttgcgac ggcaagagga cttctacccg ttcctgaagg acaaccgcga gaaaatcgag    1320
aagatcctga cgttcagaat cccctactac gtgggaccct tggcccgagg caattcccgg    1380
tttgcatgga tgacgcgcaa aagcgaagag acgatcaccc cctggaactt cgaagaagtg    1440
gtcgacaaag gagcatccgc acagagcttc atcgagcgaa tgacgaactt cgacaagaac    1500
ctgcccaacg agaaggtgtt gcccaagcat tcgctgctgt acgagtactt cacggtgtac    1560
aacgagctga ccaaggtgaa gtacgtgacc gagggcatgc gcaaacccgc gttcctgtcg    1620
ggagagcaaa agaaggccat tgtggacctg ctgttcaaga ccaaccggaa ggtgaccgtg    1680
aaacagctga agaggacta cttcaagaag atcgagtgct tcgactccgt ggagatctcc    1740
ggcgtggagg accgattcaa tgcctccttg gaacctacc atgacctcct gaagatcatc    1800
aaggacaagg acttcctgga caacgaggag aacgaggaca tcctggagga catcgtgctg    1860
accctgaccc tgttcgagga ccgagagatg atcgaggaac ggttgaaaac gtacgcccac    1920
```

-continued

```
ttgttcgacg acaaggtgat gaagcagctg aaacgccgcc gctacaccgg atggggacga   1980
ttgagccgca aactgattaa tggaattcgc gacaagcaat ccggaaagac catcctggac   2040
ttcctgaagt ccgacgggtt cgccaaccgc aacttcatgc agctcatcca cgacgactcc   2100
ttgaccttca aggaggacat ccagaaggcc caagtgtccg acaaggaga ctccttgcac    2160 gagcacatcg ccaatttggc cggatccccc gcaatcaaaa aaggcatctt gcaaaccgtg   2220
aaagtggtcg acgaactggt gaaggtgatg ggacggcaca agcccgagaa catcgtgatc   2280
gaaatggccc gcgagaacca aaccacccaa aaaggacaga gaactcccg agagcgcatg    2340 aagcggatcg aagagggcat caaggagttg ggctcccaga tcctgaagga gcatcccgtg   2400
gagaataccc aattgcaaaa cgagaagctc tacctctact acctccagaa cgggcgggac   2460
atgtacgtcg accaagagct ggacatcaac cgcctctccg actacgatgt ggatcatatt   2520
gtgccccaga gcttcctcaa ggacgacagc atcgacaaca aggtcctgac gcgcagcgac   2580
aagaaccggg gcaagtctga caatgtgcct tccgaagaag tcgtgaagaa gatgaagaac   2640
tactggcggc agctgctcaa cgccaagctc atcacccaac ggaagttcga caacctgacc   2700
aaggccgaga gaggaggatt gtccgagttg acaaagccg gcttcattaa cgccaactc    2760 gtggagaccc gccagatcac gaagcacgtg gcccaaatct tggactccg gatgaacacg    2820 aaatacgacg agaatgacaa gctgatccgc gaggtgaagg tgatcacgct gaagtccaag   2880
ctggtgagcg acttccggaa ggacttccag ttctacaagg tgcgggagat caacaactac   2940
catcacgccc atgacgccta cctgaacgcc gtggtcggaa ccgccctgat caagaaatac   3000
cccaagctgg agtccgaatt cgtgtacgga gattacaagg tctacgacgt gcggaagatg   3060
atcgcgaagt ccgagcagga gatcggcaaa gccaccgcca agtacttctt ttactccaac   3120
atcatgaact tcttcaagac cgagatcacg ctcgccaacg gcgagatccg caagcgcccc   3180
ctgatcgaga ccaacggcga gacgggagag attgtgtggg acaaaggaag agattttgcc   3240
acagtgcgca aggtgctgtc catgcctcag gtgaacatcg tgaagaagac cgaggtgcaa   3300
acaggagggt tttccaaaga gtccatttttg cctaagagga attccgacaa gctcatcgcc   3360
cgcaagaagg actgggaccc caagaagtac gggggcttcg actcccccac ggtggcctac   3420
tccgtgttgg tggtggccaa agtggagaaa gggaagagca agaagctgaa atccgtgaag   3480
gagttgctcg gaatcacgat catggaacga tcgtcgttcg agaaaaaccc catcgacttc   3540
ctcgaagcca agggtacaa agaggtgaag aaggacctga tcatcaagct gcccaagtac   3600
tccctgttcg agctggagaa cggccgcaag cggatgctgg cctccgccgg gaactgcag    3660 aaagggaacg aattggcctt gcccctccaaa tacgtgaact tcctctactt ggcctcccat   3720
tacgaaaagc tcaaaggatc ccctgaggac aatgagcaga gcaactctt cgtggaacaa   3780 cacaagcact acctggacga gatcatcgag cagatcagcg agttctccaa gcgcgtgatc   3840
ctcgccgacg ccaacctgga caaggtgctc tccgcctaca acaagcaccg cgacaagcct   3900
atccgcgagc aagccgagaa tatcattcac ctgtttaccc tgacgaattt gggagcccct   3960
gccgccttta aatactttga caccaccatc gaccgcaaaa gatacacctc caccaaggaa   4020
gtcttggacg ccaccctcat ccaccagtcc atcacgggcc tctacgagac gcgcatcgac   4080
ctctcccaat gggcggcga c                                            4101
```

<210> SEQ ID NO 8
<211> LENGTH: 24
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: encodes Nuclear localization sequence

<400> SEQUENCE: 8
cccaagaaaa agcggaaggt cggc                                            24

<210> SEQ ID NO 9
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: encodes FLAG tag

<400> SEQUENCE: 9
gactacaagg atgacgatga caag                                            24

<210> SEQ ID NO 10
<211> LENGTH: 147
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: encodes Nuclear localization sequence-peptide
      linker-FLAG tag

<400> SEQUENCE: 10
atgcccaaga aaaagcggaa ggtcggcgac tacaaggatg acgatgacaa gttggagcct     60
ggagagaagc cctacaaatg ccctgagtgc ggaaagagct cagccaatc tggagccttg     120 acccggcatc aacgaacgca tacacga                                        147

<210> SEQ ID NO 11
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: RPL24 promoter

<400> SEQUENCE: 11
aataagcata catcatatga atacaattca gcttaaattt atcatacaaa gatgtaagtg     60
cagcgtgggt ctgtaacgat cgggcgtaat ttaagataat gcgagggacc ggggaggtt    120 ttggaacgga atgaggaatg ggtcatggcc cataataata atatgggttt ggtcgcctcg    180
cacagcaacc gtacgtgcga aaaggaaca gatccattta ataagttgaa cgttattctt    240
tcctatgcaa tgcgtgtatc ggaggcgaga gcaagtcata ggtggctgcg cacaataatt    300
gagtctcagc tgagcgccgt ccgcgggtgg tgtgagtggt catcctcctc ccggcctatc    360
gctcacatcg cctctcaatg gtggtggtgg ggcctgatat gacctcaatg ccgacccata    420
ttaaaaccca gtaaagcatt caccaacgaa cgagggctc ttttgtgtgt gttttgagta    480
tgattttaca cctctttgtg catctctctg gtcttccttg gttccgtag tttgggcatc    540 atcactcacg cttccctcga ccttcgttct tcctttacaa cccgacaca ggtcagagtt     600 ggagtaatca aaaagggt gcacgaatga gatacattag attttgacag atatcctttt     660
```

```
actggagagg gttcaaggga tcaaatgaac agcgggcgtt ggcaatctag ggagggatcg      720
gaggttggca gcgagcgaaa gcgtgtccat ccttttggct gtcacacctc acgaaccaac      780
tgttagcagg ccagcacaga tgacatacga gaatctttat tatatcgtag accttatgtg      840
gatgaccttt ggtgctgtgt gtctggcaat gaacctgaag gcttgatagg gaggtggctc      900
ccgtaaaccc tttgtccttt ccacgctgag tctcccccgc actgtccttt atacaaattg      960
ttacagtcat ctgcaggcgg ttttctttg gcaggcaaag                            1000
```

```
<210> SEQ ID NO 12
<211> LENGTH: 317
<212> TYPE: DNA
<213> ORGANISM: Nannochloropsis gaditana
<220> FEATURE:
<221> NAME/KEY: misc_feature
<223> OTHER INFORMATION: Bidirectional terminator 2

<400> SEQUENCE: 12
```

```
agtgatgcgg cctttaggaa acaccacaaa agtaattgac aatctcagga acgatctgcg       60
tgtttacagc ttcccaaata acaattatac cacgtaccaa aaggggttta atgtatctca      120
caaattcttc taataggtac agcttctcaa attgggtgta tgatgtgaca cttcgtctca      180
cacacgtcac gataattcag cgtatggctt cccttcatca cattcacgca aacttctaca      240
caaccctggg catatttctt gtgttggcaa cactcccgaa atcgattctg cacacaatgg      300
ttcattcaat gattcaa                                                    317
```

```
<210> SEQ ID NO 13
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: blasticidin S deaminase gene from Aspergillus
      terreus codon optimized for N. gaditana

<400> SEQUENCE: 13
```

```
atggccaagc ctttatccca agaggaatcc acgctgatcg aacgtgcaac tgcgaccatc       60
aacagcatac ctattagcga ggactactcg gtggccagtg cagccctctc gtccgacggt      120
cggatcttta ccggcgtgaa tgtatatcat ttcaccggag ggccatgcgc ggagctcgtg      180
gtcctcggaa cggccgctgc ggctgctgcc ggaaatctga cgtgcatagt ggccatcggg      240
aacgaaaacc gcggcattct gtctccgtgc gggcgatgtc ggcaggtgct gcttgacttg      300
cacccgggga tcaaggcaat tgtcaaagat tccgatgggc agcccacagc ggttggcatc      360
agggagttgc ttccctctgg ctacgtctgg gagggttga                             399
```

```
<210> SEQ ID NO 14
<211> LENGTH: 999
<212> TYPE: DNA
<213> ORGANISM: Nannochloropsis gaditana
<220> FEATURE:
<221> NAME/KEY: misc_feature
<223> OTHER INFORMATION: TCTP promoter

<400> SEQUENCE: 14
```

```
cgtgcaggtg tacagattga aggaaacaat ggagatatct ttggcagttg aaaaccgtgt       60
tcgaatcatg cttttctact ctccaactga gacgaaattt atagcgccat gtcgcttctg      120 actaccagge ttaggaaggc ctcatcacaa gctggatcgg ttcgaattaa gcaggcactg      180
```

```
aagccaagct tgcaagacag ccaccttta attccctcaa aacactttct caattcagcc    240
cggtaaatat gccgattcac agcggccaag atagagggga ggttagcaag aatgttgcga    300
tccctcccca gtcgttgcct cgcacacaac ctaggccttc acctttccat ggaaaattga    360
gaagtgaata ttggttttct tacggcatat cagatgaaat catgacccct aaacatgaag    420
agctgcaggc aaaacacctg ctctggacga gcacgatgaa atctcgagaa cccgccgtac    480
ttcagttgat cccgcatgat gacggccgcc attgaaataa gccacctcac tttattctag    540
caccgatttc caccgttgtg agggccgaac gaggacaatt tcgtgcgaaa caagcacgaa    600
cacgcacacg attagtagta cagacgagca gatcgatggc atgcggcacg gtctcgcgtt    660
ctcggcgacc aggacaacgg agcagaggga ggcctgccga gttccgaggg gcattttagt    720
ccaaaattgt gttgacacgt gaacaagtgg cttgaaaaga ggaaggaaat gcctgggttt    780
cccttcgaga gcgggaactc gcttgtgcgt catcctagct acccatggtc cctttgtggg    840
ggaggctgtt tcgtcctacc gaatgtgtgg cgctccatgc atcttctgcc tcccaaacca    900
ccaacatgag cacgcgaagg aaggagaaaa aagtggccgc aacgttctct tctcatattt    960
attgtctcat cacaaacata ggtacataat acaacaatc                            999

<210> SEQ ID NO 15
<211> LENGTH: 318
<212> TYPE: DNA
<213> ORGANISM: Nannochloropsis gaditana
<220> FEATURE:
<221> NAME/KEY: misc_feature
<223> OTHER INFORMATION: EIF3 terminator

<400> SEQUENCE: 15
ggcactgtaa ccccggttcc gctcgacgaa ggctgggagc gcccctttcgg tgggataaaa    60 tggatgcttt accgctgcgc ttcggctgag gaagagagaa atgcgagcgg ggatcggggt   120
cctagaaacg aagaaggag aacaagttcc tggccaaaga aaaacaagac aaataccctc    180
tccaggcctg ggcccattac tttttttgc tgtttcttat acctgcactc gtgcttctct    240
agtctgtcga gaccttacct gatcttcctc cctccatcgc tccccgcccc ccccatccga    300
gcaaccgtcg accatacg                                                   318

<210> SEQ ID NO 16
<211> LENGTH: 702
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Turbo GFP gene codon optimized for
      Nannochloropsis

<400> SEQUENCE: 16
atgttggaga gcgacgagag cggcctgccc gccatggaga tcgagtgccg catcaccggc    60
accctgaacg gcgtggagtt cgagctggtg ggcggcggag agggcacccc cgagcagggc   120
cgcatgacca caagatgaa gagcaccaaa ggcgccctga ccttcagccc ctacctgctg   180
agccacgtga tgggctacgg cttctaccac ttcggcacct accccagcgg ctacgagaac   240
cccttcctgc acgccatcaa caacggcggc tacaccaaca cccgcatcga gaagtacgag   300
gacggcggcg tgctgcacgt gagcttcagc taccgctacg aggccggccg cgtgatcggc   360
gacttcaagg tgatgggcac cggcttcccc gaggacagcg tgatcttcac cgacaagatc   420
```

```
atccgcagca acgccaccgt ggagcacctg cacccccatgg gcgataacga tctggatggc    480
agcttcaccc gcaccttcag cctgcgcgac ggcggctact acagctccgt ggtggacagc    540
cacatgcact tcaagagcgc catccacccc agcatcctgc agaacggggg ccccatgttc    600
gccttccgcc gcgtggagga ggatcacagc aacaccgagc tgggcatcgt ggagtaccag    660
cacgccttca agaccccgga tgcagatgcc ggtgaagaat aa                       702
```

```
<210> SEQ ID NO 17
<211> LENGTH: 822
<212> TYPE: DNA
<213> ORGANISM: Nannochloropsis gaditana
<220> FEATURE:
<221> NAME/KEY: misc_feature
<223> OTHER INFORMATION: 4A-III promoter

<400> SEQUENCE: 17
```

```
ggcataaagg acggcaagga aagaaaagaa agaaagaaaa ggacacttat agcatagttt     60
gaagttataa gtagtcgcaa tctgtgtgca gccgacagat gctttttttt tccgtttggc    120
aggaggtgta gggatgtcga agaccagtcc agctagtatc tatcctacaa gtcaatcatg    180
ctgcgacaaa aatttctcgc acgaggcctc tcgataaaca aaactttaaa agcacacttc    240
attgtcatgc agagtaataa ctcttccgcg tcgatcaatt tatcaatctc tatcatttcc    300 gccccttttcc ttgcatagag caagaaaagc gacccggatg aggataacat gtcctgcgcc    360
agtagtgtgg cattgcctgt ctctcattta cacgtactga agcataatg cacgcgcata    420 ccaatatttt tcgtgtacgg agatgaagag acgcgacacg taagatcacg agaaggcgag    480
cacggttgcc aatggcagac gcgctagtct ccattatcgc gttgttcggt agcttgctgc    540
atgtcttcag tggcactata tccactctgc ctcgtcttct acacgagggc cacatcggtg    600
caagttcgaa aaatcatatc tcaatcttca gatcctttcc agaaacggtg ctcaggcggg    660
aaagtgaagg ttttctactc tagtggctac cccaattctc tccgactgtc gcagacggtc    720
cttcgttgcg cacgcaccgc gcactacctc tgaaattcga caaccgaagt tcaattttac    780
atctaacttc tttcccattc tctcaccaaa agcctagctt ac                       822
```

```
<210> SEQ ID NO 18
<211> LENGTH: 200
<212> TYPE: DNA
<213> ORGANISM: Nannochloropsis gaditana
<220> FEATURE:
<221> NAME/KEY: misc_feature
<223> OTHER INFORMATION: Bidirectional terminator 5

<400> SEQUENCE: 18
```

```
gggtgggaag gagtcgggga gggtcctggc agagcggcgt cctcatgatg tgttggagac     60
ctggagagtc gagagcttcc tcgtcacctg attgtcatgt gtgtataggt taaggggcc    120 cactcaaagc cataaagacg aacacaaaca ctaatctcaa caaagtctac tagcatgccg    180
tctgtccatc tttatttcct                                              200
```

```
<210> SEQ ID NO 19
<211> LENGTH: 1029
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Hyg resistance gene
```

<400> SEQUENCE: 19

```
atggggaaga aaccggaact gaccgctacg tccgtggaga aattccttat tgagaagttc      60
gactctgtct ccgacttgat gcaactgagc gagggagagg agagtagggc gttctcgttt     120
gacgtagggg gtcggggata cgtgttgagg gttaatagtt gtgcggacgg gttctacaag     180
gatcggtatg tctaccgtca tttcgcctcc gccgctctcc ccataccaga ggtactggac     240
attggggagt ttagcgaatc tctcacgtac tgcatctcgc gccgagccca gggagtgacg     300
ttgcaagatc tgcccgaaac tgaattgcct gccgttttgc aacccgtggc cgaggccatg     360
gacgcgatcg ctgccgcaga tctgtctcag acgtccggct ttggaccttt tgggccccag     420
ggcatcgggc agtacacgac ctggcgagac ttcatctgcg ccattgccga tcctcacgtc     480
tatcattggc agacagtcat ggatgacacc gtgtctgcat ccgtggccca agcactggac     540
gaactcatgt tgtgggccga ggattgccct gaggtcaggc acctggtgca cgcggatttc     600
ggcagcaata acgtacttac agacaatggt cggattactg ctgtcatcga ctggtccgaa     660
gcgatgtttg gtgatagcca atacgaagtg gcgaacatat tcttctggcg tccctggttg     720
gcgtgcatgg agcagcagac acgctacttt gaacggaggc acccgagct ggccggctcc      780
ccacgactcc gcgcctatat tgttgcgtatc ggactcgatc agctttacca gtctctcgtc    840
gacggcaact tcgacgacgc cgcgtgggcg cagggccgct cgacgcgat agtccgcagc      900
ggggctggga cggtgggtcg gacccaaatc gcacgccggt cggctgcggt gtggacagac    960
ggctgtgttg aggtgcttgc ggactcgggc aaccgtaggc cgagcacccg accgcgtgca   1020
aaggagtga                                                          1029
```

<210> SEQ ID NO 20
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: EIF3 promoter

<400> SEQUENCE: 20

```
tcataatcaa agatgagcca gccacgaagc taccggagaa ttctgtaaga aaaatgttta      60
aagttgaaaa tgctaacagt gaagtgatat cctttttaa tggagtgttg aggtgaagtc     120
tagcatcgta ggggaaaaca ggattctgtg tcttccattc tactccttga taaagcgaag    180
aaatccgaca aaaccaaaga gattgttcaa gtttaagatt tgtaagcgta caactatgaa    240
cttcttctct ttgtaggcct gagtggtcgt atgcatacga ttcatgaagt gaatcagtat    300
cgctggatttt gcttaggag taaagcacaa ctaagaaaat atgctgcctg gcaggcatcc    360
tgagacatga ggcaagcgac gtagcaattg aatcctaatt taagccaggg catctgtatg    420
actctgttag ttaattgatg aaccaatgag ctttaaaaa aaatcgttgc gcgtaatgta     480
gttttaattc tccgccttga ggtgcggggc catttcggac aaggttcttt ggacggagat    540
ggcagcatgt gtcccttctc caaattggtc cgtgtggtag ttgagatgct gccttaaaat    600
tctgctcggt catcctgcct tcgcattcac tcctttcgag ctgtcgggtt cctcacgagg    660
cctccgggag cggattgcgc agaaaggcga cccggagaca cagagaccat acaccgacta    720
aattgcactg gacgatacgg catggcgacg acgatggcca agcattgcta cgtgattatt    780
cgccttgtca ttcagggaga aatgatgaca tgtgtggac ggtctttaca tgggaagagg     840
gcatgaaaat aacatggcct ggcgggatgg agcgtcacac ctgtgtatgc gttcgatcca    900
```

```
caagcaactc accatttgcg tcggggcctg tctccaatct gctttaggct acttttctct    960
aatttagcct attctataca gacagagaca cacagggatc                         1000

<210> SEQ ID NO 21
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 27 nucleotide 5' ID sequence

<400> SEQUENCE: 21
tccacagccc gaacccatga gagagaa                                         27

<210> SEQ ID NO 22
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 27 nucleotide 3' ID sequence

<400> SEQUENCE: 22
gcccgaatcg agttgatggc ccgcaaa                                         27

<210> SEQ ID NO 23
<211> LENGTH: 2400
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: HygR cassette with flanking ID sequences

<400> SEQUENCE: 23
tccacagccc gaacccatga gagagaatca taatcaaaga tgagccagcc acgaagctac     60
cggagaattc tgtaagaaaa atgtttaaag ttgaaaatgc taacagtgaa gtgatatcct    120
tttttaatgg agtgttgagg tgaagtctag catcgtaggg gaaaacagga ttctgtgtct    180
tccattctac tccttgataa agcgaagaaa tccgacaaaa ccaaagagat tgttcaagtt    240
taagatttgt aagcgtacaa ctatgaactt cttctctttg taggcctgag tggtcgtatg    300
catacgattc atgaagtgaa tcagtatcgc tggattttgc ttaggagtaa agcacaacta    360
agaaaatatg ctgcctggca ggcatcctga gacatgaggc aagcgacgta gcaattgaat    420
cctaatttaa gccagggcat ctgtatgact ctgttagtta attgatgaac caatgagctt    480
taaaaaaaaa tcgttgcgcg taatgtagtt ttaattctcc gccttgaggt gcggggccat    540
ttcggacaag gttctttgga cggagatggc agcatgtgtc ccttctccaa attggtccgt    600
gtggtagttg agatgctgcc ttaaaattct gctcggtcat cctgccttcg cattcactcc    660
tttcgagctg tcgggttcct cacgaggcct ccggagcgg attgcgcaga aaggcgaccc    720
ggagacacag agaccataca ccgactaaat tgcactggac gatacggcat ggcgacgacg    780
atggccaagc attgctacgt gattattcgc cttgtcattc agggagaaat gatgacatgt    840
gtgggacggt ctttacatgg aagagggca tgaaaataac atggcctggc gggatggagc    900
gtcacacctg tgtatgcgtt cgatccacaa gcaactcacc atttgcgtcg gggcctgtct    960
```

```
ccaatctgct ttaggctact tttctctaat ttagcctatt ctatacagac agagacacac    1020
agggatcatg gggaagaaac cggaactgac cgctacgtcc gtggagaaat tccttattga    1080
gaagttcgac tctgtctccg acttgatgca actgagcgag ggagaggaga gtagggcgtt    1140
ctcgtttgac gtaggggtc ggggatacgt gttgagggtt aatagttgtg cggacgggtt     1200
ctacaaggat cggtatgtct accgtcattt cgcctccgcc gctctcccca taccagaggt    1260
actggacatt gggagttta gcgaatctct cacgtactgc atctcgcgcc gagcccaggg     1320
agtgacgttg caagatctgc ccgaaactga attgcctgcc gttttgcaac ccgtggccga    1380
ggccatggac gcgatcgctg ccgcagatct gtctcagacg tccggctttg accttttgg    1440 gccccagggc atcgggcagt acacgacctg gcgagacttc atctgcgcca ttgccgatcc    1500
tcacgtctat cattggcaga cagtcatgga tgacaccgtg tctgcatccg tggcccaagc    1560
actggacgaa ctcatgttgt gggccgagga ttgccctgag gtcaggcacc tggtgcacgc    1620
ggatttcggc agcaataacg tacttacaga caatggtcgg attactgctg tcatcgactg    1680
gtccgaagcg atgtttggtg atagccaata cgaagtggcg aacatattct tctggcgtcc    1740
ctggttggcg tgcatggagc agcagacacg ctactttgaa cggaggcacc cggagctggc    1800
cggctcccca cgactccgcg cctatatgtt gcgtatcgga ctcgatcagc tttaccagtc    1860
tctcgtcgac ggcaacttcg acgacgccgc gtgggcgcag ggccgctgcg acgcgatagt    1920
ccgcagcggg gctgggacgg tgggtcggac ccaaatcgca cgccggtcgg ctgcggtgtg    1980
gacagacggc tgtgttgagg tgcttgcgga ctcgggcaac cgtaggccga gcacccgacc    2040
gcgtgcaaag gagtgattga atcattgaat gaaccattgt gtgcagaatc gatttcggga    2100
gtgttgccaa cacaagaaat atgcccaggg ttgtgtagaa gtttgcgtga atgtgatgaa    2160
gggaagccat acgctgaatt atcgtgacgt gtgtgagacg aagtgtcaca tcatacaccc    2220
aatttgagaa gctgtaccta ttagaagaat ttgtgagata cattaaaccc cttttggtac    2280
gtggtataat tgttatttgg gaagctgtaa acacgcagat cgttcctgag attgtcaatt    2340
acttttgtgg tgtttcctaa aggccgcatc actgcccgaa tcgagttgat ggcccgcaaa    2400
```

<210> SEQ ID NO 24
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer to detect insertion of the donor
      fragment into the targeted locus of Naga_100148g8

<400> SEQUENCE: 24
accctgtcgc acatcctcct                                                 20

<210> SEQ ID NO 25
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse primer to detect insertion of the donor
      fragment into the targeted locus of Naga_100148g8

-continued

```
<400> SEQUENCE: 25
ttctgaagac cgtggtccca gc                                               22
```

US 11,124,798 B2

ALGAL LIPID PRODUCTIVITY VIA GENETIC MODIFICATION OF A TPR DOMAIN CONTAINING PROTEIN

CROSS-REFERENCE TO RELATED APPLICATIONS

This application claims benefit of priority under 35 U.S.C. § 119(e) of U.S. Ser. No. 62/596,671, filed Dec. 8, 2017, the entire contents of which are incorporated herein by reference in their entireties.

INCORPORATION BY REFERENCE OF SEQUENCE LISTING

The material in the accompanying sequence listing is hereby incorporated by reference into the application. The accompanying sequence listing text file, name SGI2130_1_Sequence_Listing.txt, was created on Nov. 19, 2018, and is 54 kb. The file can be accessed using Microsoft Word on a computer that uses Window OS.

FIELD OF THE INVENTION

The invention relates to mutant microorganisms, such as algae and heterokonts, having increased lipid productivity and methods of their use in producing lipids.

BACKGROUND OF THE INVENTION

Various attempts to improve lipid productivity by increasing lipid biosynthesis have focused on manipulating genes encoding enzymes for nitrogen assimilation or lipid metabolism as well as genes encoding polypeptides involved in lipid storage. For example, US2014/0162330 discloses a *Phaeodactylum tricornutum* strain in which the nitrate reductase (NR) gene has been attenuated by RNAi-based knockdown; Trentacoste et al. ((2013) *Proc. Natl. Acad. Sci. USA* 110: 19748-19753) disclose diatoms transformed with an RNAi construct targeting the Thaps3_264297 gene predicted to be involved in lipid catabolism; and WO2011127118 discloses transformation of *Chlamydomonas* with genes encoding oleosins (lipid storage proteins) or with genes encoding diacylglycerol transferase (DGAT) genes. Although in each case increased lipid production was asserted based on microscopy or staining with lipophilic dyes, no quantitation of lipid production by the manipulated cells was provided, nor was the relationship between biomass and lipid productivities over time determined.

Daboussi et al. 2014 (*Nature Comm.* 5:3881) report that disruption of the UGPase gene in *Phaeodactylum triconornutum*, which is believed to provide precursors to laminarin (a storage carbohydrate) synthesis, results in increased lipid accumulation. However, no biochemical data was shown to indicate that laminarin content was affected (or even present) and lipid and biomass productivities were not reported. Similarly, several groups have reported increases in lipid accumulation in *Chlamydomonas starchless* mutants (Wang et al. 2009 *Eukaryotic Cell* 8:1856-1868; Li et al. 2010 *Metab Eng.* 12:387-391) however, successive reports that actually measured lipid productivity concluded that these strains were impaired in growth when grown in phototrophic conditions (Siaut et al. 2011 *BMC Biotechnol.* 11:7; Davey et al. 2014 *Eukaryot Cell* 13:392-400). These reports concluded that the highest lipid productivities measured as triglycerides (TAG) produced per liter per day, were actually achieved by the wild-type parental strain.

WO 2011/097261 and US20120322157 report that a gene denoted "SN03" encoding an arresting protein has a role in increasing lipid production under nutrient replete conditions when overexpressed in *Chlamydomonas*. However, overexpression of the SN03 gene was observed to result in the appearance of unidentified polar lipids, which were not quantified, and did not result in an increase in TAG. Another polypeptide identified as potentially regulating stress-induced lipid biosynthesis has been described by Boyle et al. ((2012) *J. Biol. Chem.* 287:15811-15825). Knockout of the NRR1 gene in *Chlamydomonas* encoding a "SQUAMOUSA" domain polypeptide resulted in a reduction of lipid biosynthesis with respect to wild type cells under nitrogen depletion; however, no mutants were obtained demonstrating increased lipid production. US 2010/0255550 suggests the overexpression of putative transcription factors (TF1, TF2, TF3, TF4, and TF5) in algal cells to increase lipid production, but no such strains are disclosed.

US 2017/005803 discloses a ZyCys regulator gene whose attenuation results in increased lipid productivity in mutant algae when cultured in a medium that includes nitrate. The mutant algae demonstrated growth in culture, accumulating biomass at a rate at least 80% that of wild type cells while producing up to twice as much lipid as the wild type progenitor strain. US 2017/0121742 discloses mutant algae having attenuated expression of a gene encoding a polypeptide having a Bromo domain and a TAZ zinc finger domain that demonstrate elevated lipid productivity with minimal reduction in biomass productivity with respect to wild type algae.

SUMMARY OF THE DISCLOSURE

In one aspect, provided herein are mutant microorganisms having attenuated expression of a gene encoding a polypeptide that includes a tetratricopeptide repeat (TPR) domain that produce more lipid than a control microorganism and/or exhibit increased partitioning of carbon to lipid with respect to the control microorganism, such as when the mutant microorganism and the control microorganism are cultured under the same conditions. In some embodiments, the control microorganism is a wild-type microorganism. In some embodiments, the mutant microorganism produces at least about 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, or at least about 200% more fatty acid methyl ester-derivatizable lipids (FAME) than a control microorganism. In some embodiments, the culture conditions under which the mutant microorganism having attenuated expression of a gene encoding a polypeptide that includes a TPR domain produces more lipid than a control microorganism can be culture conditions under which both the mutant microorganism and control microorganism produce biomass. For example, the culture conditions can be nitrogen replete with respect to the control microorganism and can be nutrient replete with respect to the control microorganism.

In some embodiments, the mutant microorganisms provided herein exhibit a ratio of FAME to total organic carbon (TOC) that is at least about 20%, at least 30%, at least 40%, at least 50%, at least 60%, at least 70%, at least 80%, at least 90%, at least 100%, at least 120%, at least 140%, at least 160%, at least 180%, at least 200%, at least 220%, at least 240%, at least 260%, at least 280%, or at least 300% higher (e.g., 20-300% higher) than the FAME/TOC ratio of the control microorganism. In some embodiments, the culture conditions under which the mutant microorganism having attenuated expression of a gene encoding a polypeptide that includes a TPR domain has a higher FAME to TOC ratio than a control microorganism can be culture conditions under which both the mutant microorganism and control microorganism produce biomass. For example, the culture conditions can be nitrogen replete with respect to the control microorganism and can be nutrient replete with respect to the control microorganism.

"Attenuated expression" of a gene as set forth above includes, for example, reduced expression of the gene such that a reduced level (which may be an undetectable level) of a functional polypeptide encoded by the gene is produced. Attenuated expression also includes expression where a mutated (such as a deleted, truncated, or frame-shifted) polypeptide is produced, such that the mutated polypeptide has reduced or altered function with respect to the non-mutated polypeptide. Attenuated expression can be the result of mutation of the gene encoding the polypeptide, or can be the result of expression or delivery of a construct designed to reduced expression of the gene encoding the polypeptide, such as, for example, and RNAi construct targeting the gene.

In some embodiments, the mutant microorganisms are generated by classical mutagenesis or by genetic engineering techniques. In some embodiments, the mutant microorganism may have a mutation in a gene encoding a polypeptide that includes a GAF (e.g., GAF2) domain, or a gene affecting the expression thereof, that results in a decrease in the level of expression of the gene encoding a polypeptide that includes a GAF domain compared to the level of expression of the gene in a control microorganism. In some embodiments, the one or more mutations are generated using one or more agents that induce a double strand break. In some examples, the agent is a meganuclease, a zinc finger nuclease, a Transcription Activator-Like Effector Nuclease (TALEN) system, and/or a Cas nuclease. In some embodiments, a mutation that results in attenuated expression of a gene encoding a GAF domain is an insertional mutation.

In some embodiments, the mutant microorganism is any eukaryotic microorganism, and in illustrative embodiments, the mutant microorganism is a heterokont or alga. In some embodiments, the mutant microorganisms are generated by classical mutagenesis or by genetic engineering techniques. In some embodiments, the mutant microorganism has a mutation in a gene encoding a polypeptide that includes a TPR domain, or a gene affecting the expression thereof, that results in a decrease of expression of the gene encoding a polypeptide that includes a TPR domain compared to expression of the gene in a control microorganism. In some embodiments, the mutant microorganism has a mutation in a gene encoding a polypeptide that includes a TPR domain, that results in a truncated, internally deleted, and/or frame-shifted polypeptide having reduced or negligible activity. In some embodiments, the mutant microorganism has one or more point mutations that alter the amino acid sequence of the TPR domain-containing polypeptide, resulting in a polypeptide having reduced or negligible activity. Such point mutations can in some embodiments be in the TPR domain. In various embodiments, the one or more mutations are generated using one or more agents that induce a double strand break. In some examples, the agent is a meganuclease, a zinc finger nuclease, a Transcription Activator-Like Effector Nuclease (TALEN) system, and/or a Cas nuclease.

In some embodiments, the mutant microorganism is any eukaryotic microorganism, and in illustrative embodiments, the mutant microorganism is a heterokont or alga. In some example, the mutant microorganism is a heterokont alga such as a diatom or Eustigmatophyte species, and may be, for example, a species of a diatom genus such as *Amphiprora*, *Amphora*, *Chaetoceros*, *Cyclotella*, *Fragilaria*, *Fragilaropsis*, *Hantzschia*, *Navicula*, *Nitzschia*, *Phæodactylum*, *Phæodactylum*, *Phæodactylum*, *Skeletonema*, or *Thalassiosira*. In some examples, the mutant alga is a Eustigmatophyte, such as a Eustigmatophyte belonging to a genus such as *Chloridella*, *Chlorobptrys*, *Ellipsoidion*, *Eustigmatos*, *Goniochloris*, *Monodopsis*, *Monodus*, *Nannochloropsis*, *Pseudocharaciopsis*, *Pseudostaruastrum*, *Pseudotetraedriella*, and *Vischeria*.

Also provided herein is a biomass comprising a mutant as provided herein. Further provided is an extract of a mutant as provided herein. The extract can be a crude extract or a partially purified, purified, or refined extract that can include any combination of cellular components, including but not limited to membranes, lipids, proteins, carbohydrate, soluble molecules and insoluble molecules. For example the extract can optionally be an extract that has been subjected to one or more treatments such as but not limited to selective precipitation, high or low temperature treatment, filtration, or centrifugation.

Also included are methods of producing lipids using the mutant microorganisms disclosed herein. For example, a mutant microorganism as provided herein that has attenuated expression of a gene encoding a polypeptide that includes a TPR domain and produces more lipid than a control strain can be cultured in batch, semi-continuous, or continuous culture to produce one or more lipids. The methods can include isolating one or more lipids from the culture (e.g., from the cells, culture medium, or whole culture). The culture medium can be nitrogen replete or can be nitrogen-limited or nitrogen deplete during the lipid production period. In some embodiments, the medium used for culturing a mutant microorganism as provided herein to produce lipid can include nitrate as substantially the sole source of nitrogen. In some examples, the methods can include culturing an algal mutant as provided herein under photoautrophic conditions.

Also included are DNA molecules for expressing guide RNAs; guide RNAs that target a gene that encodes a TPR domain-containing protein that affects lipid production; and nucleic acid constructs for generating mutant microorganisms using genetic engineering techniques. A guide RNA that targets a TRP-containing gene, e.g., a gene having at least 60%, at least 65%, at least 70%, at least 75%, at least 80%, at least 85%, at least 90%, or at least 95% identity to SEQ ID NO:1 can have homology to a coding region of the gene that includes a TPR domain, or can have homology to a 5' UTR, 3' UTR, or region of a gene upstream of the 5'UTR.

These and other objects and features of this disclosure will become more fully apparent when the following detailed description is read in conjunction with the accompanying drawings.

DETAILED DESCRIPTION

Definitions

Figure 1:
FIG. 1 is a schematic depiction of the TPR-6029 protein encoded by *N. gaditana* gene at the Naga 100148g8 locus (SEQ ID NO:4 and SEQ ID NO:3 represent the gene and protein, respectively). The boxes denote the positions of the TPR domain (SEQ ID NO:1) and the DUF4470 domain (SEQ ID NO:2). Arrows point to the position targeted by CRISPR guide sequences to produce the knockout GE-15360. The figure is not to scale.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular.

All headings are for the convenience of the reader and do not limit the invention in any way. References to aspects or embodiments of the invention do not necessarily indicate that the described aspects may not be combined with other described aspects of the invention or features of other aspects of the invention. All publications, patents and other references mentioned herein are incorporated by reference in their entireties for all purposes as if each individual publication or patent application were specifically and individually indicated to be incorporated by reference.

The term "and/or" as used in a phrase such as "A and/or B" herein is intended to include "A and B", "A or B", "A", and "B".

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto. "Optional" or "optionally" means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination). Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. In addition, a range (e.g., 90-100%) is meant to include the range per se as well as each independent value within the range as if each value was individually listed. All ranges provided within the application are inclusive of the values of the upper and lower ends of the range unless specifically indicated otherwise. The term "combined" or "in combination" or "in conjunction" may refer to a physical combination of agents that are administered together or the use of two or more agents simultaneously with reference to, e.g., time and/or physicality.

Reference to properties that are "substantially the same" or "substantially identical" or "about" without further explanation of the intended meaning, is intended to mean the properties are within 10%, and preferably within 5%, and may be within 2.5%, of the reference value. Where the intended meaning of "substantially" in a particular context is not set forth, the term is used to include minor and irrelevant deviations that are not material to the characteristics considered important in the context of the subject matter of the invention.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, "gene" may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or for example between about 200 nucleotides and about 25,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids and other modified nucleic acids or nucleic acid analogs (e.g., Efimov and Chakhmakhcheva (2005) *Methods Mol Biol.* 288: 147-163)) or modified or non-naturally-occurring nucleobases. The nucleic acid molecules can be double-stranded, partially double stranded, or single-stranded; a single stranded nucleic acid molecule that comprises a gene or a portion thereof can be a coding (sense) strand or a non-coding (antisense) strand. Although a sequence of the nucleic acids may be shown in the form of DNA, a person of ordinary skill in the art recognizes that the corresponding RNA sequence will have a similar sequence with the thymine being replaced by uracil i.e. "t" with "u".

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source, which may be, for example, a species of organism. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other gene synthesis or molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least about 50%, at least 55%, at least 65%, at least 70%, at least 75%, at least 80%, at least 85%, at least 90%, at least 95%, at least 96%, at least 97%, at least 98%, or at least about 99% sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least about 85%, at least 90%, at least 95%, at least 96%, at least 97%, at least 98%, or at least about 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be substantially free of chemicals beyond buffer or solvent, for example. "Substantially free" is not intended to mean that other components beyond the novel nucleic acid molecules are undetectable.

The terms "naturally-occurring" and "wild type" refer to a form found in nature which is most frequently observed in a naturally occurring population and is thus arbitrarily designated as "wild-type". For example, a naturally occurring or wild type nucleic acid molecule, nucleotide sequence or protein may be present in and isolated from a natural source, and is not intentionally modified by human manipulation. "Wild-type" may also refer to the sequence at a specific nucleotide position or positions, or the sequence at a particular codon position or positions, or the sequence at a particular amino acid position or positions.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, truncation, frameshifting, or insertional mutation) that does not encode a complete functional open reading frame or that has decreased expression due to alteration or disruption of gene regulatory sequences. An attenuated gene may also be a gene targeted by a construct that reduces expression of the gene, such as, for example, an antisense RNA, microRNA, RNAi molecule, or ribozyme. Attenuated gene expression can be gene expression that is eliminated, for example, reduced to an amount that is insignificant or undetectable. Attenuated gene expression can also be gene expression that results in an RNA or protein that is not fully functional or nonfunctional, for example, attenuated gene expression can be gene expression that results in a truncated RNA and/or polypeptide.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene or nucleic acid molecule may be derived from a different species (and so "heterologous"), or from the same species (and so "homologous"), relative to the cell being transformed. An "endogenous" nucleic acid molecule, gene or protein is a native nucleic acid molecule, gene, or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. Thus, a "non-native" nucleic acid molecule is a nucleic molecule that is not naturally present in the host cell, for example, the non-native nucleic acid molecule is exogenous to the host cell or microorganism into which it is introduced, and may be heterologous with respect to the host cell or microorganism. Additionally, a nucleic acid sequence or amino acid sequence that has been removed from a cell, subjected to laboratory manipulation, and introduced or reintroduced into a host cell such that it differs in sequence or location in the genome with respect to its position in a non-manipulated organism (i.e., is juxtaposed with or operably linked to sequences it is not juxtaposed with or operably linked to in a non-transformed organism) is considered "non-native". Non-native genes also include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering regardless of whether the amino acid varies from that of a wild-type protein.

When applied to organisms, the term recombinant, engineered, or genetically engineered refers to organisms that have been manipulated by introduction of a heterologous or exogenous recombinant nucleic acid sequence into the organism (e.g., a non-native nucleic acid sequence), and includes gene knockouts, targeted mutations, gene replacement, and promoter replacement, deletion, disruption, or insertion, as well as introduction of transgenes or synthetic genes or nucleic acid sequences into the organism. That is, recombinant, engineered, or genetically engineered refers to organisms that have been altered by human intervention. Recombinant or genetically engineered organisms can also be organisms into which constructs for gene "knockdown" have been introduced. Such constructs include, but are not limited to, RNAi, microRNA, shRNA, siRNA, antisense, and ribozyme constructs. Also included are organisms whose genomes have been altered by the activity of meganucleases, zinc finger nucleases, TALENs, or Cas/CRISPR systems. An exogenous or recombinant nucleic acid molecule can be integrated into the recombinant/genetically engineered organism's genome or in other instances may not be integrated into the host genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes a minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. A promoter region can include, in addition to the gene-proximal promoter where RNA polymerase binds to initiate transcription, additional sequences upstream of the gene that can be within about 1 kb, about 2 kb, about 3 kb, about 4 kb, about 5 kb or more of the transcriptional start site of a gene, where the additional sequences can influence the rate of transcription of the downstream gene and optionally the responsiveness of the promoter to developmental, environmental, or biochemical (e.g., metabolic) conditions.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g., a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene and protein Accession numbers, commonly provided in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics. Gene loci identifiers refer to the published genome described in Corteggiani Carpinelli et al. (2014) *Mol Plant* 7:323-335 and available online on the CRIBI Genomics *Nannochloropsis* genome portal.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. For polypeptide sequences, N-terminal or C-terminal insertions or deletions shall not be construed as affecting homology, and internal deletions and/or insertions into the polypeptide sequence of less than about 65, less than about 60, less than about 50, less than about 40, less than about 30, less than about 20, or less than about 10 amino acid residues shall not be construed as affecting homology of compared amino acid (protein) sequences. For nucleic acid sequences, 5' end or 3' end insertions or deletions shall not be construed as affecting homology, and internal deletions and/or insertions into the polypeptide sequence of less than about 200, less than about 180, less than about 150, less than about 120, less than about 100, less than about 90, less than about 80, less than about 70, less than about 60, less than about 50, less than about 40, or less than about 30 nucleotides shall not be construed as affecting homology of compared nucleic acid sequences. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least about 50%, at least about 55%, of at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., at least any of 50%, 75% or 90%) sequence identity with the full-length polypeptide or nucleic acid sequence, or to fragments thereof comprising a consecutive sequence of at least about 100, at least about 125, at least about 150 (e.g., at least 100) or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" [of a gene product] includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination or targeted integration or mutation using a cas/CRISPR system to knockout a particular gene of interest. In still other embodiments, targeted insertion into or mutation of a gene regulatory region using a cas/CRISPR system, RNAi, or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, "mutant" refers to an organism that has a mutation in a gene that is the result of classical mutagenesis, for example, using gamma irradiation, UV, or chemical mutagens. "Mutant" as used herein also refers to a recombinant cell that has altered structure or expression of a gene as a result of genetic engineering that many include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, ribozymes, or the like; and genome engineering using meganucleases, zinc finger nucleases, TALENs, and/or CRISPR technologies, and the like. A mutant may also be produced by random or directed insertional mutagenesis by transforming an organism, tissue, or cells with a nucleic acid construct and/or by transposon mutagenesis. A mutant is therefore not a naturally-occurring organism. A mutant organism of interest will typically have a phenotype different than that of the corresponding wild type or progenitor strain that lacks the mutation, where the phenotype can be assessed by growth assays, product analysis, photosynthetic properties, biochemical assays, etc. When referring to a gene "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region, e.g., within about 1 kb, about 2 kb, or about 3 kb, about 4 kb, or about 5 kb of the translational start site. For example, a mutant having attenuated expression of a gene as disclosed herein can have a mutation, which can be one or more nucleobase changes and/or one or more nucleobase deletions and/or one or more nucleobase insertions, into the region of a gene 5' of the transcriptional start site, such as, in non-limiting examples, within 2 kb, within 1.5 kb, within 1 kb, or within 0.5 kb of the known or putative transcriptional start site, or within 3 kb, within 2.5 kb, within 2 kb, within 1.5 kb, within 1 kb, or within 0.5 kb of the translational start site. As nonlimiting examples, a mutant gene can be a gene that has a mutation, insertion, and/or deletion within the promoter region that can either increase or decrease expression of the gene; can be a gene that has a deletion that results in production of a nonfunctional protein, truncated protein, dominant negative protein, and/or no protein; and/or can be a gene that has one or more point mutations leading to a change in the amino acid of the encoded protein or results in aberrant splicing of the gene transcript, etc.

Conserved domains of polypeptides include those identified in the "cd" (conserved domain) database, the COG database, the SMART database, the PRK database, the TIGRFAM database, or others known the art. The National Center for Biotechnology Information website sponsored by the U.S. National Institutes of Health includes a conserved domain database (CDD) which it describes as "a protein annotation resource that consists of a collection of well-annotated multiple sequence alignment models for ancient domains and full-length proteins. These are available as position-specific score matrices (PSSMs) for fast identification of conserved domains in protein sequences via RPS-BLAST includes NCBI curated domains, which use information to explicitly define domain boundaries and provide insights into sequence/structure/function relationships, as well as domain models imported from a number of external sources (Pfam, SMART, COG, PRK, TIGRFAM)." Sequences can be searched for conserved domains at the cdd database of NCBI. See, Marchler-Bauer et al. (2015) *Nucleic Acids Res.* 43(D) 222-226.

The term "Pfam" refers to a large collection of protein domains and protein families maintained by the Pfam Consortium and available at several sponsored world wide web sites. The latest release of Pfam is Pfam 31.0 (March 2017). Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) *Nucleic Acids Research* 26, 263-266; Bateman (2004) *Nucleic Acids Research* 32, Database Issue, *D*138-*D*141; Finn (2006) *Nucleic Acids Research* Database Issue 34, D247-251; Finn (2010) *Nucleic Acids Research* Database Issue 38, D211-222). By accessing the Pfam database, for example, using any of the above-reference websites, protein sequences can be queried against the HMMs using HMMER homology search software (e.g., HMMER2, HMMER3, or a higher version, available online). Significant matches that identify a queried protein as being in a pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be double stranded, partially double stranded, or single stranded and can be, for example, the complement of the mRNA sequence. In preferred examples, a cDNA does not include one or more intron sequences that occur in the naturally-occurring gene that the cDNA corresponds to (i.e., the gene as it occurs in the genome of an organism). For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences multiple partial cDNAs.

A "control cell" or "control microorganism" is either a wild type cell or microorganism from which the mutant microorganism (genetically engineered or mutagenized microorganism) is directly or indirectly derived, or is a cell or microorganism that is substantially identical to the mutant cell or microorganism referred to (i.e., of the same genus and species, preferably of the same strain) with the exception that the control cell or microorganism does not have the mutation resulting in increased lipid production that the subject microorganism has. For example, where the mutant microorganism has attenuated expression of (1) a gene encoding a polypeptide that includes a TPR domain (e.g., SEQ ID NO:1 or SEQ ID NO:2); (2) a gene encoding a polypeptide that has a TPR domain having at least about 50%, at least 55%, at least 60%, at least 65%, at least 70%, at least 75%, at least 80%, at least 85%, at least 90%, or at least 95% identity to SEQ ID NO:1; (3) a gene encoding a polypeptide having at least 50%, at least 55%, at least 60%, at least 65%, at least 70%, at least 75%, at least 80%, at least 85%, at least 90%, or at least 95% identity to SEQ ID NO:2; or, (4) a gene encoding a polypeptide having at least about 50%, at least 55%, at least 60%, at least 65%, at least 70%, at least 75%, at least 80%, at least 85%, at least 90%, or at least 95% identity to SEQ ID NO:3; where the control cell can be substantially identical to the mutant microorganism with the exception that the control microorganism does not have attenuated expression of (1), (2), (3) or (4).

"The same conditions" or "the same culture conditions", as used herein, means substantially the same conditions, that is, any differences between the referenced conditions that may be present are minor and not relevant to the function or properties of the microorganism in a material way, including but not limited to lipid production or biomass production.

As used herein "lipid" or "lipids" refers to fats, waxes, fatty acids, fatty acid derivatives such as fatty alcohols, wax esters, alkanes, and alkenes, sterols, monoglycerides, diglycerides, triglycerides, phospholipids, sphingolipids, saccharolipids, and glycerolipids. "FAME lipids" or "FAME" refers to lipids having acyl moieties that can be derivatized to fatty acid methyl esters, such as, for example, monoacylglycerides, diacylglycerides, triacylglycerides (TAGs), wax esters, and membrane lipids such as phospholipids, galactolipids, etc.

In one example, lipid productivity can be assessed as FAME productivity in milligrams per liter (mg/L) and for algae, may be reported as grams per meter per day (g/m$^2$/day). In one example, the semi-continuous assays provided herein, mg/L values can be converted to g/m2/day by taking into account the area of incident irradiance (for example, the semicontinious process assay (SCPA) flask rack aperture may be 1½"×3⅜", or 0.003145 m$^2$) and the volume of the culture may be 550 ml. To obtain productivity values in g/m$^2$/day, mg/L values can be multiplied by the daily dilution rate (30%) and a conversion factor of 0.175. Where lipid or subcategories thereof (for example, TAG or FAME) are referred to as a percentage, the percentage is a weight percent unless indicated otherwise.

"Biomass" refers to cellular mass, whether of living or dead cells, and can be assessed in cultured cells, for example, as aspirated pellet weight, but is more preferably dry weight (e.g., lyophilate of a culture sample or pelleted cells), ash-free dry weight (AFDW), or total organic carbon (TOC), using methods known in the art. Biomass increases during the growth of a culture under growth permissive conditions and may be referred to as "biomass accumulation" in batch cultures, for example. In continuous or semi-continuous cultures that undergo steady or regular dilution, biomass that is produced that would otherwise accumulate in the culture is removed during culture dilution. Thus, daily biomass productivity (increases in biomass) by these cultures can also be referred to as "biomass accumulation". Biomass productivity can be assessed as TOC productivity in milligrams per liter (mg/L) and for algae, may be reported as grams per meter per day (g/m$^2$/day). In the semi-continuous assays provided herein, mg/L values are converted to g/m2/day by taking into account the area of incident irradiance (the SCPA flask rack aperture of 1½"× 3⅜", or 0.003145 m$^2$) and the volume of the culture (550 ml). To obtain productivity values in g/m$^2$/day, mg/L values are multiplied by the daily dilution rate (30%) and a conversion factor of 0.175. Where biomass is expressed as a percentage, the percentage is a weight percent unless indicated otherwise.

In the context of this disclosure, a "nitrogen source" is a source of nitrogen that can be taken up and metabolized by the subject microorganism and incorporated into biomolecules for growth and propagation. For example, compounds including nitrogen that cannot be taken up and/or metabolized by the microorganism for growth (e.g., nitrogen-containing biological buffers such as Hepes, Tris, etc.) are not considered nitrogen sources in the context of the invention.

"Reduced nitrogen", as used herein, is nitrogen in the chemical form of ammonium salt, ammonia, urea, amides, or an amino acid (e.g., an amino acid that can be taken up and metabolized by the microorganism being cultured to provide a source of nitrogen for incorporation into biomolecules, thereby supporting growth). Examples of amino acids that may be nitrogen sources can include, without limitation, glutamate, glutamine, histidine, proline, lysine, arginine, asparagine, alanine, and glycine. "Non-reduced nitrogen" in the context of a nitrogen source that can be present in a culture medium for microorganisms refers to nitrate or nitrite that must be reduced prior to assimilation into organic compounds by the microorganism.

"The sole source of nitrogen (in the culture medium)" is used interchangeably with "substantially the sole source of nitrogen" and indicates that no other nitrogen source that can be metabolized by the microorganism (i.e., the nitrogen source provides nitrogen that can be taken up by the microorganism and incorporated by the microorganism into biomolecules such as proteins and nucleic acids) is intentionally added to the culture medium, or that no other nitrogen source is present in an amount sufficient to significantly increase the growth of the microorganisms or cells cultured in the referenced medium. Throughout this application, for brevity, the terms "nitrate-only" is used to characterize culture media in which nitrate is the only source of nitrogen that is available to the microorganisms for supporting growth.

Similarly, "the sole source of carbon (in the culture medium)" is used interchangeably with "substantially the sole source of carbon" and indicates that no other carbon source that can be metabolized by the microorganism (i.e., used for energy or for as a carbon source for the production of biomolecules) is present in an amount sufficient to significantly increase the productivity, growth, or propagation of the microorganisms or cells cultured in the referenced medium or that can become incorporated into biomolecules such as lipids produced by the microorganisms or cells at a percentage of greater than 5% of the carbon incorporated into the biomolecule.

"Nitrogen replete" conditions refer to media conditions in which no further growth or propagation benefit is conferred by adding additional nitrogen (in a form that can be used by the microorganism) to the medium. Similarly, "nutrient replete" conditions refer to media conditions in which no nutrient is limiting to growth or propagation, that is, when a medium is nutrient replete, adding additional nutrient(s) to the medium does not result in an improved growth or propagation rate. In the context of "nutrient replete", "nutrients" includes, as nonlimiting examples, phosphate, sulfur, iron, and optionally silica, but excludes carbon sources such as sugars or organic acids that may be used by the organism as an energy source.

Disclosed herein are methods for manipulating, assaying, culturing, and analyzing microorganisms. The invention set forth herein also makes use of standard methods, techniques, and reagents for cell culture, transformation of microorganisms, genetic engineering, and biochemical analysis that are known in the art. Although methods and materials similar or equivalent to those described herein can be used in practice or testing of the present invention, suitable methods and materials are described below. The materials, methods, and examples are illustrative only and are not intended to be limiting. Other features and advantages of the invention will be apparent from the detailed description and from the claims.

Mutant Microorganisms Having Increased Lipid Productivity

Tetratricopeptide repeat (TPR) domains are structural motifs present in a wide range of proteins that serve as interaction modules and multiprotein complex mediators. Polypeptides having TPRs regulate diverse biological processes, such as organelle targeting and protein import, vesicle fusion, and biomineralization (as reviewed in Zeytuni, N. et al. 2012, *Structure* 20(3):397-405). A TPR domain can be characterized as pfam13414 "TPR repeat", or as conserved domain COG0457, as conserved domain CDD 290150 or conserved domain CDD 276809 ("Tetratricopeptide repeat"). Alternatively or in addition, a TPR domain can be characterized as conserved domain c126005, the "SGT1, suppressor of G2 allele of SKP1" domain, which is a member of the PLN03088 superfamily of domains. A BLAST search of protein sequences at blast.ncbi.nlm.nih.gov typically provides a summary of domains found within the query sequence. Polypeptide sequences can be examined for the presence of a TPR domain for example by searching for pfam domains or conserved domains within the sequence on publicly available websites such as pfam.xfam.org or ncbi (blast.ncbi.nlm.nih.gov).

In some embodiments, this disclosure provides mutant microorganisms having attenuated and/or altered expression and/or function of at least one gene encoding a polypeptide having a TPR domain, where the mutant microorganisms have increased lipid productivity and/or exhibit increased partitioning of carbon to lipid with respect to a control microorganism. Also provided are mutant microorganisms having attenuated and/or altered expression and/or function of a gene or protein affecting the expression and/or function of a polypeptide having a TPR domain.

As provided herein, "attenuated expression of a gene" or "an attenuated gene" includes attenuated expression due to inactivation of a gene or deletion of a gene. As nonlimiting examples, a gene having attenuated expression can be a disrupted gene, e.g., a gene having a deletion or an insertional mutation that disrupts the reading frame by frame shifting and/or introduction of a stop codon to result in a protein having altered amino acid sequence and/or a truncated open reading frame (ORF), resulting in a nonfunctional protein. Insertional mutagenesis can also be by any means, whether by random or classical mutagenesis or by genetic engineering, and in various nonlimiting examples insertional mutation can be by means of a transposase, random insertion of introduced DNA, homologous recombination, or insertion of DNA mediated by a Cas/CRISPR system.

Insertional mutations can also be insertions that occur by mutagenesis and/or misrepair following mutagenesis that can be via classical mutagenesis (e.g., exposure to chemicals or ionizing radiation) or genetic engineering, where an insertional mutation can alter the reading frame or introduce one or more stop codons. An attenuated gene can also be a disrupted gene that has a deletion or insertion that disrupts the reading frame by introducing a stop codon, frame shifting (which may result in a different amino acid sequence and may also introduce a stop codon) and/or by deleting amino acid sequences from the polypeptide to result in a protein having altered amino acid sequence and/or an internally deleted or N- or C-terminally truncated open reading frame (ORF). A disrupted gene can have a deletion or insertion of from one to thousands of base pairs, for example Deletions or insertions can occur via homologous recombination/gene replacement, by the activity of a Cas/CRISPR system, or by classical mutagenesis, for example. An attenuated gene can also be a gene that includes at least one mutation that changes at least one amino acid in the amino acid sequence of the encoded polypeptide. Such an amino acid sequence change can alter the activity of the encoded protein Amino acid sequence changes having a higher likelihood of attenuating polypeptide function may occur in conserved domains, for example, for the polypeptides disclosed herein, an amino acid-altering mutation can occur in the TPR domain (e.g., a domain characterized as pfam13414 "TPR repeat", or as conserved domain COG0457, as conserved domain CDD 290150, as conserved domain CDD 276809 ("Tetratricopeptide repeat"), or as conserved domain c126005; or can occur in a DUF4470 domain Reduced or altered activity of the protein encoded by the gene can in some examples be deduced by an altered phenotype of the mutant microorganism having the attenuated gene, such as, e.g., increased lipid production and/or increased partitioning of carbon to lipid.

Mutants demonstrating attenuated expression of a gene encoding a polypeptide having a TPR domain and/or a DUF4470 domain or having attenuated expression or function of a protein having a TPR domain and/or a DUF4470 domain can in some embodiments be mutants that include mutations in noncoding regions of the gene encoding a polypeptide having a TPR domain and/or a DUF4470 domain. For example, the gene can include one or more altered, inserted, or deleted nucleotides in a 5' UTR, 5' upstream region (e.g., upstream of the transcriptional start site), 3' UTR, or an intron of a gene that encodes a polypeptide having a TPR domain and/or a DUF4470 domain. Further, "attenuated expression of a gene" in a mutant as provided herein includes attenuated expression resulting from RNAi, antisense RNA, microRNAs, or the like, or ribozymes directed against the gene.

Alternatively or in addition to having attenuated expression of a gene encoding a polypeptide having a TPR domain and/or a DUF4470 domain, a mutant microorganism as provided herein can have attenuated and/or altered expression and/or function of at least one gene encoding a polypeptide that includes an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% to SEQ ID NO:1 or SEQ ID NO:2. In various embodiments, such mutant microorganisms can produce more lipid and/or exhibit increased partitioning of carbon to lipid as compared to a control microorganism that does not have attenuated expression or function of a gene encoding a polypeptide having an amino acid sequence having at least 50% identity to SEQ ID NO:1 or SEQ ID NO:2.

In some embodiments, the gene encoding a polypeptide having a TPR domain or having an amino acid sequence having at least 50% identity to SEQ ID NO:1 or SEQ ID NO:2 is localized to the Naga_100148 g8 locus on chromosome 12 of *Nannochloropsis gaditana*, or is a syntenic gene of another species, for example, a syntenic gene of another heterokont (stramenopile), Eustigmatophyte, or *Nannochloropsis* species.

In some embodiments, the polypeptide having a TPR domain and/or an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:1 also includes a domain of unknown function characterized as DUF4470 and/or an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:2. In some exemplary embodiments, the polypeptide that has attenuated expression or function in a mutant as provided herein that produces more lipid than a wild type cell under substantially identical culture conditions includes a TPR domain (e.g., a pfam13414 "TPR repeat" domain or conserved domain COG0457) and further includes a domain of unknown function characterized as DUF4470. In some embodiments, a mutant microorganism as provided herein has attenuated expression of a gene encoding a polypeptide that includes the amino acid sequence of SEQ ID NO:1 or a conservative variant thereof or that includes the amino acid sequence of SEQ ID NO:2 or a conservative variant thereof. Further, the gene that in a mutant as provided herein has attenuated expression or encodes a polypeptide having attenuated expression or function can be a gene encoding a polypeptide having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:3. In some embodiments, a mutant microorganism as provided herein that has attenuated and/or altered expression and/or function of a gene encoding a polypeptide that has a TPR domain (e.g., SEQ ID NO:1 or an amino acid sequence having at least 50%, at least 55%, at least 60%, at least 65%, at least 70%, at least 75%, at least 80%, at least 85%, at least 90%, or at least 95% identity thereto) and a DUF4470 domain (e.g., SEQ ID NO:2 or an amino acid sequence having at least 50%, at least 55%, at least 60%, at least 65%, at least 70%, at least 75%, at least 80%, at least 85%, at least 90%, or at least 95% identity thereto) can have a sequence having 50%, at least 55%, at least 60%, at least 65%, at least 70%, at least 75%, at least 80%, at least 85%, at least 90%, or at least 95% identity to SEQ ID NO:3. The gene in some examples can have a coding sequence (open reading frame) having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:4.

Thus, in some embodiments, a mutant microorganism as provided herein has attenuated expression and/or function of a gene encoding a polypeptide having a TPR domain and/or having a DUF4470 domain, where reduced expression or function of the gene or polypeptide results in the mutant producing more lipid than a control microorganism that does not have attenuated expression or function of a polypeptide that includes a TPR domain and/or a DUF4470 domain. In some embodiments, in mutant microorganisms having attenuated and/or altered expression and/or function of at least one gene (including but not limited to inactivation and/or deletion of such a gene) encoding a polypeptide having a TPR domain and/or a DUF4470 domain, the expression level of at least one gene encoding a polypeptide having a TPR domain and/or DUF4470 domain is at least about 5%, 10%, 15%, 20%, 25%, 30%, 35%, 40%, 45%, 50%, 55%, 60%, 65%, 70%, 75%, 80%, 85%, 90%, 95%, 97%, 98%, or 99% or more lower than that of a wild-type microorganism. In some embodiments, the there is no detectable expression of the gene encoding a polypeptide having a TPR domain.

The production of lipid and/or increased partitioning of carbon to lipid may be measured using culture assays where the microorganism can be cultured under batch, semicontinuous, or continuous culture conditions. The culture conditions under which a mutant microorganism as provided herein having a mutated, disrupted, or attenuated gene encoding a polypeptide having a TPR domain produces more lipid than a control microorganism can be nitrogen limited (e.g., having less than about 5 mM, less than about 4 mM, less than about 3 mM, less than about 2 mM, or less than about 1 mM nitrogen, for example, between about 0.1 and about 4 mM, or between about 0.2 mM and about 3 mM nitrogen, or between about 0.3 and about 2.8 mM nitrogen, or between about 0.3 and 2 mM nitrogen, for example, between about 0.3 mM and about 1.5 mM nitrogen or between about 0.2 mM and about 1 mM nitrogen), or may be nitrogen replete, or may be nitrogen deplete, for example, having less than about 0.5 mM, less than about 0.4 mM, less than about 0.3 mM, or, less than about 0.2 mM or less than about 0.1 mM nitrogen in the culture medium.

In some embodiments, the mutant microorganisms as provided in this disclosure (for example, microorganisms obtained by classical mutagenesis or genetic engineering) produce at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, or at least about 200% more lipid than a control microorganism cultured under substantially identical conditions, which can optionally be conditions in which the control microorganism culture produces biomass. For example, the mutant microorganism can produce between about 25% and about 200% more, between about 25% and about 175% more, between about 25% and about 150% more, between about 25% and about 125% more, between about 50% and about 200% more, between about 50% and about 175% more, between about 50% and about 150% more, between about 50% and about 125% more, between about 75% and about 200% more, or between about 75% and about 175% more, between about 75% and about 150% more, or between about 75% and about 125% more (e.g., 25-250% more) lipid than a control microorganism when both the mutant microorganism and control microorganism are cultured under substantially identical conditions in which the control microorganism culture produces biomass. The culture conditions can be nitrogen replete, and can be nutrient replete, with respect to the control microorganism. In some embodiments the control microorganism is a wild type microorganism of the same species from which the mutant is directly or indirectly derived.

A mutant microorganism as provided herein can demonstrate greater lipid productivity than a control microorganism over a culture period of at least about one day, at least about two days, at least about three days, for example, over a culture period of at least about four, at least about five, at least about six, at least about seven, at least about eight, at least about nine, at least about ten, at least about eleven, at least about twelve, at least about thirteen, at least about fourteen, at least about fifteen, at least about twenty, at least about thirty, or at least about sixty days, or over a period that may be less than 180 days, less than 120 days, or less than 90 days, where the mutant can have a higher average daily lipid productivity over the time period. Greater lipid productivity can in some embodiments be demostrated by the mutant microorganism when the mutant microorganism and the control microorganism are cultured under substantially identical conditions that support growth and propagation of the control microorganism, e.g., conditions in which the control microorganism culture produces biomass. In some examples the culture period in which a mutant microorganism as provided herein demonstrates higher lipid productivity with respect to a control microorganism can be For example, a mutant microorganism as provided herein can produce at least about 5%, at least about 10%, at least about 15%, at least about 20%,at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, or at least about 200% more lipid than a control microorganism during a culture period of from three to 90 days, from three to 60 days, from three to thirty days, or from three to fifteen days. For example, a mutant microorganism as provided herein can produce at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, or at least about 200% more lipid than a control microorganism during a culture period ranging from about five to about 90 days, from about five to about 60 days, from about five to about thirty days, or from five to about fifteen days, or from about seven to about 90 days, from about seven to about 60 days, from about seven to about thirty days, from about seven to about twenty days, or from about seven to about fifteen days. In some embodiments, the mutant microorganism can produce between about 5% more to about 200% more, about 5% more to about 175% more, about 5% more to about 150% more, about 5% more to about 125% more, about 25% more to about 200% more, about 25% more to about 175% more, about 25% more to about 150% more, about 25% more to about 125% more, about 50% more to about 200% more, about 50% more to about 175% more, about 50% more to about 150% more, about 50% more to about 125% more, about 75% more to about 200% more, or about 75% more to about 175% more, about 75% more to about 150%, or about 75% more to about 125% more (e.g., 5-200% more) lipid with respect to a control microorganism for a culture period of from five to at least 30 days under culture conditions in which both the mutant and control microorganism are producing biomass.

The amount of lipid produced by a culture can be assessed by removing samples and analyzing lipids using methods known in the art. Productivity can be volumetric productivity, for example, the productivity of a culture can be expressed as weight per milliliter or liter of culture, and can be a daily productivity (e.g., mg/liter/day or g/liter/day), for example, an average daily productivity over multiple days of the culture (for example, at least about three, four, five, six, seven, eight, nine, ten, eleven, twelve, thirteen, fourteen fifteen, or more days), or can be a total amount produced per unit volume for a defined period of time in culture. Productivity is preferably measured multiple times during the culture period, for example, at least about twice or at least about three times, and may be assessed every day, every other day, every third day, etc.

Biomass production can be assessed, for example, by measuring total organic carbon (TOC) or by other methods, such as measuring dry weight, ash-free dry weight (AFDW). Methods for measuring TOC are known in the art (e.g., U.S. Pat. No. 8,835,149) and are provided herein. Methods of measuring AFDW are also well-known and can be found, for example, in U.S. Pat. No. 8,940,508, incorporated herein by reference in its entirety.

Methods of measuring the amount of lipid produced by microorganisms are also well-known in the art and provided in the examples herein. For example, total extractable lipid can be determined according to Folch et al. (1957) *J. Biol. Chem.* 226: 497-509; Bligh & Dyer (1959) *Can. J. Biochem. Physiol.* 37: 911-917; or Matyash et al. (2008) *J. Lipid Res.* 49:1137-1146, for example, and the percentage of biomass present as lipid can also be assessed using Fourier transform infrared spectroscopy (FT-IR) (Pistorius et al. (2008) *Biotechnol & Bioengin.* 103:123-129). Additional references for gravimetric analysis of FAME and TAGs are provided in U.S. Pat. No. 8,207,363 and WO 2011127118 for example, each incorporated herein by reference in its entirety.

A mutant microorganism as provided herein can produce, in various embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, or at least about 200% more lipid with respect to a control microorganism. In some embodiments, increased lipid production of a mutant as provided herein can be under culture conditions in which the control microorganism is producing biomass. For example, the mutant microorganism can produce between about 5% more to about 200% more, about 5% more to about 175% more, about 5% more to about 150% more, about 5% more to about 125% more, about 25% more to about 200% more, about 25% more to about 175% more, about 25% more to about 150% more, about 25% more to about 125% more, about 50% more to about 200% more, about 50% more to about 175% more, about 50% more to about 150% more, about 50% more to about 125% more, about 75% more to about 200% more, or about 75% more to about 175% more, about 75% more to about 150%, or about 75% more to about 125% more (e.g., 5-200% more) lipid with respect to a control microorganism under culture conditions in which the control microorganism is producing biomass, which may be, in some embodiments, culture conditions in which both the control microorganism and the mutant microorganism are producing biomass.

In some embodiments, a mutant microorganism as provided herein produces an average of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, or at least about 200% more (e.g., at least any of 25%, 50%, 100%, 150%, or 200% more) FAME lipids per day with respect to a control microorganism, when the mutant microorganism and control microorganism are cultured under the same culture conditions, where the culture conditions are nitrogen-replete, and are preferably nutrient replete, culture conditions with respect to the control microorganism, over a period of at least about one day, at least about two days, at least about three days, at least about four days, at least about five days, at least about seven days, at least about ten days, at least about twelve days, or at least about fourteen days. For example, the mutant microorganism can produce an average of between about 5% more to about 200% more, about 5% more to about 175% more, about 5% more to about 150% more, about 5% more to about 125% more, about 25% more to about 200% more, about 25% more to about 175% more, about 25% more to about 150% more, about 25% more to about 125% more, about 50% more to about 200% more, about 50% more to about 175% more, about 50% more to about 150% more, about 50% more to about 125% more, about 75% more to about 200% more, or about 75% more to about 175% more, about 75% more to about 150%, or about 75% more to about 125% more (e.g., 5-200% more) FAME lipids per day with respect to a control microorganism under culture conditions in which both the mutant and control microorganism are producing biomass.

In some embodiments, the culture conditions can include culturing in a culture medium that includes less than about 5 mM, less than about 4.5 mM, less than about 4 mM, less than about 3.5 mM, less than about 3 mM, less than about 2.5 mM, less than about 2 mM, less than about 1.5 mM, less than about 1 mM, less than about 0.5 mM (e.g., less than 5 mM), or substantially none of a reduced nitrogen source such as ammonium salt. For example, the ammonium concentration may be at a concentration ranging from about 0 to about 5 mM, from about 0 to about 4.5 mM, from about 0 to about 4.0 mM, from about 0 to about 3.5 mM, from about 0 to about 3 mM, from about 0 to about 2.5 mM, from about 0 to about 2.0 mM, from about 0 to about 1.5 mM, from about 0 to about 1.0 mM, or from about 0 to about 0.5 mM (e.g., 0-5 mM). The ammonium concentration may be at a concentration ranging from about 0.2 to about 3 mM, 0.2 to about 2.5 mM, from about 0.2 to about 2 mM, from about 0.2 to about 1.5 mM, about 0.2 to about 1 mM, from about 0.3 to about 2.5 mM, from about 0.3 to about 2 mM, from about 0.3 to about 1.5 mM, or from about 0.3 to about 1 mM (e.g., 0.2-3 mM). In further examples, the ammonium concentration may be at a concentration ranging from about 0.4 mM to about 2.5 mM, from about 0.4 to about 2 mM, or from about 0.4 mM to about 1.5 mM (e.g., 0.4-2.5 mM). Alternatively or in addition, the culture conditions can include culturing in a culture medium that includes nitrate as substantially the sole source of nitrogen. In some embodiments, a mutant microorganism as provided herein more lipid with respect to a control microorganism, when the mutant microorganism and control microorganism are cultured under the same culture conditions, where the culture conditions are nitrogen-replete, and may be nutrient replete culture conditions with respect to the control microorganism. In some examples, the mutant microorganism can more lipid with respect to a control microorganism under culture conditions in which both the mutant and control microorganism are producing biomass. The control microorganism in some examples is a wild type microorganism, e.g., a wild type microorganism from which the mutant microorganism is directly or indirectly derived.

In some embodiments, a mutant microorganism as provided herein is an alga that produces at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, or at least about 200% more (e.g., at least any of 25%, 50%, 100%, 150%, or 200% more) FAME lipids than a control alga when cultured under photoautotrophic conditions. The phtoautotrophic culture conditions can include a medium that includes less than about 5 mM, less than about 4.5 mM, less than about 4 mM, less than about 3.5 mM, less than about 3 mM, less than about 2.5 mM ammonium, less than about 2.0 mM, less than about 1.5 mM ammonium, less than about 1.0 mM ammonium, less than about 0.5 mM ammonium (e.g., less than 5 mM), or substantially no ammonium, and includes, for example, at least about 1.0 mM, at least about 2.0 mM, at least about 3.0 mM, at least about 4.0 mM, at least about 5.0 mM, at least about 6.0 mM, at least about 7.0 mM, at least about 8.0 mM, at least about 9.0 mM, or at least about 10.0 mM nitrate (e.g., at least 1.0 mM). For example, the ammonium concentration may be at a concentration ranging from about 0 to about 5 mM, from about 0 to about 4.5 mM, from about 0 to about 4.0 mM, from about 0 to about 3.5 mM, from about 0 to about 3 mM, from about 0 to about 2.5 mM, from about 0 to about 2.0 mM, from about 0 to about 1.5 mM, from about 0 to about 1.0 mM, or from about 0 to about 0.5 mM (e.g., 0-5 mM). The ammonium concentration may be at a concentration ranging from about 0.2 to about 3 mM, 0.2 to about 2.5 mM, from about 0.2 to about 2 mM, from about 0.2 to about 1.5 mM, about 0.2 to about 1 mM, from about 0.3 to about 2.5 mM, from about 0.3 to about 2 mM, from about 0.3 to about 1.5 mM, or from about 0.3 to about 1 mM (e.g., 0.2-3 mM). In further examples, the ammonium concentration may be at a concentration ranging from about 0.4 mM to about 2.5 mM, from about 0.4 to about 2 mM, or from about 0.4 mM to about 1.5 mM (e.g., 0.4-2.5 mM). The photoautotrophic conditions may be under constant light or under a diel cycle. The light period of the diel cycle may be of any length and can be, for example, from about four hours to about twenty-two hours, and can be, for example, from about six hours to about twenty hours, e.g., from about eight hours to about eighteen hours per twenty-four hour cycle. The microorganism can be exposed to natural or artificial light or a combination thereof. The available light can vary in intensity throughout the light period.

Mutant microorganisms provided herein can have greater partitioning of carbon to lipid with respect to a control microorganism cultured under identical conditions. In some embodiments, both the control microorganism and the mutant microorganism are producing biomass. A mutant having increased partitioning of carbon to lipid with respect to a control microorganism can have increased partitioning of carbon to total extractable lipid, to total neutral lipids, to triglycerides, and/or to FAME-derivatizable lipids.

In some examples, a mutant microorganism as provided herein can have a ratio of the amount of FAME-derivatizable lipids ("FAME") produced to biomass (TOC or ash-free dry weight (AFDW), for example) produced that is at least about 5%, at least 10%, at least 15%, at least 20%, at least 30%, at least 40%, at least 50%, at least 60%, at least 70%, at least 80%, at least 90%, at least 100%, at least 120%, at least 140%, at least 160%, at least 180%, at least 200%, at least 220%, at least 240%, at least 260%, at least 280%, or at least 300% higher than that of a control microorganism when the mutant microorganism and the control microorganism are cultured under the same conditions. For example, the mutant microorganism can have a ratio of the amount of FAME-derivatizable lipids ("FAME") produced to biomass (TOC or ash-free dry weight (AFDW), for example) produced that is between about 25% higher to about 300% higher, about 25% higher to about 275% higher, about 25% higher to about 250% higher, about 5% higher to about 225% higher, 25% higher to about 200% higher, about 25% higher to about 175% higher, about 25% higher to about 150% higher, about 50% higher to about 300% higher, about 50% higher to about 275% higher, about 50% higher to about 250% higher, about 50% higher to about 225% higher, about 50% higher to about 200% higher, about 50% higher to about 175% higher, about 50% higher to about 150% higher, about 75% higher to about 300% higher, about 75% higher to about 275% higher, about 75% higher to about 250% higher, about 75% higher to about 225% higher, about 75% higher to about 200% higher, about 75% higher to about 175% higher, or about 75% higher to about 150% higher (e.g., 25-300% higher) lipid productivity with respect to a control microorganism when both the mutant microorganism and control microorganism are cultured under substantially identical conditions, which may be conditions in which the control microorganism culture produces biomass. Lipid and biomass production and/or production can be assessed, for example, by gravimetric analysis as known in the art and demonstrated in the examples herein.

In various examples, the FAME/TOC ratio of a mutant microorganism as provided herein can be, for example, at least about 0.30, at least about 0.35, at least about 0.40, at least about 0.45, at least about 0.50, at least about 0.55, at least about 0.60, at least about 0.65, at least about 0.70, at least about 0.75, at least about 0.80, at least about 0.85, or at least about 0.90 (e.g., at least any of 0.30, 0.50, 0.75, or 0.80) when cultured under conditions that are nitrogen replete, for example, nutrient replete, with respect to a control microorganism substantially identical to the mutant microorganism except that the control microorganism does not have a mutated gene encoding a polypeptide with a TRP domain. In various examples, the FAME/TOC ratio of a mutant microorganism as provided herein can be, for example, between about 0.25 and about 0.80, or between about 0.30 and about 0.80, or between about 0.25 and about 0.7, or between about about 0.30 and about 0.70, when cultured under conditions that are nitrogen replete, for example, nutrient replete, with respect to the control microorganism. The culture conditions can include, for example, a culture medium that includes less than about 5 mM, less than about 4.5 mM, less than about 4 mM, less than about 3.5 mM, less than about 3 mM, less than about 2.5 mM, less than about 2 mM, less than about 1.5 mM, less than about 1.0 mM, or less than about 0.5 mM (e.g., less than 5 mM) ammonium and in some examples can include at least about 1.0 mM, at least about 2.0 mM, at least about 3.0 mM, at least about 4.0 mM, at least about 5.0 mM, at least about 6.0 mM, at least about 7.0 mM, at least about 8.0 mM, at least about 9.0 mM, or at least about 10.0 mM (e.g., at least 1.0 mM) nitrate. The culture conditions can in some examples include substantially no ammonium, and in some examples can include substantially no reduced nitrogen as a nitrogen source. The culture in some examples includes nitrate as a nitrogen source, which can optionally be substantially the sole nitrogen source in the culture medium. In an illustrative embodiment, the mutant microorganism exhibits an average FAME/TOC ratio over the culture period of at least about 0.4.

The properties of a mutant as provided herein having increased lipid production are compared to the same properties of a control microorganism that may be a wild type organism of the same species as the mutant, preferably the progenitor strain of the lipid-overproducing mutant. Alternatively, a control microorganism can be a microorganism that is substantially identical to the mutant microorganism with the exception that the control microorganism does not have the mutation that leads to higher lipid productivity. For example, a control microorganism can be a genetically engineered microorganism or classically mutated organism that has been further mutated or engineered to generate a mutant having increased lipid productivity and/or increased lipid partitioning as disclosed herein.

In some examples, a control microorganism can be a microorganism that is substantially identical to the mutant microorganism, with the exception that the control microorganism does not have a mutation in a gene that regulates lipid induction (i.e., the gene whose mutation results in increased lipid production). The properties of a lipid-overproducing mutant having a disrupted, attenuated, or otherwise directly or indirectly genetically manipulated gene (resulting in altered structure or expression of the lipid induction regulator gene) are also be compared with the same properties of a control cell that does not have a disrupted, attenuated, or otherwise directly or indirectly genetically manipulated lipid induction regulator gene resulting in altered structure or expression of the lipid induction regulator gene (regardless of whether the cell is "wild type"). For example, a control cell may be a recombinant cell that includes one or more non-native genes or a cell mutated in a gene other than the lipid induction regulator gene whose effects are being assessed, etc.

The mutant microorganism can be of any eukaryotic microalgal strain such as, for example, any species of any of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria, and Volvox*. Non-limiting examples of particularly suitable species include, for instance, diatoms such as, for example, a species of any of the genera *Amphora, Chaetoceros, Cyclotella, Fragilaria, Fragilaropsis, Hantzschia, Monodus, Navicula, Nitzschia, Phæodactylum, or Thalassiosira*, or Eustigmatophytes, e.g., *Eustigmatos, Nannochloropsis, Pseudostaurastrum,* or *Vischeria*.

In some examples, the recombinant alga is a green alga, i.e., an algal member of the Chlorophyte division of the Viridiplantae kingdom, including without limitation, a microalga of any of the classes Chlorophyceae, Chlorodendrophyceae, Pedinophyceae, Pleurastrophyceae, Prasinophyceae, and Trebouxiophyceae. In some examples, a recombinant alga as provided herein can be a species that is a member of any of the Chlorophyceae, Prasinophyceae, Trebouxiophyceae, or Chlorodendrophyceae classes, such as a species of any of the *Asteromonas, Ankistrodesmus, Carteria, Chlamydomonas, Chlorococcum, Chlorogonium, Chrysosphaera, Desmodesmus, Dunaliella, Haematococcus, Monoraphidium, Neochloris, Oedogonium, Pelagomonas, Pleurococcus, Pyrobotrys, Scenedesmus, Volvox, Micromonas, Ostreococcus Prasinocladus Scherffelia, Tetraselmis, Botryococcus, Chlorella, Eremosphaera, Franceia, Micractinium, Nannochloris, Oocystis, Parachlorella, Picochlorum, Prototheca,* or *Pseudochlorella* genera. In various examples, a recombinant alga as provided herein can be a species or strain of the Trebouxiophyceae, such as but not limited to *Botryococcus, Chlorella, Eremosphaera, Franceia, Micractinium, Nannochloris, Oocystis, Parachlorella, Picochlorum, Prototheca,* or *Pseudochlorella*.

In some examples, the recombinant alga is a heterokont alga, and may belong to the diatoms (bacillariophytes), eustigmatophytes, xanthophytes, phaeophytes, chrysophytes, or raphidophytes. In some examples, the mutant alga belongs to a Bacillariophyte or Eustigmatophyte genus such as but not limited to *Amphiprora, Amphora, Chaetoceros, Cyclotella, Fragilaria, Fragilaropsis, Hantzschia, Monodus, Nannochloropsis, Navicula, Nitzschia, Phæodactylum, Phæodactylum, Pseudostaurastrum, Vischeria, Phæodactylum, Skeletonema,* and *Thalassiosira*. In some examples, the mutant alga is a Eustigmatophyte and belongs to a genus selected from the group consisting of *Chloridella, Chlorobptrys, Ellipsoidion, Eustigmatos, Goniochloris, Monodopsis, Monodus, Nannochloropsis, Pseudocharac-*

*iopsis, Pseudostaruastrum, Pseudotetraedriella*, and *Vischeria*. In some examples, the mutant alga cell is a *Nannochloropsis* species.

Alternatively, a mutant microorganism as provided herein may be a heterokont that is a Labyrinthulomycete microorganism, e.g., a member of the Labrinthulids or Thraustochytrids, such as, for example, a species of any of the genera *Labryinthula, Labyrinthuloides, Thraustochytrium, Schizochytrium, Aplanochytrium, Aurantiochytrium, Oblongichytrium, Japonochytrium, Diplophrys*, and *Ulkenia*.

The mutants can be spontaneous mutants, classically-derived mutants, or engineered mutants having attenuated expression of a regulator gene, for example, a gene whose expression affects the expression of many other genes such as a gene encoding a transcription factor or a transcriptional activator.

The mutant microorganism having attenuated expression of a gene that regulates lipid production can be a "knockout" mutant, for example, in which the reading frame of the polypeptide is disrupted such that the functional protein is not produced. For example, the gene can include an insertion, deletion, or mutation in the reading frame that results in no functional protein being made. In various examples, a knockout mutation can be generated by insertion of a sequence, often but not necessarily including a selectable marker gene, into the gene, for example, into the coding region of the gene. Such an insertion can be by use of a Cas/CRISPR system that integrates a donor fragment into a targeted locus, or can be by homologous recombination, for example Such an insertion can disrupt an open reading frame and/or splicing signals, or generate nonfunctional fusion proteins or truncated proteins. In other examples, the mutant microorganism can be a "knockdown" mutant in which expression of the gene is reduced but not eliminated, for example, reduced from 5% or less to 95% or more, for example, from 5% to 95% or 10% to 90%, with respect to expression levels of a wild type cell. Knockdowns can be mutants in which a mutation, insertion, or deletion occurs in a non-coding region of the gene, for example, the 5' or 3' region of a gene, or can be effected by expressing constructs in the cells that reduce expression of the targeted gene, such as RNAi, ribozyme, or antisense constructs. In addition to CRISPR systems, homologous recombination can be used to generate insertion mutants (either knockdown or knockout). Other methods are also known and widely available to those of ordinary skill in the art and may be used with the microorganisms described herein.

A mutant microorganism as provided herein can be designed by targeting an endogenous gene of a microorganism of interest that encodes a polypeptide that includes a TPR domain as disclosed herein. Such genes can be identified in a microorganism of interest using bioinformatics methods, molecular biology techniques and combinations thereof. For example, a gene encoding a polypeptide that includes a TPR domain can be identified using Southern hybridization, screening of cDNA libraries by hybridization, or PCR, for example, using degenerate probes and/or primers. Genome sequences available in public or proprietary databases can be searched by any of a number of programs that perform sequence matching (e.g., blast programs such as blastp, blastn, and tblastn (protein sequence queried against translated nucleotide sequence)) or analyze domain structures of encoded amino acid sequences. For example, HMMER provides software online for analyzing structural and functional domains encoded by genes that can be used to scan genome sequences, including, for example, hmmsearch and hmmscan. Such searches can be done online. Programs such as MUSCLE and hmmalign can also be used to search for orthologs of proteins such as the proteins disclosed herein (e.g., polypeptides having a TPR domain (e.g., SEQ ID NO:1 or an amino acid sequence having at least 65%, 70%, 75%, 80%, 85%, 90%, on 95% identity thereto), and/or DUF4470-containing polypeptides (e.g., SEQ ID NO:2 or an amino acid sequence having at least 65%, 70%, 75%, 80%, 85%, 90%, or 95% identity thereto)) by constructing phylogenetic trees to determine relationships among proteins. Gene targeting can make use of sequences identified in the genome of the microorganism of interest. It is not necessary to resolve the complete structure of a gene to target the gene for attenuation. For example, using methods disclosed herein, including, without limitation, genome editing (using meganucleases, zinc finger nucleases, TALENs, or Cas/CRISPR systems), RNAi constructs, antisense constructs, homologous recombination constructs, and ribozyme constructs, only a portion of a gene sequence can be employed in gene attenuation constructs and techniques.

In some embodiments, the mutant microorganism can be further engineered or mutagenized to have at least one additional genetic modification that confers herbicide resistance, toxin resistance, enhanced growth properties, enhanced photosynthetic efficiency, enhanced lipid production or accumulation, and production of particular lipids.

In one aspect, provided are lysates of mutant microorganisms disclosed in the above embodiments. Making cell lysates are known in the art. In some embodiments, lysates of mutant microorganisms can be made by subjecting the mutant microorganisms to detergents, hypotonic buffers, chaotropic agents, enzymes, e.g., proteases, or a combination of any thereof, and/or by sonication, freeze-thawing, mechanical means such as bead beating or grinding in liquid nitrogen, or any combinations thereof. A lysate may be a crude lysate of may be a lysate that has been further processed by, for example, by precipitation, settling, centrifugation, filtration, or dialysis.

Gene Attenuation

A mutant microorganism as provided herein having attenuated expression of a gene that regulates lipid biosynthesis is a mutant generated by human intervention, for example, by classical mutagenesis or genetic engineering. For example, a mutant microorganism as provided herein can be a mutant generated by any feasible mutagenesis method, including but not limited to UV irradiation, gamma irradiation, or chemical mutagenesis, and screening for mutants having increased lipid production, for example by staining with lipophilic dyes such as Nile Red or BODIPY (e.g., Cabanelas et al. (2015) *Bioresource Technology* 184: 47-52). Methods for generating mutants of microbial strains are well-known.

A mutant as provided herein that produces at least about 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, or at least 200% more lipid can also be a genetically engineered mutant, for example, a mutant in which a gene encoding a polypeptide having a TPR domain, or a gene localized to the Naga_100148 g8 locus or an ortholog thereof (e.g., a gene encoding a polypeptide having a TPR domain that has at least about 50%, at least 55%, at least 60%, at least 65%, at least 70%, at least 75%, at least 80%, at least 85%, at least 90%, at least 95%, at least 96%, at least 97%, at least 98%, or at least about 99% to SEQ ID NO:1; a gene encoding a polypeptide having a TPR domain that has at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2; and/or a gene encoding a polypeptide having a DUF4470 domain having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:3) has been targeted by homologous recombination for knock-out, knockdown, and/or gene replacement (for example with mutated form of the gene that may encode a polypeptide having reduced activity with respect to the wild type polypeptide). For example, a microbial strain of interest may be engineered by site directed homologous recombination to insert a sequence into a genomic locus and thereby alter a gene and/or its expression, and/or to insert a promoter into a genetic locus of the host microorganism to affect the expression of a particular gene or set of genes at the locus.

For example, gene knockout, gene knockdown, or gene replacement by homologous recombination can be by transformation of a nucleic acid (e.g., DNA) fragment that includes a sequence homologous to the region of the genome to be altered, where the homologous sequence is interrupted by a foreign sequence, typically a selectable marker gene that allows selection for the integrated construct. The genome-homologous flanking sequences on either side of the foreign sequence or mutated gene sequence can be for example, at least about 50, at least about 100, at least about 200, at least about 300, at least about 400, at least about 500, at least about 600, at least about 700, at least about 800, at least about 900, at least about 1,000, at least about 1,200, at least about 1,500, at least about 1,750, or at least about 2,000 (e.g., at least any of 50, 100, 200, 500, 1000, 1500 or 2000) nucleotides in length. A gene knockout or gene "knock in" construct in which a foreign sequence is flanked by target gene sequences, can be provided in a vector that can optionally be linearized, for example, outside of the region that is to undergo homologous recombination, or can be provided as a linear fragment that is not in the context of a vector, for example, the knock-out or knock-in construct can be an isolated or synthesized fragment, including but not limited to a PCR product. In some instances, a split marker system can be used to generate gene knock-outs by homologous recombination, where two DNA fragments can be introduced that can regenerate a selectable marker and disrupt the gene locus of interest via three crossover events (Jeong et al. (2007) *FEMS Microbiol Lett* 273: 157-163).

In one aspect this disclosure provides genetically modified organisms, e.g., microorganisms having one or more genetic modifications or mutations for attenuating expression of a lipid regulator gene such as a gene encoding a polypeptide having a TPR domain that has at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to SEQ ID NO:1; and/or a gene encoding a polypeptide having a DUF4470 domain that has at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to SEQ ID NO:2; and/or a gene encoding a polypeptide having at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to SEQ ID NO:3; and/or a gene localized to the Naga_100148 g8 locus or a syntenic locus in a heterokont or algal species; and/or a gene having a coding region with at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to SEQ ID NO:4. As used herein "attenuating" or "altering" the expression and/or function" of a gene (e.g., a "lipid regulator gene") means reducing or eliminating expression of the gene in any manner that reduces production, expression and/or function of the normally expressed fully functional protein. Means for attenuating a gene such as a lipid regulator gene include, for example, homologous recombination constructs; CRISPR systems, including guide RNAs, Cas9 or other cas enzymes, e.g., Cpf1, Cms1, Csm1, or others, and optionally, donor fragments for insertion into the targeted site; RNAi constructs, including shRNAs, antisense RNA constructs; ribozyme constructs; TALENS, Zinc Finger nucleases; and meganucleases. For instance, in some embodiments, the gene can be disrupted by, for example, an insertion or gene replacement mediated by homologous recombination and/or by the activity of a double strand break inducing agent such as meganuclease (see, e.g., WO2012017329 (US20130164850 and US20160272980), zinc finger nuclease (Perez-Pinera et al. (2012) *Curr. Opin. Chem. Biol.* 16:268-277; WO2012017329 (US20130164850 and US20120324603), TALEN (WO2014/207043 (US20160130599); WO 2014/076571 (US20160272980)), or a cas protein (e.g., a Cas9 protein, Cpf1 effector protein, or Csm1 effector protein) of a CRISPR system (see e.g., U.S. Pat. Nos. 8,697,359; 8,795,965; 8,889,356; US 2016/0304893; US 2016/0090603; US2014/0068797; US 2016/0208243; US 2017/0233756). Other methods of disruption are known in the art and would be suitable here as would be understood by those of ordinary skill in the art.

In some embodiments, the mutant microorganism has one or more mutations to, or one or more mutations affecting the expression of, a gene localized to the Naga_100148 g8 locus or a syntenic locus in a heterokont or algal species. In some embodiments, the mutant microorganism has one or more mutations to, or one or more mutations that affects the expression of, a gene having an open reading frame having at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to SEQ ID NO:4. In some embodiments, the mutant microorganism has one or more mutations that are present in or affect expression of: a nucleic acid encoding a polypeptide having an amino acid sequence of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to SEQ ID NO:1, SEQ ID NO:2, or SEQ ID NO:3. In some embodiments, the mutant microorganism has one or more mutations in sequence encoding the DUF4470 domain (e.g., SEQ ID NO:2 or a sequence having at least about 50%, at least 60%, at least 70%, at least 80%, at least 85%, at least 90%, or at least about 95% thereto). In some embodiments, the mutant microorganism has one or more mutations in sequence encoding the TPR domain (e.g., SEQ ID NO:1 or a sequence having at least about 50%, at least 60%, at least 70%, at least 80%, at least 85%, at least 90%, or at least about 95% thereto).

A recombinant microorganism engineered to have attenuated expression of a lipid regulator gene can have a disrupted lipid regulator gene that includes as least one insertion, mutation, or deletion that reduces or abolishes expression of the gene such that a fully functional lipid regulator gene is not produced or is produced in lower amounts than is produced by a control microorganism that does not include a disrupted lipid regulator gene. For instance, in some embodiments, one or more mutations (change, deletion, and/or insertion of one or more nucleotides) can be in the coding region of the gene or can be in an intron, 3' UTR, 5' UTR, or promoter region, e.g., within about 1 kb of the transcriptional start site, within about 2 kb of the transcriptional start site or within about 3 kb of the translational start site. In some embodiments, for example, a mutant microorganism having attenuated expression of a gene as disclosed herein can have one or more mutations, which can be one or more nucleobase changes and/or one or more nucleobase deletions and/or one or more nucleobase insertions, into the region of a gene 5' of the transcriptional start site, such as, in non-limiting examples, within about 2 kb, within about 1.5 kb, within about 1 kb, or within about 0.5 kb of the known or putative transcriptional start site, or within about 3 kb, within about 2.5 kb, within about 2 kb, within about 1.5 kb, within about 1 kb, or within about 0.5 kb of the translational start site. As nonlimiting examples, a mutant gene can be a gene that has a mutation, insertion, or deletion within the promoter region that can either increase or decrease expression of the gene; can be a gene that has a deletion that results in production of a nonfunctional protein, truncated protein, dominant negative protein, or no protein; can be a gene that has one or more point mutations leading to a change in the amino acid of the encoded protein or results in aberrant splicing of the gene transcript, etc.

The CRISPR systems referred to herein, and reviewed recently by Hsu et al. (*Cell* 157:1262-1278, 2014) include, in addition to the cas nuclease polypeptide or complex, a targeting RNA, often denoted "crRNA", that interacts with the genome target site by complementarity with a target site sequence, a trans-activating ("tracr") RNA that complexes with the cas polypeptide and also includes a region that binds (by complementarity) the targeting crRNA. This disclosure contemplates the use of two RNA molecules (a "crRNA" and a "tracrRNA") that can be co-transformed into a host strain (or expressed in a host strain) that expresses or is transfected with a cas protein for genome editing, or the use of a single guide RNA that includes a sequence complementary to a target sequence as well as a sequence that interacts with a cas protein. That is, in some strategies a CRISPR system as used herein can comprise two separate RNA molecules (RNA polynucleotides: a "tracrRNA" and a "targeter-RNA" or "crRNA", see below) and referred to herein as a "double-molecule DNA-targeting RNA" or a "two-molecule DNA-targeting RNA." Alternatively, as illustrated in the examples, the DNA-targeting RNA can also include the trans-activating sequence for interaction with the cas protein (in addition to the target-homologous ("cr") sequences), that is, the DNA-targeting RNA can be a single RNA molecule (single RNA polynucleotide) and is referred to herein as a "chimeric guide RNA," a "single-guide RNA," or an "sgRNA." The terms "DNA-targeting RNA" and "gRNA" are inclusive, referring both to double-molecule DNA-targeting RNAs and to single-molecule DNA-targeting RNAs (i.e., sgRNAs). Both single-molecule guide RNAs and two RNA systems have been described in detail in the literature and for example, in U.S. Patent Application Publication No. US 2014/0068797, incorporated by reference herein in its entirety. Some embodiments of the methods and compositions presented herein include a guide RNA that has a sequence corresponding to a target sequence in a gene localized to the Naga_100148 g8 locus, such as for example, a target sequence having the sequence set forth in SEQ ID NO:5. In some embodiments, the guide RNA is a chimeric guide. In other embodiments, the guide RNA does not include a tracr sequence. Any cas protein can be used in the methods herein, e.g., Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm1, Csm2, Csm3, Csm4, Csm5, Csm6, Cmr1, Cmr3, Cmr4, Cmr5, Cmr6, Cms1, Cpf1, Csb1, Csb2, Csb3, Csx17, Csx14, Csx10, Csx16, CsaX, Csx3, Csxl, Csx15, Csf1, Csf2, Csf3, Csf4, C2c1, C2c2, C2c3, and homologs thereof, or modified versions thereof. The cas protein can be a Cas9 protein, such as a Cas9 protein of *Staphylococcus pyogenes, S. thermophilus, S. pneumonia, S. aureus*, or *Neisseria meningitidis*, as nonlimiting examples. Also considered are the Cas9 proteins provided as SEQ ID NOs:1-256 and 795-1346 in U.S. Patent Application Publication No. US 2014/0068797, incorporated herein by reference in its entirety, and chimeric Cas9 proteins that may combine domains from more than one Cas9 protein, as well variants and mutants of identified Cas9 proteins. The RNA-guided nuclease can be, for example, a Cpf1 protein (see, for example, US 2016/0208243) or a Csm1 protein (see, for example, US 2017/0233756).

Cas nuclease activity cleaves target DNA to produce double strand breaks. These breaks are then repaired by the cell in one of two ways: non-homologous end joining or homology-directed repair. In non-homologous end joining (NHEJ), the double-strand breaks are repaired by direct ligation of the break ends to one another. In this case, no new nucleic acid material is inserted into the site, although some nucleic acid material may be lost, resulting in a deletion, or altered, often resulting in mutation. In homology-directed repair, a donor polynucleotide (sometimes referred to as a "donor DNA" or "editing DNA") which may have homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. The modifications of the target DNA due to NHEJ and/or homology-directed repair (for example using a donor DNA molecule) can lead to, for example, gene correction, gene replacement, gene tagging, transgene insertion, nucleotide deletion, gene disruption, gene mutation, etc.

In some instances, cleavage of DNA by a site-directed modifying polypeptide (e.g., a cas nuclease, zinc finger nuclease, meganuclease, or TALEN) may be used to delete nucleic acid material from a target DNA sequence by cleaving the target DNA sequence and allowing the cell to repair the sequence in the absence of an exogenously provided donor polynucleotide. Such NHEJ events can result in mutations ("mis-repair") at the site of rejoining of the cleaved ends that can resulting in gene disruption.

Alternatively, if a DNA-targeting RNA is co-administered to cells that express a cas nuclease along with a donor DNA, the subject methods may be used to add, i.e. insert or replace, nucleic acid material to a target DNA sequence (e.g., "knock out" by insertional mutagenesis, or "knock in" a nucleic acid that encodes a protein (e.g., a selectable marker and/or any protein of interest), an siRNA, a miRNA, etc., to modify a nucleic acid sequence (e.g., introduce a mutation), and the like.

A donor DNA can in particular embodiments include a gene regulatory sequence (e.g., a promoter) that can, using CRISPR targeting, be inserted upstream of the coding regions of the gene and upstream of the presumed proximal promoter region of the gene, for example, at least about 50 bp, at least about 100 bp, at least about 120 bp, at least about 150 bp, at least about 200 bp, at least about 250 bp, at least about 300 bp, at least about 350 bp, at least about 400 bp, at least about 450 bp, or at least about 500 bp (e.g., at least 50, 100, 200, 300, 400 or 500 bp) upstream of the initiating ATG of the coding region of the lipid regulator gene. The donor DNA can include a sequence, such as for example a selectable marker or any convenient sequence, that may be interfere with the native promoter. The additional sequence inserted upstream of the initiating ATG of the lipid regulator open reading frame (e.g., in the 5'UTR or upstream of the transcriptional start site of the lipid regulator gene) can decrease or even eliminate expression of the endogenous lipid regulator gene. Alternatively, or in addition, the native lipid regulator gene can have its endogenous promoter wholly or partially replaced by a weaker or differently regulated promoter, or a non-promoter sequence.

In some examples, a nucleic acid molecule introduced into a host cell for generating a high efficiency genome editing cell line encodes a Cas9 enzyme that is mutated to with respect to the corresponding wild-type enzyme such that the mutated Cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (an enzyme that cleaves a single strand). Other examples of mutations that render Cas9 a nickase include, without limitation, H840A, N854A, and N863A. In some embodiments, a Cas9 nickase may be used in combination with guide sequence(s), e.g., two guide sequences, which target respectively sense and antisense strands of the DNA target. This combination allows both strands to be nicked and used to induce NHEJ. Two nickase targets (within close proximity but targeting different strands of the DNA) can be used to inducing mutagenic NHEJ. Such targeting of a locus using enzymes that cleave opposite strains at staggered positions can also reduce nontarget cleavage, as both strands must be accurately and specifically cleaved to achieve genome mutation. In additional examples, a mutant Cas9 enzyme that is impaired in its ability to cleave DNA can be expressed in the cell, where one or more guide RNAs that target a sequence upstream of the transcriptional or translational start site of the targeted gene are also introduced. In this case, the cas enzyme may bind the target sequence and block transcription of the targeted gene (Qi et al. (2013) *Cell* 152:1173-1183). This CRISPR interference of gene expression can be referred to as RNAi and is also described in detail in Larson et al. (2013) *Nat. Protoc.* 8: 2180-2196. In some cases, a cas polypeptide such as a Cas9 polypeptide is a fusion polypeptide, comprising, e.g.: i) a Cas9 polypeptide (which can optionally be variant Cas9 polypeptide as described above); and b) a covalently linked heterologous polypeptide (also referred to as a "fusion partner"). A heterologous nucleic acid sequence may be linked to another nucleic acid sequence (e.g., by genetic engineering) to generate a chimeric nucleotide sequence encoding a chimeric polypeptide. In some embodiments, a Cas9 fusion polypeptide is generated by fusing a Cas9 polypeptide with a heterologous sequence that provides for subcellular localization (i.e., the heterologous sequence is a subcellular localization sequence, e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a hemagglutinin (HA) tag; a FLAG tag; a Myc tag; and the like).

Host cells can be genetically engineered (e.g., transduced or transformed or transfected) with, for example, a vector construct that can be, for example, a vector for homologous recombination that includes nucleic acid sequences homologous to a portion of a lipid regulator gene locus of the host cell or to regions adjacent thereto, or can be an expression vector for the expression of any or a combination of: a cas protein (e.g., a Cas9 protein), a CRISPR chimeric guide RNA, a crRNA, and/or a tracrRNA, an RNAi construct (e.g., a shRNA), an antisense RNA, or a ribozyme. The vector can be, for example, in the form of a plasmid, a viral particle, a phage, etc. A vector for expression of a polypeptide or RNA for genome editing can also be designed for integration into the host, e.g., by homologous recombination. A vector containing a polynucleotide sequence as described herein, e.g., sequences having homology to host lipid regulator gene sequences (including sequences that are upstream and downstream of the lipid regulator-encoding sequences), as well as, optionally, a selectable marker or reporter gene, can be employed to transform an appropriate host to cause attenuation of a lipid regulator gene.

The recombinant microorganism in some examples can have reduced but not abolished expression of the lipid regulator gene, and the recombinant microorganism can have an increase in lipid production of from about 25% to about 200% or more, for example. For example, the increase in lipid production can be between about 25% more to about 200% more, about 25% more to about 175% more, about 25% more to about 150% more, about 25% more to about 125% more, about 50% more to about 200% more, about 50% more to about 175% more, about 50% more to about 150% more, about 50% more to about 125% more, about 75% more to about 200% more, or about 75% more to about 175% more, about 75% more to about 150%, or about 75% more to about 125% more (e.g., 25-200% more) with respect to a control microorganism. A genetically modified microorganism as provided herein can in some examples include a nucleic acid construct for attenuating the expression of a lipid regulator gene, such as, for example, a gene encoding a polypeptide having a TPR domain, such as for example a TPR domain that has at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:1; and/or a gene encoding a TPR domain containing polypeptide having at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to SEQ ID NO:3; and/or a gene encoding a polypeptide having a DUF4470 domain having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:2. In some embodiments, genetically modified microorganism as provided herein can include a nucleic acid construct for attenuating the expression of a polypeptide comprising SEQ ID NO:1 or an amino acid sequence having at least about 50%, at least 60%, at least 70%, at least 80%, at least 85%, at least 90%, or at least about 95% thereto, and/or a polypeptide comprising SEQ ID NO:2 or an amino acid sequence having at least about 50%, at least 60%, at least 70%, at least 80%, at least 85%, at least 90%, or at least about 95% thereto. For example, a host microorganism can include a construct for expressing an RNAi molecule, ribozyme, or antisense molecule that reduces expression of a lipid regulator gene encoding a polypeptide having a TPR domain and/or a DUF4470 domain, or having at least about 50%, at least 55%, at least 60%, at least 65%, at least 70%, at least 75%, at least 80%, at least 85%, at least 90%, at least 95%, or at least about 99% identity to SEQ ID NO:3. In some examples, a recombinant microorganism as provided herein can include at least one introduced (exogenous or non-native) construct for reducing expression of a lipid regulator gene.

In some examples, genetically engineered strains can be screened for expression of a lipid regulator gene that is decreased with respect to a control cell that does not include a genetic modification for attenuating lipid regulator gene expression, but not eliminated, using methods known in the art, such as, for example, RNA-Seq or reverse transcription-PCR (RT-PCR). A genetically engineered strain as provided herein can be engineered to include a construct for attenuating gene expression by reducing the amount, stability, or translatability of mRNA of a gene encoding a lipid regulator. For example, a microorganism such as an algal or heterokont strain can be transformed with an antisense RNA, RNAi, or ribozyme construct targeting an mRNA of a lipid regulator gene using methods known in the art. For example, an antisense RNA construct that includes all or a portion of the transcribed region of a gene can be introduced into a microorganism to decrease gene expression (Shroda et al. (1999) *The Plant Cell* 11:1165-78; Ngiam et al. (2000) *Appl. Environ. Microbiol.* 66: 775-782; Ohnuma et al. (2009) *Protoplasma* 236: 107-112; Lavaud et al. (2012) *PLoS One* 7:e36806). Alternatively or in addition, an RNAi construct (for example, a construct encoding a short hairpin RNA) targeting a gene having a TPR domain can be introduced into a microorganism such as an alga or heterokont for reducing expression of the lipid regulator gene (see, for example, Cerruti et al. (2011) *Eukaryotic Cell* (2011) 10: 1164-1172; Shroda et al. (2006) *Curr. Genet.* 49:69-84).

Ribozymes are RNA-protein complexes that cleave nucleic acids in a site-specific fashion. Ribozymes have specific catalytic domains that possess endonuclease activity. For example, U.S. Pat. No. 5,354,855 (incorporated herein in its entirety by reference) reports that certain ribozymes can act as endonucleases with a sequence specificity greater than that of known ribonucleases and approaching that of the DNA restriction enzymes. Catalytic RNA constructs (ribozymes) can be designed to base pair with an mRNA encoding a gene as provided herein to cleave the mRNA target. In some examples, ribozyme sequences can be integrated within an antisense RNA construct to mediate cleavage of the target. Various types of ribozymes can be considered, their design and use is known in the art and described, for example, in Haseloff et al. (1988) *Nature* 334:585-591. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A, C or U) (Thompson et al., (1995) *Nucl Acids Res* 23:2250-68). The frequency of this dinucleotide occurring in any given RNA is statistically 3 out of 16. Therefore, for a given target messenger RNA of 1,000 bases, 187 dinucleotide cleavage sites are statistically possible.

The general design and optimization of ribozyme directed RNA cleavage activity has been discussed in detail (Haseloff and Gerlach (1988) *Nature* 334:585-591; Symons (1992) *Ann Rev Biochem* 61: 641-71; Chowrira et al. (1994) *J Biol Chem* 269:25856-64; Thompson et al. (1995) supra), all incorporated by reference in their entireties. Designing and testing ribozymes for efficient cleavage of a target RNA is a process well known to those skilled in the art. Examples of scientific methods for designing and testing ribozymes are described by Chowrira et al., (1994) supra and Lieber and Strauss (1995) *Mol Cell Biol.* 15: 540-51, each incorporated by reference. The identification of operative and preferred sequences for use in down regulating a given gene is a matter of preparing and testing a given sequence, and is a routinely practiced "screening" method known to those of skill in the art. The use of RNAi constructs is described in literature cited above as well as in US2005/0166289 and WO 2013/016267 (both of which are incorporated herein by reference), for example A double stranded RNA with homology to the target gene is delivered to the cell or produced in the cell by expression of an RNAi construct, for example, an RNAi short hairpin (sh) construct. The construct can include a sequence that is identical to the target gene, or at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identical to a sequence of the target gene. The construct can have at least about 20, at least about 30, at least about 40, at least about 50, at least about 100, at least about 200, at least about 300, at least about 400, at least about 500, at least about 600, at least about 700, at least about 800, at least about 900, or at least about 1 kb of sequence (e.g., at least 20, 50, 100, 200, 400, 600, 800 or 1 kb of sequence) homologous to the target gene. Expression vectors can be engineered using promoters selected for continuous or inducible expression of an RNAi construct, such as a construct that produces an shRNA.

A nucleic acid construct for gene attenuation, e.g., a ribozyme, RNAi, or antisense construct can include at least about fifteen, at least about twenty, at least about thirty, at least about forty, at least about fifty, or at least about sixty nucleotides having at least about 80% identity, such as at least about 85%, at least about 90%, at least about 95%, or at least about 99 identity or complementarity to at least about a portion of the sequence of an endogenous lipid regulator gene of the microorganism to be engineered. A nucleic acid construct for gene attenuation, e.g., a ribozyme, RNAi, or antisense construct can include at least about fifteen, at least about twenty, at least about thirty, at least about forty, at least about fifty, or at least about sixty nucleotides having at least 80%, such as at least 95% or about 100%, identity or complementarity to the sequence of a naturally-occurring gene, such as a gene having encoding a polypeptide having at least about 50%, at least 55%, at least 60%, at least 65%, at least 70%, at least 75%, at least 80% or at least 85%, at least 90%, or at least 95% sequence identity to an endogenous lipid regulator gene, such as a gene localized to the Naga_100148 g8 locus or a syntenic locus, or a gene that encodes a polypeptide having a TPR domain, such as, e.g., SEQ ID NO:1, or a sequence having at least 50%, at least 60%, at least 70%, at least 80%, or at least 85%, at least 90%, or at least 95% identity thereto. For example, a nucleic acid construct for gene attenuation, e.g., a ribozyme, RNAi, or antisense construct can include at least about fifteen, at least about twenty, at least about thirty, at least about forty, at least about fifty, or at least about sixty nucleotides having at least about 80% identity or complementarity to the sequence of a naturally-occurring lipid regulator gene, such as any provided herein. The nucleotide sequence can be, for example, from at least about 30 nucleotides to at least about 3 kilobases, for example, from at least about 30 nucleotides to at least about 50 nucleotides in length, from at least about 50 nucleotides to at least about 100 nucleotides in length, from at least about 100 nucleotides to at least about 500 nucleotides in length, from at least about 500 nucleotides to at least about 1 kb in length, from at least about 1 kb to at least about 2 kb in length, or from at least about 2 kb to at least about 5 kb in length. For example, an antisense sequence can be from at least about 100 nucleotides to at least about 1 kb in length. For example, a nucleic acid construct for gene attenuation, e.g., a ribozyme, RNAi, or antisense construct can include at least about fifteen, at least about twenty, at least about thirty, at least about forty, at least about fifty, at least about sixty, or at least about 100 nucleotides having at least about 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity or complementarity to an endogenous lipid regulator gene or a portion thereof.

Promoters used in antisense, RNAi, or ribozyme constructs can be any that are functional in the host organism and that are suitable for the levels of expression required for reducing expression of the target gene to a desired amount. Promoters functional in algae and heterokonts are known in the art and disclosed herein. The construct can be transformed into algae using any feasible method, include any disclosed herein. A recombinant organism or microorganism transformed with a nucleic acid molecule for attenuating lipid regulator gene expression, such as but not limited to an antisense, RNAi, or ribozyme construct, can have the properties of a lipid regulator mutant as described herein, including, for example, reduced chlorophyll, increased photosynthetic efficiency, and increased productivity in culture, with respect to a host organism or microorganism that does not include the exogenous nucleic acid molecule that results in attenuated gene expression.

Nucleic Acid Molecules and Constructs

Also provided herein are nucleic acid molecules encoding polypeptides that include amino acid sequences having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to one or more of SEQ ID NOS:1-3. Alternatively or in addition, a nucleic acid molecule as provided herein can include a sequence having at least about 50%, at least 55%, at least 60%, at least 65%, at least 70%, at least 75%, at least 80%, at least 85%, at least 90%, at least 95%, at least 96%, at least 97%, at least 98%, or at least 99% to SEQ ID NOs:4. In some embodiments, the polypeptide encoded by the nucleic acid molecule can include a TPR domain and/or a DUF4470 domain and can have at least 50%, at least 55%, at least 60%, at least 65%, at least 70%, at least 75%, at least 80%, at least 85%, at least 90%, at least 95%, at least 96%, at least 97%, at least about 98%, or at least 99% to SEQ ID NO:3.

The nucleic acid molecule in various examples can be or comprise a cDNA that lacks one or more introns present in the naturally-occurring gene, or, alternatively, can include one or more introns not present in the naturally-occurring gene. The nucleic acid molecule in various examples can have a sequence that is not 100% identical to a naturally-occurring gene. For example, the nucleic acid molecule can include a mutation with respect to a naturally-occurring gene that reduces the activity of the encoded polypeptide or reduces expression of the mRNA or protein encoded by the gene.

The nucleic acid molecule in various examples can comprise a heterologous promoter operably linked to the sequence encoding a polypeptide that includes an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1, SEQ ID NO:2, and/or SEQ ID NO:3; and/or a nucleic acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:4. Alternatively or in addition, a nucleic acid molecule can comprise a vector that includes a sequence encoding a polypeptide that includes an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1, SEQ ID NO:2, and/or SEQ ID NO:3 (and/or a conservative variant of any of SEQ ID NOs:1-3) and/or a sequence that has at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:4.

This disclosure also provides constructs designed for attenuating expression of a gene encoding a TPR domain. The construct can be or comprise, in various examples, a sequence encoding a guide RNA of a CRISPR system, an RNAi construct, an antisense construct, a ribozyme construct, or a construct for homologous recombination, e.g., a construct having one or more nucleotide sequences having homology to a TPR domain-encoding gene as disclosed herein and/or sequences adjacent thereto in the native genome from which the gene is derived. For example, the construct can include at least a portion of a gene encoding a polypeptide having a TPR domain and/or having a DUF4470 domain, e.g., a sequence homologous to at least a portion of an gene that encodes a polypeptide that includes an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:1, SEQ ID NO:2, and/or SEQ ID NO:3.

The construct for gene attenuation can include, for example, at least a portion of the coding region, intron, 5'UTR, promoter region, or 3' UTR of a gene encoding a polypeptide having a TPR or DUF4470 domain (e.g., SEQ ID NO:1 or SEQ ID NO:2), and/or a polypeptide having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:1, SEQ ID NO:2 and/or SEQ ID NO:3, and/or at least a portion of a gene having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:4, in either sense or antisense orientation. In addition, such construct may include at least a portion of the coding region, intron, 5'UTR, promoter region, or 3' UTR of a gene encoding a polypeptide having any of SEQ ID NOs:1-3, and/or a conservative variant thereof.

In further examples a construct can be designed for the in vitro or in vivo expression of a guide RNA (e.g., of a CRISPR system) designed to target a gene having a sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to at least a portion of SEQ ID NO:4, or encoding a polypeptide having a TPR domain having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1, SEQ ID NO:2, and/or SEQ ID NO:3, and/or can include a sequence homologous to a portion of a gene encoding a polypeptide having a TPR domain and/or a DUF4470 domain, including, for example, an intron, a 5' UTR, a promoter region, and/or a 3' UTR.

In yet further examples, a construct for attenuating expression of a gene encoding a TPR domain-containing polypeptide can be a guide RNA or antisense oligonucleotide, where the sequence having homology to a transcribed region of a gene encoding a polypeptide having a TPR domain in antisense orientation.

Nucleic acid constructs for attenuating expression of a TPR domain-encoding gene and/or a gene encoding a polypeptide having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1, 2 and/or 3 can include, for example at least about 17, at least about 18, at least about 19, at least about 20, at least about 21, at least about 22, at least about 23, at least about 24, or at least about 25 nucleotides of sequence of a TPR domain-encoding gene and/or a gene encoding a polypeptide having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1, 2 and/or 3, and/or a gene having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to a portion of SEQ ID NO:4.

In one example, provided herein is a nucleic acid molecule having at least about 50%, at least about 55%, at least 60%, at least 65%, at least 70%, or at least 75%, at least 80%, at least 85%, at least 90%, or at least about 95% identity to at least a portion of SEQ ID NO:4, where the nucleic acid molecule encodes a guide RNA of a CRISPR system. The nucleic acid molecule can include, for example at least about 17, at least 18, at least 19, at least 20, at least 21, at least 22, at least 23, at least 24, or at least 25 nucleotides of sequence of a naturally-occurring TPR domain-containing gene, such as but not limited to SEQ ID NO:4.

In addition, provided herein are antisense, ribozyme, or RNAi constructs that include and/or are complementary and/or have specificity for at least a portion of a gene encoding a TPR domain and/or a polypeptide having at least about 65% identity to SEQ ID NO:1 and/or 2, and/or a gene having at least about 50%, at least 55%, at least 60%, at least 65%, at least 70%, at least 75%, at least 80%, at least 85%, at least 90%, at least 95%, at least 96%, at least 97%, at least 98%, or at least 99% identity to a portion of SEQ ID NO:4, in which a promoter, such as a heterologous promoter, is operably linked to the TPR domain-containing gene sequence and the TPR domain-containing gene sequence is in antisense orientation. In addition, provided herein are antisense, ribozyme, or RNAi constructs that include and/or are complementary and/or have specificity for at least a portion of a gene having at least about 65% identity to SEQ ID NO:4, and/or a gene having at least about 50%, at least 55%, at least 60%, at least 65%, at least 70%, at least 75%, at least 80%, at least 85%, at least 90%, at least 95%, at least about 96%, at least 97%, at least 98%, or at least about 99% identity to a portion of SEQ ID NO:4.

Further, provided herein are constructs for homologous recombination that include and/or are complementary and/or have specificity and/or target a nucleotide sequence from or adjacent to a naturally-occurring algal gene encoding a polypeptide having an amino acid sequence with at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:1, SEQ ID NO:2, and/or SEQ ID NO:3; and/or a gene localized to the Naga_100148 g8 locus; and/or a gene that comprises an ORF comprising a sequence having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:4. In some embodiments, the nucleotide sequence is juxtaposed with a heterologous nucleic acid sequence that can be, in non-limiting examples, a selectable marker or detectable marker gene. In some examples a construct for homologous recombination includes two nucleic acid sequences from or adjacent to a naturally-occurring algal gene encoding a polypeptide having an amino acid sequence with at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1, SEQ ID NO:2, and/or SEQ ID NO:3; a gene localized to the Naga_100148 g8 locus; and/or a gene that comprises an ORF comprising a sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:4, where the two sequences flank a heterologous sequence for insertion into the gene locus.

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof. "Transient transformation" is intended to mean that a polynucleotide is introduced into the organism and does not integrate into the genome or otherwise become established and stably inherited by successive generations.

Genetic transformation can result in stable insertion and/or expression of transgenes, constructs from either the nucleus or the plastid, and in some cases can result in transient expression of transgenes. The transformation methods can also be used for the introduction of guide RNAs or editing DNAs. Genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell*, 2010; and Gong et al., *J. Ind. Microbiol. Biotechnol.*, 2011). Non-limiting examples of such useful transformation methods include agitation of cells in the presence of glass beads or silicon carbide whiskers as reported by, for example, Dunahay, *Biotechniques*, 15(3):452-460, 1993; Kindle, *Proc. Natl. Acad. Sci. U.S.A.*, 1990; Michael and Miller, *Plant J.*, 13, 427-435, 1998. Electroporation techniques have been successfully used for genetic transformation of several microalgal species including *Nannochloropsis* sp. (see, e.g., Chen et al., *J. Phycol.*, 44:768-76, 2008), *Chlorella* sp. (see, e.g., Chen et al., *Curr. Genet.*, 39:365-370, 2001; Chow and Tung, *Plant Cell Rep.* Vol. 18, No. 9, 778-780, 1999), *Chlamydomonas* (Shimogawara et al., *Genetics*, 148: 1821-1828, 1998), and *Dunaliella* (Sun et al., *Mol. Biotechnol.* 30(3): 185-192, 2005), for example. Micro-projectile bombardment, also referred to as microparticle bombardment, gene gun transformation, or biolistic bombardment, has been used successfully for several algal species including, for example, diatoms species such as *Phaeodactylum* (Apt et al., *Mol. Gen. Genet.*, 252:572-579, 1996), *Cyclotella* and *Navicula* (Dunahay et al., *J. Phycol.*, 31:1004-1012, 1995), *Cylindrotheca* (Fischer et al., *J. Phycol.*, 35:113-120, 1999), and *Chaetoceros* sp. (Miyagawa-Yamaguchi et al., *Phycol. Res.* 59: 113-119, 2011), as well as green algal species such as *Chlorella* (El-Sheekh, *Biologia Plantarum*, Vol. 42, No. 2: 209-216, 1999), and *Volvox* species (Jakobiak et al., *Protist*, 155:381-93, 2004). Additionally, *Agrobacterium*-mediated gene transfer techniques can also be useful for genetic transformation of microalgae, as has been reported by, for example, Kumar, *Plant Sci.*, 166(3):731-738, 2004, and Cheney et al., *J. Phycol.*, Vol. 37, Suppl. 11, 2001. Conjugation with bacterial species has also been employed for transfer of genes and constructs to algae, as disclosed for example in US 2016/0244770, incorporated herein by reference.

A transformation vector or construct as described herein will typically comprise a marker gene that confers a selectable or scorable phenotype on target host cells, e.g., algal cells or may be co-transformed with a construct that includes a marker. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocidin, bleomycin (see, for example, Apt et al., 1996, supra; Fischer et al., 1999, supra; Fuhrmann et al., *Plant J.*, 19, 353-61, 1999, Lumbreras et al., *Plant J.*, 14(4):441-447, 1998; Zaslayskaia et al., *J. Phycol.*, 36:379-386, 2000), spectinomycin (Cerutti et al., *Genetics*, 145: 97-110, 1997; Doetsch et al., *Curr. Genet.*, 39, 49-60, 2001; Fargo, *Mol. Cell. Biol.*, 19:6980-90, 1999), streptomycin (Berthold et al., *Protist*, 153:401-412, 2002), paromomycin (Jakobiak et al., *Protist, supra*.; Sizova et al., *Gene*, 277: 221-229, 2001), nourseothricin (Zaslayskaia et al., 2000, supra), G418 (Dunahay et al., 1995, supra; Poulsen and Kroger, *FEBS Lett.*, 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paromomycin and neomycin resistance (Sizova et al., 2001, supra). Other fluorescent or chromogenic markers that have been used include luciferase (Falciatore et al., *J. Mar. Biotechnol.*, 1: 239-251, 1999; Fuhrmann et al., *Plant Mol. Biol.*, 2004; Jarvis and Brown, *Curr. Genet.*, 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.*, 1:165-169, 1994), β-galactosidase (Gan et al., *J. Appl. Phycol.*, 15:345-349, 2003; Jiang et al., *Plant Cell Rep.*, 21:1211-1216, 2003; Qin et al., *High Technol. Lett.*, 13:87-89, 2003), and green fluorescent protein (GFP) (Cheney et al., 2001, supra; Ender et al., *Plant Cell*, 2002, Franklin et al., *Plant J.*, 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.*, 18:778-780, 1999; Jarvis and Brown, *Curr. Genet.*, 317-321, 1991; Lohuis and Miller, *Plant J.*, 13:427-435, 1998). The SV40 promoter from simian virus has also reported to be active in several algae (Gan et al., *J. Appl. Phycol.*, 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.*, 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.*, 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.*, 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No.

8,318,482, incorporated by reference herein). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272:3413-3423, 2005), thus gene expression can be switched off or on when microalgal cells are grown in the presence of ammonium/nitrate. An ammonium-repressible *Nannochloropsis* promoter referred to as the "Ammonia repressible Nitrite/Sulfite Reductase" promoter is disclosed in US 2017/0073695, incorporated herein by reference. Additional algal promoters that can find use in the constructs and transformation systems provided herein include those disclosed in U.S. Pat. Nos. 8,835,419; 8,883,993; U.S. Patent Appl. Pub. No. US 2013/0023035; U.S. Patent Application Pub. No. US 2013/0323780; U.S. Patent Application Pub. No. US 2014/0363892, U.S. Patent Application Pub. No. US 2017/0152520, and U.S. Patent Application Pub. No. US 2017/0114107, all incorporated herein by reference in their entireties.

Host cells can be either untransformed cells or cells that are already transfected with at least one nucleic acid molecule. For example, an algal host cell that is engineered to have attenuated expression of a lipid regulator gene can further include one or more transgenes that may confer or contribute to any desirable trait, such as, but not limited to, increased production of biomolecules of interest, such as one or more proteins, pigments, alcohols, or lipids.

Methods of Producing Lipids

Also provided herein are methods of producing lipid by culturing a mutant microorganism as provided herein that has increased lipid productivity with respect to a control cell when cultured under the same conditions. The methods include culturing a mutant microorganism as provided herein in a suitable medium to produce lipid and recovering biomass or at least one lipid from the culture. The microorganism can in some examples be an alga, and the culture can be a photoautotrophic culture. Culturing can be in batch, semi-continuous, or continuous mode.

The mutant microorganism in some examples can be cultured in a medium that comprises less than about 5 mM ammonium, less than about 4.5 mM ammonium, less than about 4 mM ammonium, less than about 3.5 mM ammonium, less than about 3 mM ammonium, less than about 2.5 mM ammonium, less than about 2 mM ammonium, less than about 1.5 mM ammonium, less than or equal to about 1 mM ammonium, less than or equal to about 0.5 mM ammonium (e.g., less than 5 mM), or substantially no ammonium. The culture medium can include, for example, from about 0 to about 5 mM ammonium, from about 0 to about 4.5 mM ammonium, from about 0 to about 4.0 mM ammonium, from about 0 to about 3.5 mM ammonium, from about 0 to about 3 mM ammonium, from about 0 to about 2.5 mM ammonium, from about 0 to about 2.0 mM ammonium, from about 0 to about 1.5 mM ammonium, from about 0 to about 1.0 mM ammonium, from about 0 to about 0.5 mM ammonium, from about 0.2 to about 3 mM ammonium, from about 0.2 to about 2.5 mM ammonium, from about 0.2 to about 2 mM ammonium, from about 0.2 to about 1.5 mM ammonium, from about 0.2 to about 1 mM ammonium, from about 0.3 to about 2.5 mM ammonium, from about 0.3 to about 2 mM ammonium, from about 0.3 to about 1.5 mM ammonium, from about 0.3 to about 1 mM ammonium, from about 0.4 mM to about 2.5 mM ammonium, from about 0.4 to about 2 mM ammonium, or from about 0.4 mM to about 1.5 mM (e.g., 0-5 mM) ammonium. The microorganism can be cultured in a medium that includes nitrate, which in some examples may be substantially the sole nitrogen source in the culture medium or may be present in addition to less than about 5 mM ammonium, less than about 4.5 mM ammonium, less than about 4 mM ammonium, less than about 3.5 mM ammonium, less than about 3 mM ammonium, less than about 2.5 mM ammonium, less than about 2 mM ammonium, less than about 1.5 mM ammonium, less than or equal to about 1 mM ammonium, less than or equal to about 0.5 mM (e.g., less than 5 mM), or substantially no ammonium. Alternatively or in addition, the culture medium can comprises urea, which in some examples can be substantially the sole source of nitrogen in the culture medium.

The lipid producing microorganisms may be cultured in any suitable vessel(s), including flasks or bioreactors. In some examples, the mutant microorganism is an alga and is exposed to light for at least a portion of the culture period, in which the algae may be exposed to artificial or natural light (or natural light supplemented with artificial light). The culture comprising mutant algae that are deregulated in their response to low light may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc. Alternatively, an algal mutant can be cultured in continuous light.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. A microorganism as provided herein may be cultured for at least about one, at least about two, at least about three, at least about four, at least about five, at least about six, at least about seven at least about eight, at least about nine, at least about ten, at least about eleven at least about twelve, at least about thirteen, at least about fourteen, or at least about fifteen days, or at least about one, two three, four, five, six, seven, eight, nine, or ten weeks, or longer. The culturing can optionally be in a culture medium that is nutrient replete with respect to a control alga.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured photographically. When growing photographically, the algal strain can advantageously use light as an energy source. An inorganic carbon source, such as $CO_2$ or bicarbonate can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other products can vary and may be optimized to promote growth, propagation, or production of a product such as a lipid, protein, pigment, antioxidant, etc. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae; Culture Collection of Algae and Protozoa; and Katedra Botaniky.

The culture methods can optionally include inducing expression of one or more genes and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the microorganisms having increased lipid productivity can be cultured in a photobioreactor equipped with an artificial light source, and/or having one or more walls that is transparent enough to light, including sunlight, to enable, facilitate, and/or maintain acceptable microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally or alternately, mutant or recombinant photosynthetic microorganisms or host cells may be grown in ponds, canals, sea-based growth containers, trenches, raceways, channels, or the like, or combinations thereof. In such systems, the temperature may be unregulated, or various heating or cooling method or devices may be employed. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose with respect to the growth, proliferation, and/or survival of the microorganisms.

The mutant microorganisms can optionally include one or more non-native genes encoding a polypeptide for the production of a product, such as but not limited to a lipid.

The methods include culturing a mutant microorganism as provided herein, such as a mutant microorganism as provided herein that has increased lipid productivity with respect to a control cell when cultured under the same conditions to produce biomass or lipid. Lipids can be recovered from culture by recovery means known to those of ordinary skill in the art, such as by whole culture extraction, for example, using organic solvents or by first isolating biomass from which lipids are extracted (see, for example, Hussein et al. *Appl. Biochem. Biotechnol.* 175:3048-3057; Grima et al. (2003) *Biotechnol. Advances* 20:491-515). In some cases, recovery of fatty acid products can be enhanced by homogenization of the cells (Gunerken et al. (2015) *Biotechnol. Advances* 33:243-260). For example, lipids such as fatty acids, fatty acid derivatives, and/or triglycerides can be isolated from algae by extraction of the algae with a solvent at elevated temperature and/or pressure, as described in the co-pending, commonly-assigned U.S. patent publication No. US 2013/0225846 entitled "Solvent Extraction of Products from Algae", filed on Feb. 29, 2012, which is incorporated herein by reference in its entirety.

Biomass can be harvested, for example, by centrifugation or filtering. The biomass may be dried and/or frozen. Further products may be isolated from biomass, such as, for example, various lipids or one or more proteins. Also described herein is an algal biomass comprising biomass of lipid regulator mutant, such as any disclosed herein, such as but not limited to a lipid regulator mutant that includes a mutation in a gene encoding a polypeptide that has a TPR domain having at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to SEQ ID NO:1, and/or a mutation in a gene encoding a polypeptide having at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to SEQ ID NO:2. Also described herein is an algal biomass comprising biomass of lipid regulator mutant, such as any disclosed herein, such as but not limited to a lipid regulator mutant that includes a mutation in a gene encoding a polypeptide that has a DUF4470 domain having at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to SEQ ID NO:3.

Lysates of algal mutants as provided herein can be produced using methods known in the art. As nonlimiting examples, such methods can use enzymes (e.g., proteases or other cell wall digesting enzymes), chaotropic agents such as guanidinium or urea, detergents, for example in concentrations ranging from 0.1 to 5% or more, and/or physical disruption, including, but not limited to, grinding in a mortar and pestle (optionally using frozen cells), freeze-thawing, hypotonic lysis, sonication, bead-beating, heating, high pressure, cavitation, and the like, or any combination thereof. A lysate may optionally be a cleared lysate that can be a supernatant of lysed cells centrifuged at any g force, e.g., 1-100,000×g or more. Alternatively or in addition a lysate may be a filtered, dialyzed, or concentrated lysate.

Alternatively or in addition to any of the forgoing embodiments, the invention provides the following embodiments:

Embodiment 1 is a mutant microorganism that has attenuated expression of a gene or a disrupted gene encoding a polypeptide that comprises:
a TPR domain, optionally wherein the TPR domain has at least about 50%, at least 55%, at least 60%, at least 65%, at least 70%, at least 75%, at least 80%, at least 85%, at least 90%, at least 95%, at least 96%, at least 97%, at least 98%, or at least 99% identity to the amino acid sequence set forth in SEQ ID NO:1; and/or
a DUF4470 domain, optionally wherein the DUF4470 domain has at least about 50%, at least 55%, at least 60%, at least 65%, at least 70%, at least 75%, at least 80%, at least 85%, at least 90%, at least 95%, at least 96%, at least 97%, at least 98%, or at least 99% identity to the amino acid sequence set forth in SEQ ID NO:2;
an amino acid sequence that has at least about 50%, at least 55%, at least 60%, at least 65%, at least 70%, at least 75%, at least 80%, at least 85%, at least 90%, at least 95%, at least 96%, at least 97%, at least 98%, or at least 99% identity to the amino acid sequence set forth in SEQ ID NO:3;
wherein the mutant microorganism produces at least about 25% more lipid than a control microorganism; and/or exhibits increased partitioning of carbon to lipid with respect to the control microorganism; when the mutant microorganism and control microorganism are cultured under identical conditions, optionally wherein the control microorganism is a wild type microorganism.

Embodiment 2 is a mutant microorganism according to Embodiment 1, wherein the mutant microorganism comprises one or more mutations to or affecting the expression of a gene localized to the Naga_100148 g8 locus or a syntenic locus in a heterokont or algal species; and/or comprises one or more mutations affecting the expression of a gene comprising an open reading frame having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:4.

Embodiment 3 is a mutant microorganism according to Embodiment 1 or Embodiment 2, wherein the mutant microorganism produces at least about 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, or at least 200% more fatty acid methyl ester-derivatizable lipids (FAME lipids) than a control microorganism when the mutant microorganism and control microorganism are cultured under identical conditions and/or exhibits a FAME/TOC ratio at least 20%, at least 30%, at least 40%, at least 50%, at least 60%, at least 70%, at least 80%, at least 90%, at least 100%, at least 120%, at least 140%, at least 160%, at least 180%, at least 200%, at least 220%, at least 240%, at least 260%, at least 280%, or at least 300% higher than the FAME/TOC ratio of the control microorganism when the mutant microorganism and control microorganism are cultured under identical conditions.

Embodiment 4 is a mutant microorganism wherein the microorganism is an algal or heterokont species, optionally wherein the mutant microorganism is an algal species selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox* or optionally wherein the mutant microorganism is a heterokont selected from the group consisting of bacillariophytes, eustigmatophytes, xanthophytes, phaeophytes, chrysophytes, or raphidophytes, or optionally wherein the mutant microorganism is a heterokont selected from the group consisting of a Labyrinthulomycete species of *Labryinthula, Labyrinthuloides, Thraustochytrium, Schizochytrium, Aplanochytrium, Aurantiochytrium, Oblongichytrium, Japonochytrium, Diplophrys,* or *Ulkenia.*

Embodiment 5 is a mutant microorganism according to any of Embodiments 1-4, wherein the identical culture conditions include: a culture medium comprising comprising less than 2 mM ammonium, optionally a culture medium in which nitrate is the sole nitrogen source and/or the culture conditions are any of batch, semi-continuous, or continuous culture conditions.

Embodiment 6 is a mutant microorganism according to Embodiment 5, wherein the mutant microorganism is an alga and the culture conditions are photoautotrophic.

Embodiment 7 is a mutant microorganism according to any of Embodiments 1-6, wherein the mutant microorganism is a classically-derived mutant or a genetically engineered mutant, wherein any one or more of the following are true:
the mutant microorganism is a knockdown mutant, optionally generated using a Cas/CRISPR system, an RNAi construct, a ribozyme construct, or an antisense construct;
the mutant microorganism is a knockdown mutant wherein the mutation disrupts the gene by partial or total deletion, truncation, frameshifting, and/or insertional mutation into a noncoding region of the gene;
the mutant microorganism is a knockout mutant, optionally produced by site directed homologous recombination, a meganuclease, a zinc finger nuclease, a Transcription Activator-Like Effector Nuclease (TALEN) system, and/or a Cas/CRISPR system; and
the mutant microorganism is a knockout mutant, wherein the mutation disrupts the gene by partial or total deletion, truncation, frameshifting, and/or insertional mutation.

Embodiment 8 is a mutant microorganism according to any of Embodiments 1-7, wherein the mutant microorganism comprises at least one additional genetic modification that confers herbicide resistance, toxin resistance, enhanced growth properties, enhanced photosynthetic efficiency, enhanced lipid production or accumulation, and/or production of particular lipids.

Embodiment 9 is a method of producing lipids including culturing a mutant microorganism according to any of Embodiments 1-8 in a culture medium, wherein the mutant microorganism produces lipid, and optionally isolating lipid from the microorganism, the culture medium, or both, optionally wherein the microorganism is cultured using batch, continuous, or semi-continuous culture conditions.

Embodiment 10 is a mutant microorganism according to Embodiment 9, wherein the microorganism is an alga and the culturing is under photoautotrophic conditions.

Embodiment 11 is a mutant microorganism according to Embodiment 9, wherein the microorganism is a Labyrinthulomycete and the culturing is under heterotrophic conditions.

Embodiment 12 is a guide RNA of a CRISPR system, wherein the guide RNA includes a sequence corresponding to the target sequence set forth in SEQ ID NO:7, wherein the guide RNA is a chimeric guide or the guide RNA does not include a tracr sequence.

Embodiment 13 is a nucleic acid construct for homologous recombination, wherein the construct includes a nucleotide sequence from or adjacent to a naturally-occurring algal gene encoding a polypeptide having an amino acid sequence with at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1, SEQ ID NO:2, and/or SEQ ID NO:3; a gene localized to the Naga_100148 g8 locus; and/or a gene that comprises an ORF comprising a sequence having at least about 50%, at least 55%, at least 60%, at least 65%, at least 70%, at least 75%, at least 80%, at least 85%, at least 90%, at least 95%, at least 96%, at least about 97%, at least 98%, or at least about 99% identity to SEQ ID NO:4.

Embodiment 14 is a nucleic acid construct is for expression of an antisense RNA, shRNA, microRNA, or ribozyme and includes a nucleotide sequence complementary to at least a portion of a naturally-occurring gene encoding a polypeptide having an amino acid sequence with at least about 50%, at least 55%, at least 60%, at least 65%, at least 70%, at least 75%, at least a 80%, at least 85%, at least 90%, at least 95%, at least 96%, at least 97%, at least 98%, or at least about 99% identity to SEQ ID NO:1, SEQ ID NO:2, and/or SEQ ID NO:3; a gene localized to the Naga_100148 g8 locus; and/or a gene that comprises an ORF comprising a sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:4.

Embodiment 15 is a nucleic acid molecule encoding a guide RNA of a CRISPR, wherein the guide RNA comprises at least a portion of a naturally-occurring algal gene encoding a polypeptide having an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1, SEQ ID NO:2, and/or SEQ ID NO:3; a gene localized to the Naga_100148 g8 locus; and/or a gene that comprises an ORF comprising a sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:4.

Embodiment 16 is a method for producing a mutant microorganism disclosed herein are provided in which a mutant microorganism is produced by introducing into a microorganism one or more mutations and/or one or more agents that attenuates the expression of a polypeptide comprising a TPR domain, wherein the one or more mutations affects the expression of a polypeptide comprising the amino acid sequence of SEQ ID NO:1, SEQ ID NO:2, and/or SEQ ID NO:3; a gene localized to the Naga_100148 g8 locus; or a gene comprising an open reading frame that comprises the nucleotide sequence of SEQ ID NO:4, optionally wherein the one or more agents is selected from the group consisting of antisense RNA, RNAi, shRNA, microRNA, ribozyme, a component of a Cas/CRISPR system and/or a component of a Transcription Activator-Like Effector Nuclease (TALEN) system.

Other embodiments are also contemplated herein, as would be understood by one of ordinary skill in the art. Certain embodiments are further described in the following examples. These embodiments are provided as examples only and are not intended to limit the scope of the claims in any way.

All references cited herein are incorporated by reference in their entireties. All headings are for the convenience of the reader and do not limit the invention in any way. References to aspects or embodiments of the invention do not necessarily indicate that the described aspects may not be combined with other described aspects of the invention or features of other aspects of the invention.

EXAMPLES

Media Used in Examples

PM066 medium includes 8.8 mM nitrate as the sole nitrogen source and 0.417 mM phosphate ($PO_4$) along with trace metals and vitamins in Instant Ocean salts. PM066 media was made by adding 5.71 ml of a 1.75 M $NaNO_3$ stock solution (148.7 g/L), and 5.41 ml of a 77 mM $K_2HPO_4.3H_2O$ stock solution (17.57 g/L) to 981 mls of Instant Ocean salts solution (35 g/L) along with 4 ml of Chelated Metals Stock Solution and ml of 4 ml Vitamin Stock Solution. Chelated Metals Stock Solution was prepared by adding to 400 mls of water 2.18 g $Na_2EDTA.2H_2O$; 1.575 g $FeCl_3.6H_2O$; 500 µl of 39.2 mM stock solution (0.98 g/100 ml) $CuSO_4.5H_2O$; 500 µl of 77.5 mM stock solution (2.23 g/100 ml) $ZnSO_4.7H_2O$; 500 µl of 42.0 mM stock solution (1.00 g/100 ml) $CoCl_2.6H_2O$; 500 µl of 910.0 mM stock solution (18.0/100 ml) $MnCl_2.4H_2O$; 500 µl of 26.0 mM stock solution (0.63 g/100 ml) $Na_2MoO_4.2H_2O$; bringing up to 500 ml final volume, and filter sterilizing. Vitamin Stock Solution was prepared by adding to 400 mls of water 0.05 g Thiamine HCl; 500 µl of 0.37 mM stock solution (0.05 g/100 ml) of cyanocobalamin; and 2.5 ml of 0.41 mM stock solution (0.01 g/100 ml) of biotin, bringing up to a final volume of 500 mls, and filter sterilizing.

PM067 medium includes no nitrogen source (no nitrate, ammonium, or urea), and includes 0.417 mM phosphate ($PO_4$) along with trace metals and vitamins in Instant Ocean salts. PM067 media was made by adding 5.41 ml of a 77 mM $K_2HPO_4.3H_2O$ stock solution (17.57 g/L) to 987 mls of Instant Ocean salts solution (35 g/L) along with 4 ml of Chelated Metals Stock Solution and ml of 4 ml Vitamin Stock Solution. Chelated Metals Stock Solution was prepared by adding to 400 mls of water 2.18 g Na$_2$EDTA.2H$_2$O; 1.575 g FeCl$_3$.6H$_2$O; 500 μl of 39.2 mM stock solution (0.98 g/100 ml) CuSO$_4$.5H$_2$O; 500 μl of 77.5 mM stock solution (2.23 g/100 ml) ZnSO$_4$.7H$_2$O; 500 μl of 42.0 mM stock solution (1.00 g/100 ml) CoCl$_2$.6H$_2$O; 500 μl of 910.0 mM stock solution (18.0/100 ml) MnCl$_2$.4H$_2$O; 500 μl of 26.0 mM stock solution (0.63 g/100 ml) Na$_2$MoO$_4$.2H$_2$O; bringing up to 500 ml final volume, and filter sterilizing. Vitamin Stock Solution was prepared by adding to 400 mls of water 0.05 g Thiamine HCl; 500 μl of 0.37 mM stock solution (0.05 g/100 ml) of cyanocobalamin; and 2.5 ml of 0.41 mM stock solution (0.01 g/100 ml) of biotin, bringing up to a final volume of 500 mls, and filter sterilizing.

PM074 is a nitrogen replete medium that includes nitrate as the sole nitrogen source ("nitrate-only") that is 10×F/2 made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (35 g/L) (Aquatic Eco Systems, Apopka, Fla.). Proline A and Proline B together include 8.8 mM NaNO$_3$, 0.361 mM NaH$_2$PO$_4$.H$_2$O, 10×F/2 Trace metals, and 10×F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

PM124 medium is PM074 supplemented with 5 mM Ammonium and 10 mM HEPES pH 8.0. It is made by adding 10 mls of 1 M HEPES pH 8 and 5 mls of NH$_4$Cl to the PM074 recipe (final volume of 1 L). Additional media with controlled ammonium levels was made by adjusting the ammonium concentration of PM074 and adding additional Hepes buffer.

PM066, PM074, and PM124 media are nitrogen replete and nutrient replete with respect to wild type *Nannochloropsis*.

Example 1

Identification of a Polypeptide Downregulated During Nitrogen Starvation

Various strains of *Nannochloropsis* accumulate high levels of triacylglycerols (TAG) storage lipid during nitrogen deprivation and correlations between increased TAG production and correlations between TAG accumulation and presumed underlying changes in gene expression in different metabolic pathways leading to TAG synthesis have been reported (Radakovits et al. (2012) *Nat Commun* 3:686; Li et al. (2014) *The Plant Cell* 26:1645-1665; Corteggiani Carpinelli et al. (2014) *Mol Plant* 7:1645-1665). To identify genes encoding regulators that influence lipid biosynthesis and accumulation, the early transcriptional response of *Nannochloropsis* cells subjected to N-deprivation (+N) was analyzed. A comparative transcriptomics experiment was performed in which the RNA transcript levels of genes of *Nannochloropsis gaditana* cells under nitrogen starvation, during which *Nannochloropsis* induces storage lipid biosynthesis, were compared with the levels of RNA transcripts of the same strain of *Nannochloropsis gaditana* grown under identical conditions except that the amount of nitrogen in the growth medium was not limiting.

Wild type *N. gaditana* (WT-3730) cells were grown in nutrient replete medium under a 16 hour light (120 pE)/8 hour dark cycle to light limitation (to O.D. of 1.25) and at the beginning of the photoperiod were spun down and resuspended in either nitrogen replete medium PM066 or culture medium lacking a nitrogen source ("nitrogen deplete" or "—N" medium PM067) and incubated under the provided light conditions. RNA was isolated from samples removed at various time intervals after resuspension of the cells in nitrogen replete (+N) or nitrogen deplete (−N) medium. Lipid accumulation was determined from samples taken throughout the assay. Lipid accumulation (measured as FAME as described in Example 3) was indistinguishable between nitrogen deplete and nitrogen replete cultures at the 3 h timepoint, but at 10 h FAME accumulation in the nitrogen deplete culture was double that of the nitrogen replete culture. Treatments were performed in biological triplicates. Under the assumption that transcriptional changes should precede metabolic changes, the 3 h timepoint was selected for mRNA sequencing. Two samples for each treatment were sequenced.

RNA was isolated by spinning down 10 mLs of each algal cell culture (4000×g for 5 minutes) and decanting the supernatant. The pellets were resuspended in 1.8 mL Buffer A (5 mL TLE Grinding Buffer, 5 mL phenol, 1 mL 1-bromo-3-chloropropane and 20 mercaptoethanol, where TLE Grinding Buffer includes 9 mL of 1M Tris pH 8, 5 mL of 10% SDS, 0.6 mL of 7.5 M LiCl, and 450 μl 0.5 M EDTA in a final volume of 50 mL) and transferred to 2 mL microcentrifuge tubes containing approximately 0.5 mL of 200 μm zirconium beads. The tubes were vortexed vigorously for 5 min at 4° C. and then centrifuged for 2 min at 11.8×g. The aqueous layers were then removed and pipetted into new 2 mL tubes, to which 1 mL 25:24:1 phenol extraction buffer (25 mL phenol pH 8.1; 24 mL 1-bromo-3-chloropropane, and 1 mL isoamyl alcohol) was added. The tubes were shaken vigorously and centrifuged for 2 min at 11.8×g. After centrifugation, the aqueous layer was removed and pipetted into new 2 mL centrifuge tubes, to which 1 ml 1-bromo-3-chloropropane was added. The tubes were shaken and again centrifuged for 2 min at 11.8×g. The aqueous layer was removed to a new tube and 0.356 volumes of 7.5 M LiCl were added. The tubes were inverted 10-12 times and stored at −20° C. overnight. The next day, samples were allowed to come to room temperature without mixing and were centrifuged at 16,000×g for 30 minutes. The supernatants were removed and the pellets were washed with 1 mL of ice cold 80% ethanol. The tubes were centrifuged for 30 min at 16,000×g and allowed to air dry after the supernatants had been removed. Finally, the RNA pellets were resuspended in 50 μl ultrapure water. The RNA quality was assessed by on-chip gel electrophoresis using an Agilent 2100 Bioanalyzer and RNA6000 LabChip according to manufacturer instructions.

Next-generation sequencing libraries were prepared from the isolated RNA utilizing the TruSeq Stranded mRNA Sample Prep Kit (Illumina, San Diego, Calif.) following manufacturer instructions. The TruSeq libraries were sequenced using sequencing-by-synthesis (Illumina MiSeq) to generate 100 bp paired-end reads using the mRNA-Seq procedure (described in Mortazavi et al. (2008) *Nature Methods* 5:621-628). Mappable reads were aligned to the *N. gaditana* reference genome sequence using TopHat (tophat.cbcb.umd.edu/). Expression levels were computed for every annotated gene using the Cuffdiff component of the Cufflinks software (cufflinks.cbcb.umd.edu). TopHat and Cufflinks are described in Trapnell et al. (2012) *Nature Protocols* 7: 562-578. Differential expression analysis was performed using the R package edgeR (McCarthy et al. (2012) *Nucl. Acids Res.* 40:doi:10/1093/nar/gks042)). Expression levels in units of fragments per kilobase per million (FPKM) were reported for every gene in each sample using standard parameters. FPKM is a measure of relative transcriptional levels that normalizes for differences in transcript length.

A gene encoding a TPR domain containing protein (at locus Naga_100148 g8, referred to herein as the TPR-6029 gene) was identified as being differentially expressed between the N-replete and N-deplete culture conditions. This gene (cDNA sequence provided as SEQ ID NO:4) encodes a polypeptide (SEQ ID NO:3) having a TPR (Tripentacopeptide repeat) domain (SEQ ID NO:1) and a domain of unknown function (DUF4470) (pfam IPR027974; SEQ ID NO:2). A diagram of the polypeptide of SEQ ID NO:3 is provided in FIG. 1.

Example 2

Knockout of Gene Encoding a TPR Domain Containing Protein (Naga_100148 G8) in *Nannochloropsis*

Transgenic algal strains of *Nannochloropsis gaditana* were created in which the gene encoding the TPR domain containing protein was functionally ablated or knocked out by targeted mutagenesis. The wild type *Nannochloropsis gaditana* strain is designated WT-3730. The knockout mutants were generated using CRISPR technology.

Figure 2:
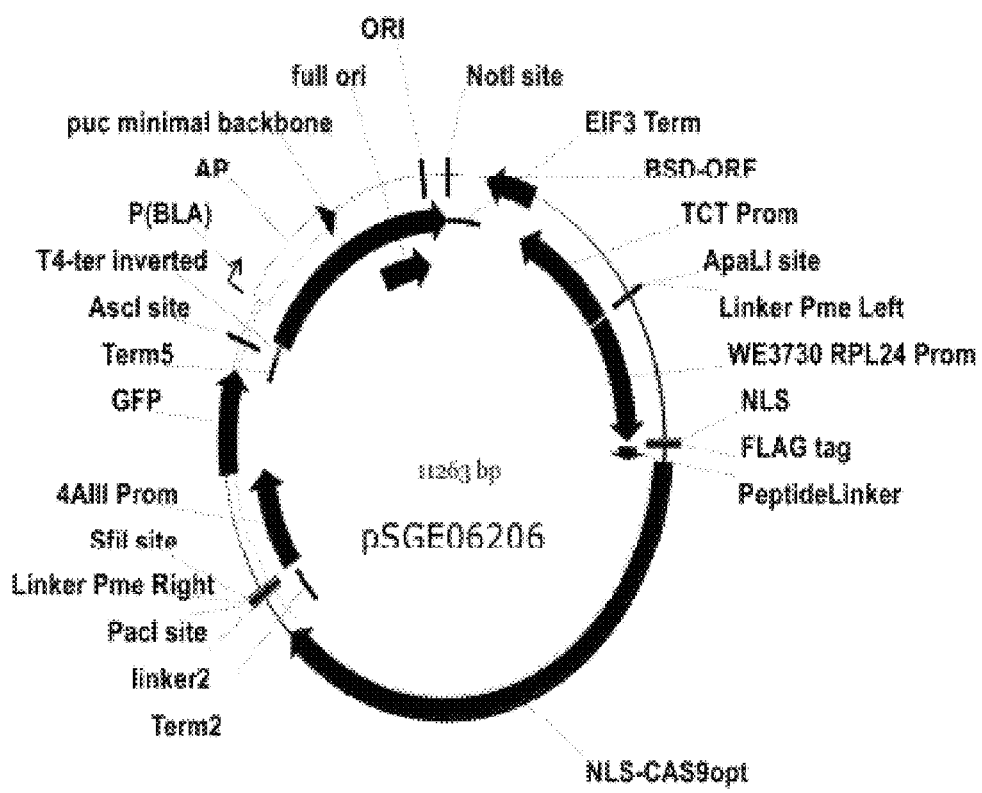
FIG. 2 is a schematic map of vector pSGE-6206 used to introduce Cas9 into the *N. gaditana* wild type strain WT-3730 to generate Cas9 Editor line GE-13038.

Knock-out mutants were made using a high efficiency *Nannochloropsis* Cas9-expressing Editor line as disclosed in co-pending application publication US 2017/0073695 "Compositions and Methods for High Efficiency In Vivo Genome Editing", filed Dec. 31, 2015, naming inventors John Verruto and Eric Moellering. Strain GE-6791, which expresses a gene encoding the *Streptococcus pyogenes* Cas9 nuclease, was used as a host for transformation with a chimeric guide RNA and donor DNA for insertional knockout. Strain GE-6791 was produced by transforming wild type *Nannochloropsis gaditana* strain WT-3730 with the vector pSGE-6206 (SEQ ID NO:6; FIG. 2). included the following three elements: 1) a Cas9 expression cassette which contained a Cas9 gene from *Streptococcus pyogenes* codon optimized for *N. gaditana* (SEQ ID NO:7) that included sequences encoding an N-terminal nuclear localization signal (SEQ ID NO:8), followed by a FLAG tag (SEQ ID NO:9), and peptide linker (together provided as SEQ ID NO:10), driven by the *N. gaditana* RPL24 promoter (SEQ ID NO:11) and terminated by the *N. gaditana* bidirectional terminator 2 (SEQ ID NO:12); 2) a selectable marker expression cassette, which contained the blasticidin S deaminase gene from *Aspergillus terreus* codon optimized for *N. gaditana* (SEQ ID NO:13), driven by the *N. gaditana* TCTP promoter (SEQ ID NO:14) and followed by the EIF3 terminator (SEQ ID NO:15); and 3) a GFP reporter expression cassette, which contained the TurboGFP gene (Evrogen, Moscow, Russia) codon optimized for *N. gaditana* (SEQ ID NO:16), driven by the *N. gaditana* 4A-III promoter (SEQ ID NO:17) and followed by the *N. gaditana* bidirectional terminator 5 (SEQ ID NO:18). Transformation was essentially as disclosed in published U.S. application US 2014/0220638 ("Algal mutants having a locked-in high light acclimated phenotype," filed Dec. 6, 2013).

The transformation mixture was plated onto PM074 agar medium containing 100 mg/L of blasticidin. Resulting colonies were patched onto selection media for analysis and archiving. A small amount of biomass was taken from the patches and completely resuspended in 300 µl of 1× Instant Ocean Salts solution (Aquatic Eco Systems; Apopka, Fla.). Care was taken to not add too much biomass so that a light green resuspension was obtained. This suspension was directly analyzed by flow cytometry using a BD Accuri C6 flow cytometer (BD Biosciences, San Diego, Calif.), using a 488 nm laser and 530/10 nm filter to measure GFP fluorescence per cell. 10,000-30,000 events were recorded for each sample using the slow fluidics setting. A strain having a single fluorescence peak that was shifted to a fluorescence level higher than that demonstrated by wild-type cells and also demonstrating Cas9 protein expression by Western, referred to herein as GE-13038, was selected as a Cas9 Editor strain and used in mutant generation by CRISPR/Cas9 genome editing as disclosed herein.

The gene encoding the TPR domain containing protein ("TPR-6029" gene encoding SEQ ID NO:3) was targeted for disruption using Cas9-mediated genome editing. Briefly, a Hygromycin resistance expression cassette was targeted to insert into the portion of the gene encoding the domain of unknown function (DUF4470) (FIG. 1). To produce a chimeric guide RNA for targeting of the Naga_100148 g8 gene for disruption, two DNA constructs were made (SGI-DNA, La Jolla, Calif.) for producing guide RNAs in which the DNA molecule included the sequence of a chimeric guide engineered downstream of a T7 promoter. In the first construct, the chimeric guide sequence included a 23 bp target sequence (SEQ ID NO:5, which includes the PAM sequence) homologous to a sequence within the Naga_100148 g8 gene sequence that encoded the TPR domain that was upstream of an *S. pyogenes* Cas9 PAM sequence (NGG), and also included the transactivating CRISPR RNA (tracr) sequence. The chimeric guide sequence was synthesized by first making a DNA template made up of complementary DNA oligonucleotides that were annealed to create a double-stranded DNA template which was used in in vitro transcription reactions using the MEGAshortscript™ T7 Kit (Life Technologies, Carlsbad, Calif. #AM1354M) according to the manufacturer's instructions to synthesize the guide RNA. The resulting RNA was purified using Zymo-Spin™ V-E columns (Zymo Research #C1024-25) according to the manufacturer's protocol.

The donor fragment for insertion into the targeted Naga_100148 g8 locus included a selectable marker cassette that included the hygromycin resistance gene (HygR, SEQ ID NO:19) downstream of the *N. gaditana* EIF3 promoter (SEQ ID NO:20) and followed by *N. gaditana* bidirectional terminator 2 (SEQ ID NO:12), with the entire promoter-hygromycin resistance gene-terminator sequence flanked by 27 base pair identification sequences on the 5' (SEQ ID NO:21) and 3' (SEQ ID NO:22) ends to yield the DNA fragment referred to as the "Hyg Resistance Cassette Naga_100148 g8" (SEQ ID NO:23).

For targeted knockout of the gene at the Naga_100148 g8 locus, Cas9 Editor line GE-13038 was transformed by electroporation using 5 µg of purified chimeric guide RNA targeting the gene and 1 µg of the selectable donor DNA (Hyg Resistance Cassette Naga_100148 g8; SEQ ID NO:23) essentially as described in US 2014/0220638, incorporated herein by reference. Following electroporation, cells were plated on PM124 agar media containing hygromycin to select for transformants that incorporated the hygromycin resistance cassette. Transformants were patched onto a fresh plate and screened by colony PCR for insertion of the donor fragment into the gene at the Naga_100148 g8 locus.

For colony PCR screening, a small amount of cells from a colony to be screened was suspended into 100 µl of 5% Chelex 100 Resin (BioRad)/TE solution and the suspension was boiled for 10 minutes at 99° C., after which the tubes were briefly spun. One microliter of the lysate supernatant was added to a PCR reaction mix, in which the PCR mixture and reactions were set up and performed according to the QIAGEN Fast Cycling PCR Master Mix Protocol from the manufacturer (Handbook available at qiagen.com; Qiagen GmbH, Germany) The primers used to detect insertion of the donor fragment into the targeted Naga_100148 g8 locus were SEQ ID NO:24 and SEQ ID NO:25. The PCR-based colony screening identified a knockout strain of the TPR-6029 gene, GE-15360, which included the cas9-directed insertion of the donor fragment inserted into the target site (denoted by an arrow in FIG. 1). This knockout insertion mutant was further tested in productivity assays.

Example 3

Naga_100148 G8 Knockout Mutant in Batch Productivity Assay

The mutant strains were assessed in a batch productivity assay in nitrogen replete medium PM074 that included 8.8 mM nitrate as the sole nitrogen source available to the cells in the absence of any reduced carbon source that could support algal growth (i.e., the productivity assay was conducted under photoautotrophic conditions). After inoculation, engineered knockout strains and wild type strain WT-3730 were grown in triplicate cultures in a batch assay in 75 cm² rectangular tissue culture flasks containing 175 ml of PM074 medium for seven days. Under these conditions, nitrogen begins to become limiting in the culture medium on approximately Day 3, with the concentration of nitrogen in the culture medium continuing to drop throughout the remainder of the assay. The flasks were positioned with their narrowest "width" dimension against an LED light. The culture flasks were masked with an opaque white plastic to provide a 21.1 cm² rectangular opening for irradiance to reach the cultures. Incident irradiance was programmed at a 16 h light:8-hour dark cycle where a linear ramp up of irradiance from 0 to 1200 uE and then a linear ramp down in irradiance from 1200 to 0 uE over a 4 h period. Deionized $H_2O$ was added to the cultures daily to replace evaporative losses. The temperature of the cultures was regulated by a water bath set at 25° C. Cultures were inoculated at $OD_{730}$ of 0.5 on day 0 and samples (5 mls) were removed on days 3, 5, and 7 for assessing cell density and fatty acid methyl esters (FAME) as a measure of lipid. Sampling was done 30 minutes prior to the end of the light cycle.

FAME analysis was performed on 2 mL samples that were dried using a GeneVac HT-4X. To each of the dried pellets the following were added: 500 µL of 500 mM KOH in methanol, 200 µL of tetrahydrofuran containing 0.05% butylated hydroxyl toluene, 40 µL of a 2 mg/ml C11:0 free fatty acid/C13:0 triglyceride/C23:0 fatty acid methyl ester internal standard mix and 500 µL of glass beads (425-600 µm diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 µL of 10% boron trifluoride in methanol was added to the samples prior to heating at 80° C. for 30 minutes. The tubes were allowed to cool prior to adding 2 mL of heptane and 500 µL of 5 M NaCl. The samples were vortexed for five minutes at 2K rpm and finally centrifuged for three minutes at 1K rpm. The heptane layer was sampled using a Gerstel MPS Autosampler. Quantitation used the 80 µg of C23:0 FAME internal standard. The samples were run on an Agilent 7890A gas chromatography system using a J&W Scientific 127-3212 DB-FFAP, 10 m×100 µm×100 nm column and an FID detector at 260° C. The flow rate was 500 µL/minute using $H_2$ as a carrier with constant flow control. The oven was set at 100° C. for 0.98 mM, then 15.301° C./minute to 230° C. and held for 1.66 mM The inlet contained a 4 mm glass wool packed liner (Agilent P/N 5183-4647), and was set at 250° C. and used a split ratio of 40:1. The injection volume was 900 nL.

Figure 3:
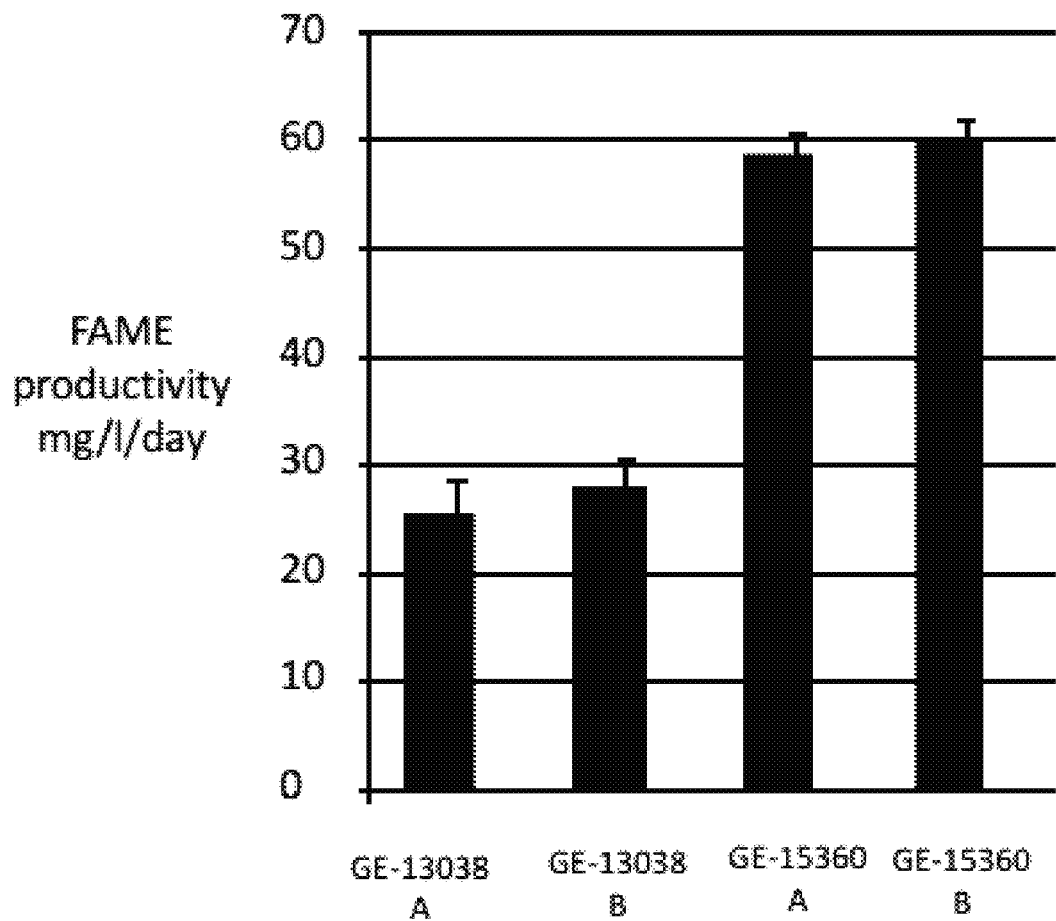
FIG. 3 is a graph showing average daily FAME productivity over the seven day batch assay for *N. gaditana* strain GE-15360 (a knockout of the TPR-6029 gene at the Naga_100148 g8 locus) compared to the parental control strain GE-13038 (Cas9 mother strain). "A" and "B" refer to the two culture replicates.

The results of the batch productivity assay are provided in FIG. 3. The amount of FAME produced by mutant strain GE-15360 was more than 2-fold the amount produced by the parental control strain GE-13038 (Cas9 Editor strain).

Figure 4:
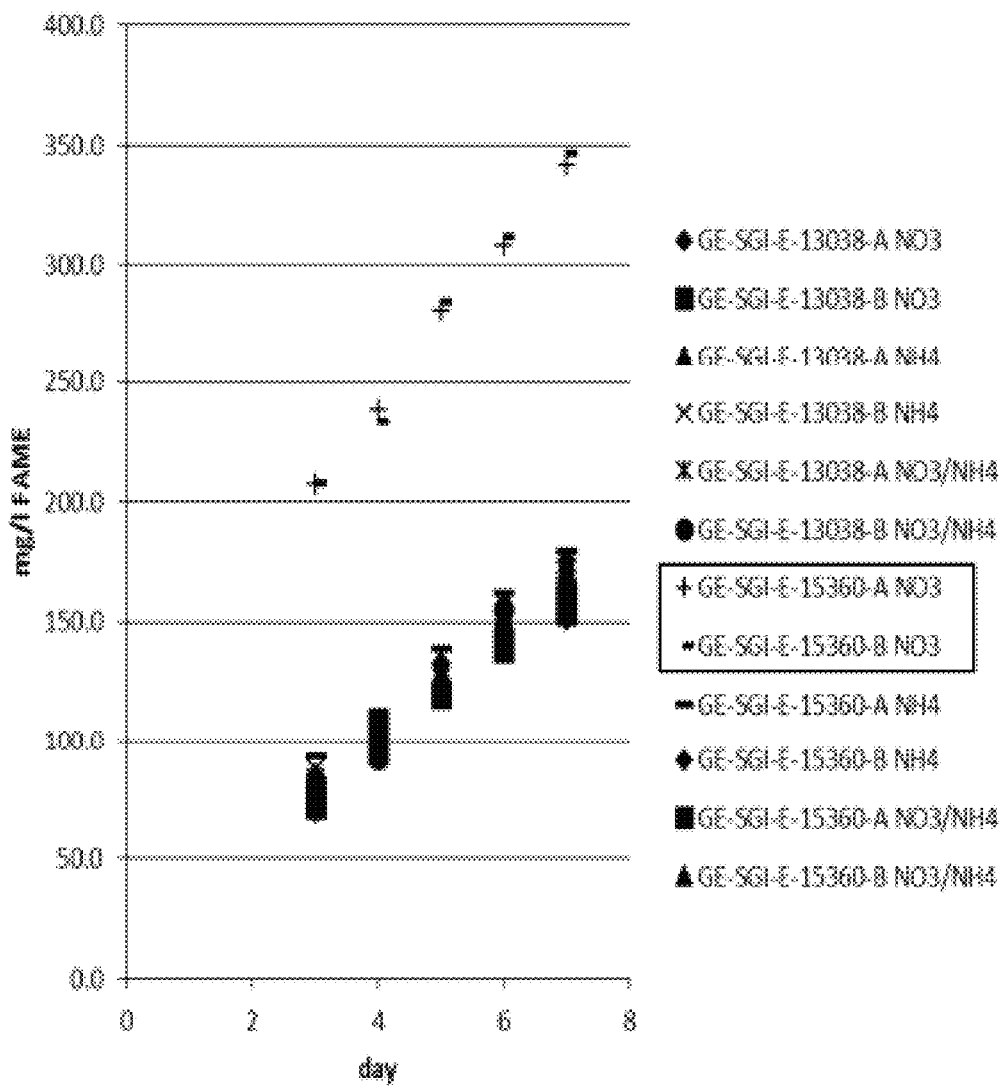
FIG. 4 is a graph showing the daily amount of FAME present in the *N. gaditana* cultures grown in batch assay in the TPR-6029 knockout mutant and parental Cas9+ strain GE-13038 in medium that included only nitrate as well as medium that included either ammonium only or nitrate plus ammonium.

A follow-up experiment showed that the lipid induction was repressed by ammonium (5 mM) in the growth medium (FIG. 4). In this assay, batch cultures includes either nitrate only, nitrate plus ammonium, or ammonium only as a nitrogen source. The parental Cas9+ strain showed essentially identical amounts of FAME produced on days 3-7 of the assay, regardless of the nitrogen source. In contrast, the TRP-6029 knockout mutant GE-15360 showed markedly increased FAME production with respect to the parental Editor line GE-13038 on each day of the assay when grown on nitrate-only medium. The presence of ammonium in the culture medium completely suppressed the increased lipid productivity of the mutant however. Where ammonium was present, the lipid production of TRP-6029 knockout strain GE-15360 was essentially identical to that of the parental strain that did not include a mutated TPR-6029 gene.

Example 4

Growth and Lipid Biosynthesis of the Knockout Mutant in Semi-Continuous Culture

Knockout strain GE-15360 was also assayed in the semi-continuous productivity assay. In the continuous productivity assay PM074 (nitrate only) medium in a 225 cm² flask was inoculated with *Nannochloropsis* seed culture so that the initial 550 ml (inoculated final volume) culture had an initial $OD_{730}$ of 0.15. A typical dilution used approximately 150 mls of starter culture in PM124 medium (containing 5 mM ammonium) which was brought up to 550 mls using PM074 medium, such that the starting concentration of ammonium in the semi-continuous assay was less than 1.5 mM. Daily dilutions with PM074 medium further reduced the ammonium concentration as the assay progressed. Three cultures were initiated per strain. The flasks included stir bars and had stoppers having tubing connected with syringe filters for delivering $CO_2$ enriched air (1% $CO_2$, flow rate, 100 ml per min) that was bubbled through the cultures. The flasks were set on stir plates set to 450 rpm. The flasks were aligned with the width (narrowest dimension) against an LED light bank that was programmed with a light/dark cycle and light profile that increased until "solar noon" and then declined to the end of the light period. The "depth" dimension of the flasks, extending back from the light source, was 13.7 cm. Taking into account the positioning of the flasks the farthest distance of the cells in the flasks from the surface of the light source was approximately 15.5 cm. The light profile was designed to mimic a spring day in Southern California: 16 h light: 8 h dark, with the light peaking at approximately 2000 uE. The cultures were diluted daily at the middle (peak) of the light period by removing 30% (150 ml) of the culture volume and replacing it with fresh PM074 media diluted (66 ml di $H_2O$ to 1 L PM074 medium) to adjust for the increase in salinity due to evaporation occurring in the cultures. Samples for FAME and TOC analysis were taken from the culture removed for the dilution. Continuous assays were typically run for 7-14 days, and averages of three cultures for each sample were obtained. Tables 1-3 show the results of FAME and TOC analysis of knockout and wild type cultures run in the semi-continuous assay. Averages of three cultures are provided with the standard deviation of each value in parentheses.

Figure 5:
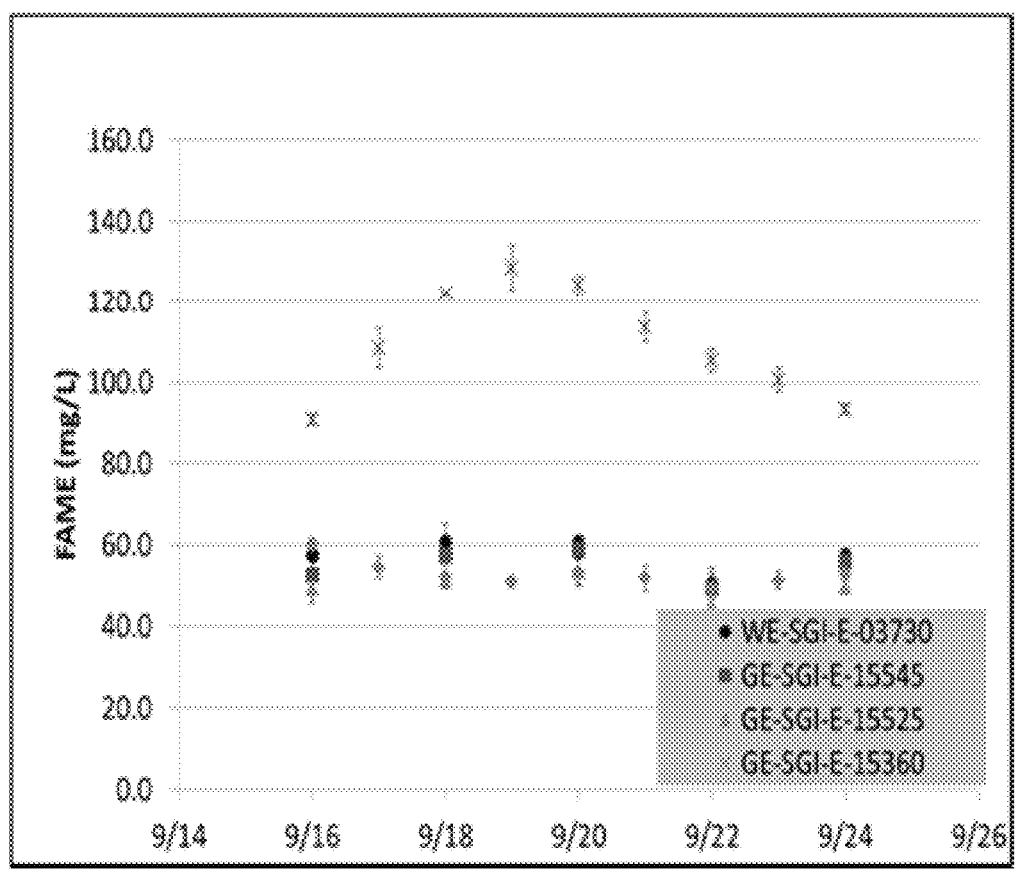
FIG. 5 shows daily FAME production by *N. gaditana* TPR-6029 knockout mutant GE-15360 versus wild type strain WT-3730 in the semicontinuous assay. The TPR knockout showed higher levels of FAME produced on each day of the 8 day assay. Strains GE-15545 and GE15525 were genetically engineered strains having modifications unrelated to the TPR-6029 gene.

In the semi-continuous assay, performed with nitrate-only culture medium, the GE-15360 knockout mutant demonstrated a higher FAME productivity with respect to the wild type strain, with daily productivities ranging from about 7.4% to about 115.6% more than the FAME productivities of the wild type cells (Table 1). This can also be seen in the graph of FIG. 5, in which the TRP-6029 mutant (GE-15360) has consistently higher fame produced on a daily basis than the wild type strain WT-3730. (Two other strains in the assay are not related to the TRP-6029 mutant.) Biomass (TOC) accumulation by the GE-15360 knockout mutant was, however, surprisingly greater than wild type cells (Table 2). The increased partitioning of carbon to lipids was clear from the FAME/TOC ratio of the GE-15360 knockout mutant over the course of the assay (Table 3) which showed that the mutant had a FAME/TOC ratio of from about 0.3 to about 0.7 over the course of the assay, whereas the FAME/TOC ratio of the wild type assayed under identical culture conditions varied between about 0.25 to 0.3.

TABLE 1

Daily production of FAME (μg/ml) by wild type and GE-15360 knockout cells in semi-continuous culture with daily dilution in nitrate-only medium.

| DAY | 1 | 2 | 3 | 4 | 5 | 6 | 7 |
|---|---|---|---|---|---|---|---|
| WT-3730 | 67.7 | 61.0 | 55.4 | 53.0 | 52.6 | 52.2 | 48.0 |
|  | (2.3) | (2.8) | (1.0) | (0.1) | (3.0) | (1.0) | (4.8) |
| GE-15360 | 72.7 | 111.3 | 103.3 | 107.6 | 113.4 | 96.5 | 89.4 |
|  | (0.9) | (0.7) | (2.4) | (1.0) | (3.5) | (2.0) | (6.5) |
| Increase % (GE-15360 vs. WT) | 7.4% | 82.5% | 86.5% | 103.0% | 115.6% | 84.9% | 86.3% |

| DAY | 8 | 9 | 10 | 11 | 12 | 13 |
|---|---|---|---|---|---|---|
| WT-3730 | 48.2 | 51.6 | 49.8 | 51.2 | 50.5 | 51.0 |
|  | (1.7) | (3.4) | (2.4) | (1.2) | (2.2) | (1.8) |
| GE-15360 | 85.2 | 85.3 | 81.9 | 76.2 | 71.1 | 76.5 |
|  | (3.6) | (2.8) | (3.4) | (0.3) | (3.1) | (2.1) |
| Increase % (GE-15360 vs. WT) | 76.8% | 65.3% | 64.5% | 48.8% | 40.8% | 50.0% |

TABLE 2

Daily production of TOC (μg/ml) by wild type and GE-15360 knockout cells in semi-continuous culture with daily dilution in nitrate-only medium.

| DAY | 1 | 2 | 3 | 4 | 5 | 6 | 7 |
|---|---|---|---|---|---|---|---|
| WT-3730 | 3.55 | 3.20 | 2.91 | 2.78 | 2.76 | 2.74 | 2.52 |
|  | (4.65) | (13.86) | (3.03) | (2.13) | (6.03) | (2.36) | (2.65) |
| GE-15360 | 3.82 | 5.84 | 5.42 | 5.65 | 5.95 | 5.07 | 4.70 |
|  | (5.10) | (3.31) | (2.05) | (3.13) | (2.86) | (2.97) | (2.10) |
| Increase % (GE-15360 vs. WT) | 7.61% | 82.50% | 86.25% | 103.24% | 115.58% | 85.04% | 86.51% |

| DAY | 8 | 9 | 10 | 11 | 12 | 13 |
|---|---|---|---|---|---|---|
| WT-3730 | 2.53 | 2.71 | 2.61 | 2.69 | 2.65 | 2.68 |
|  | (3.08) | (2.90) | (6.63) | (5.73) | (5.86) | (5.65) |
| GE-15360 | 4.47 | 4.48 | 4.30 | 4.00 | 3.73 | 4.02 |
|  | (2.74) | (3.52) | (3.10) | (3.77) | (0.62) | (1.42) |
| Increase % (GE-15360 vs. WT) | 76.68% | 65.31% | 64.75% | 48.70% | 40.75% | 50.00% |

TABLE 3

Daily FAME/TOC ratios of wild type and GE-15360 knockout cells in semi-continuous culture with daily dilution in nitrate-only medium.

| DAY | 1 | 2 | 3 | 4 | 5 | 6 | 7 |
|---|---|---|---|---|---|---|---|
| WT-3730 | 0.3 | 0.258 | 0.275 | 0.274 | 0.279 | 0.275 | 0.265 |
|  | (0.01) | (0.01) | (0.00) | (0.00) | (0.01) | (0.00) | (0.03) |
| GE-15360 | 0.3 | 0.5 | 0.6 | 0.6 | 0.7 | 0.6 | 0.4 |
|  | (0.01) | (0.01) | (0.02) | (0.01) | (0.02) | (0.01) | (0.37) |

TABLE 3-continued

Daily FAME/TOC ratios of wild type and GE-15360 knockout cells in semi-continuous culture with daily dilution in nitrate-only medium.

| | | | | | | |
|---|---|---|---|---|---|---|
| Increase % (GE-15360 vs. WT) | 0.0% | 93.8% | 118.2% | 119.0% | 150.9% | 118.2% | 50.9% |

| DAY | 8 | 9 | 10 | 11 | 12 | 13 |
|---|---|---|---|---|---|---|
| WT-3730 | 0.254 (0.01) | 0.270 (0.02) | 0.258 (0.00) | 0.271 (0.01) | 0.280 (0.02) | 0.258 (0.00) |
| GE-15360 | 0.4 (0.36) | 0.6 (0.01) | 0.6 (0.03) | 0.6 (0.02) | 0.6 (0.03) | 0.6 (0.02) |
| Increase % (GE-15360 vs. WT) | 57.5% | 122.2% | 132.6% | 121.4% | 114.3% | 132.6% |

Although the invention has been described with reference to the above examples, it will be understood that modifications and variations are encompassed within the spirit and scope of the invention. Accordingly, the invention is limited only by the following claims.

---

What is claimed is:

1. A mutant Eustigmatophyte microorganism having a disrupted gene encoding a polypeptide comprising a tetratricopeptide repeat (TPR) domain having at least 80% amino acid sequence identity to SEQ ID NO: 3, wherein the mutant microorganism:
   a) produces at least 25% more lipid than a control microorganism not having attenuated expression of the gene encoding a polypeptide comprising a TPR domain; and/or
   b) exhibits increased partitioning of carbon to lipid with respect to the control microorganism;
   when the mutant microorganism and control microorganism are cultured under identical conditions.

2. The mutant microorganism of claim 1, wherein the TPR domain has at least 90%, amino acid sequence identity to the amino acid sequence set forth in SEQ ID NO:1.

3. The mutant microorganism of claim 1, wherein the tetratricopeptide repeat (TPR) domain has at least 90% amino acid sequence identity to SEQ ID NO:3.

4. The mutant microorganism of claim 3, wherein the polypeptide comprises a domain of unknown function (DUF4470) that has at least 80%, identity to the amino acid sequence set forth in SEQ ID NO: 2.

5. The mutant microorganism of claim 1, wherein the mutant microorganism comprises one or more mutations to or affecting expression of a gene in the Naga_100148g8 locus in the mutant Eustigmatophyte microorganism.

6. The mutant microorganism of claim 5, wherein the mutant microorganism comprises a mutation to, or a mutation affecting expression of, a gene comprising an open reading frame having at least 90% sequence identity to SEQ ID NO:4.

7. The mutant microorganism of claim 1, wherein the control microorganism is a wild type microorganism.

8. The mutant microorganism of claim 1, wherein the mutant microorganism produces at least 80% more fatty acid methyl ester-derivatizable lipids (FAME lipids) than a control microorganism when cultured in a medium comprising nitrate as the sole nitrogen source.

9. The mutant microorganism of claim 8, wherein the mutant microorganism is an alga and produces at least 80% more FAME lipids than a control alga when cultured under photoautotrophic conditions.

10. The mutant microorganism according to claim 1, wherein the mutant microorganism exhibits a FAME/TOC ratio at least 80% higher than the FAME/TOC ratio of the control microorganism.

11. The mutant microorganism according to claim 10, wherein the mutant microorganism exhibits a FAME/TOC ratio of between about 0.25 and about 0.75 under conditions that are nitrogen replete with respect to the control microorganism.

12. The mutant microorganism according to claim 1, wherein lipid production or productivity is determined using semi-continuous, culture conditions.

13. The mutant microorganism of claim 1, wherein said identical conditions comprise culturing said mutant and control microorganisms in a medium comprising less than 2 mM ammonium.

14. The mutant microorganism of claim 1, wherein the mutant microorganism is a genetically engineered mutant.

15. The mutant microorganism of claim 1, wherein the disruption comprises a partial or total deletion, a truncation, a frameshift mutation, or an insertional mutation.

16. The mutant microorganism of claim 1, wherein the disruption comprises a knockout mutation in the gene encoding a polypeptide that includes a TPR domain, or a gene affecting expression thereof.

17. The mutant microorganism according to claim 1, wherein the mutant microorganism comprises at least one additional genetic modification that confers herbicide resistance, toxin resistance, enhanced growth properties, enhanced photosynthetic efficiency, or enhanced lipid production or accumulation.

18. A method of producing lipid, comprising culturing a mutant microorganism according to claim 1 in a culture medium to produce lipid.

19. The method of claim 18, wherein the microorganism is cultured using batch, continuous, or semi-continuous culture conditions.

20. The method of claim 18 or 19, wherein the culturing is under photoautotrophic conditions.

21. The mutant Eustigmatophyte microorganism of claim 1, wherein the microorganism is of the genus *Nannochloropsis*.

22. The mutant Eustigmatophyte microorganism of claim 3, wherein the microorganism is of the genus *Nannochloropsis*.

* * * * *